(12) United States Patent
Björklund et al.

(10) Patent No.: US 9,593,312 B2
(45) Date of Patent: Mar. 14, 2017

(54) VIRAL VECTOR CONSTRUCT FOR NEURON SPECIFIC OPTIMIZED CONTINUOUS DOPA SYNTHESIS IN VIVO

(71) Applicant: Genepod Therapeutics AB, Lund (SE)

(72) Inventors: Tomas Björklund, Lund (SE); Anders Björklund, Lund (SE); Deniz Kirik, Lund (SE)

(73) Assignee: Genepod Therapeutics AB, Lund (SE)

( * ) Notice: Subject to any disclaimer, the term of this patent is extended or adjusted under 35 U.S.C. 154(b) by 0 days.

(21) Appl. No.: 14/242,648

(22) Filed: Apr. 1, 2014

(65) Prior Publication Data
US 2015/0065560 A1    Mar. 5, 2015

Related U.S. Application Data

(63) Continuation of application No. 13/505,879, filed as application No. PCT/EP2010/067155 on Nov. 9, 2010, now abandoned.

(60) Provisional application No. 61/259,502, filed on Nov. 9, 2009.

(51) Int. Cl.
| | | |
|---|---|---|
| *C12N 7/00* | (2006.01) | |
| *C12N 9/02* | (2006.01) | |
| *C12N 9/78* | (2006.01) | |
| *C12N 9/88* | (2006.01) | |
| *C12N 15/86* | (2006.01) | |
| *A61K 48/00* | (2006.01) | |

(52) U.S. Cl.
CPC ............. *C12N 7/00* (2013.01); *C12N 9/0071* (2013.01); *C12N 9/78* (2013.01); *C12N 9/88* (2013.01); *C12N 15/86* (2013.01); *A61K 48/00* (2013.01); *C12N 2750/00043* (2013.01); *C12N 2750/14143* (2013.01); *C12N 2830/008* (2013.01); *C12N 2830/34* (2013.01); *C12N 2830/40* (2013.01); *C12N 2830/42* (2013.01); *C12N 2830/48* (2013.01); *C12N 2830/50* (2013.01); *C12N 2830/60* (2013.01); *C12Y 114/16002* (2013.01); *C12Y 305/04016* (2013.01)

(58) Field of Classification Search
CPC ............ A61K 2121/00; C12N 15/8645; C12N 2750/14143; C12N 2830/008; C12N 2830/34; C12N 2830/42; C12N 2830/48; C12N 2830/50; C12Y 114/16; C12Y 305/04016
USPC ............... 424/93.2, 93.6; 435/320.1; 514/44; 536/23.1, 23.5, 24.1
See application file for complete search history.

(56) References Cited

U.S. PATENT DOCUMENTS

| | | | |
|---|---|---|---|
| 7,259,015 B2 * | 8/2007 | Kingsman ............ | C12N 9/0071 435/320.1 |
| 7,588,757 B2 | 9/2009 | Ozawa et al. | |
| 7,943,374 B2 * | 5/2011 | Hildinger ............... | C12N 15/86 435/320.1 |
| 2002/0172664 A1 | 11/2002 | Ozawa et al. | |
| 2003/0059941 A1 | 3/2003 | Prockop et al. | |
| 2006/0234347 A1 | 10/2006 | Harding et al. | |
| 2007/0037165 A1 * | 2/2007 | Venter .................. | C12Q 1/6883 435/6.11 |
| 2007/0042462 A1 * | 2/2007 | Hildinger ............... | C12N 15/86 435/69.1 |

FOREIGN PATENT DOCUMENTS

| | | |
|---|---|---|
| WO | WO-96/05319 A1 | 2/1996 |
| WO | WO 97/18319 | * 5/1997 |
| WO | WO-97/18319 A1 | 5/1997 |
| WO | WO-02/29065 A2 | 4/2002 |
| WO | WO-2005/074605 A2 | 8/2005 |

OTHER PUBLICATIONS

Shevtsova et al, Exp. Physiol. 90(1):53-59, 2004.*
Hennecke et al, Nuc. Acids Res. 29(16):3327-3334, 2001.*
Xu et al, Gene Therapy 8:1323-1332, 2001.*
Martin et al, Methods 28:267-275, 2002.*
Grieger et al, J. Virol. 79(15):9933-9944, 2005.*
Allocca et al, J. Clin. Invest. 118:1955-1964, 2008.*
Lai et al, Mol. Therapy 18(1):75-79, 2010.*
International Preliminary Report on Patentability for PCT/EP2010/067155, 31 pages (Mar. 6, 2013).
Lotti, F. et al., Transcriptional Targeting of Lentiviral Vectors by Long Terminal Repeat Enhancer Replacement, Journal of Virology, 76(8): 3996-4007 (2002).
Aguilar Salegio, E. et al., Magnetic Resonance Imaging-Guided Delivery of Adeno-Associated Virus Type 2 to the Primate Brain for the Treatment of Lysosomal Storage Disorders, Human Gene Therapy, 21:1093-1103(2010).
Amendola, M. et al., Coordinate dual-gene transgenesis by lentiviral vectors carrying synthetic bidirectional promoters, Nature Biotechnology, 23(1):108-116 (2005).
Antonini, A. Movement disorders: towards new therapies in Parkinson's disease, The lancet.com/neurology, 11:7-8 (2012).

(Continued)

*Primary Examiner* — Kevin Hill
(74) *Attorney, Agent, or Firm* — Dinsmore & Shohl LLP; Weston Gould

(57) ABSTRACT

The present invention relates to a one-vector expression system comprising a sequence encoding two polypeptides, such as tyrosine hydroxylase (TH) and GTP-cyclohydrolase 1 (GCH1). The two polypeptides can be should preferentially be expressed at a ratio between 3:1 and 15:1, such as between 3:1 and 7:1. The invention is useful in the treatment of catecholamine deficient disorders, such as dopamine deficient disorders including but not limited to Parkinson's Disease. Moreover, the present invention provides a method to deliver the vector construct in order to limit the increased production of the catecholamine to the cells in need thereof.

24 Claims, 20 Drawing Sheets

(56) References Cited

OTHER PUBLICATIONS

Azzouz, M. et al., Multicistronic Lentiviral Vector-Mediated Striatal Gene Transfer of Aromatic $_L$-Amino Acid Decarboxylase, Tyrosine Hydroxylase, and GTP Cyclohydrolase I Induces Sustained Transgene Expression, Dopamine Production, and Functional Improvement in a Rat Model of Parkinson's Disease, The Journal of Neuroscience, 22(23):10302-10312 (2002).
Bankiewicz, K.S. et al, Long-Term Clinical Improvement in MPTP-Lesioned Primates after Gene Therapy with AAV-hAADC; Molecular Therapy, 14(4):564-570 (2006).
Beyer, P.L. et al., Weight change and body composition in patients with Parkinson's disease, Journal of the American Dietetic Association, 95(9):979-983 (1995).
Bilang-Bleuel, A. et al., Intrastriatal injection of an adenoviral vector expressing glial-cell-line-derived neurotrophic factor prevents dopaminergic neuron degeneration and behavioral impairment in a rat model of Parkinson disease, Proceedings of the National Academy of Sciences of the United States of America, 94:8818-8823 (1997).
Bjorklund, A. et al., Gene Therapy for Dopamine Replacement in Parkinson's Disease, Science Translational Medicine, 1(2):2-5 (2009).
Bjorklund, A. et al., Gene Therapy for Parkinson's Disease Shows Promise, Science Translational Medicine, 3(79):1-2 (2011).
Bjorklund, T. et al., Gene therapy for dopamine replacement, Progress in Brain Research, 184:221-235 (2010).
Bjorklund, T. et al., Gene Therapy for Parkinson's Disease, Movement Disorders, 25(Suppl. 1):S161-S173 (2010).
Bjorklund, T. et al., Optimization of continuous in vivo DOPA production and studies on ectopic DA synthesis using rAAV5 vectors in Parkinsonian rats, Journal of Neurochemistry, 111(2):355-367 (2009).
Bjorklund, T. et al., Optimized adeno-associated viral vector-mediated striatal DOPA delivery restores sensorimotor function and prevents dyskinesias in a model of advanced Parkinson's disease, Brain, 133:496-511 (2010).
Bjorklund, T. et al., Scientific rationale for the development of gene therapy strategies for Parkinson's disease, Biochimica et Biophysica Acta, 1792:703-713 (2009).
Carlsson, T. et al., Restoration of the Striatal Dopamine Synthesis for Parkinson's Disease: Viral Vector-Mediated Enzyme Replacement Strategy, Current Gene Therapy, 7:109-120 (2007).
Carlsson, T. et al., Reversal of dyskinesias in an animal model of Parkinson's disease by continuous L-DOPA delivery using rAAV vectors, Brain, 128:559-569 (2005).
Carlsson, T. et al., Serotonin Neuron Transplants Exacerbate $_L$-DOPA-Induced Dyskinesias in a Rat Model of Parkinson's Disease, The Journal of Neuroscience, 27(30):8011-8022 (2007).
Cederfjall, E. et al., Design of a Single AAV Vector for Coexpression of TH and GCH1 to Establish Continuous DOPA Synthesis in a Rat Model of Parkinson's Disease, Molecular Therapy, pp. 1-12 (2011).
Chakos, M.H. et al., Striatal Enlargement in Rats Chronically Treated with Neuroleptic, Biological Psychiatry, 44(8):675-684 (1998).
Choi-Lundberg, D.L. et al., Behavioral and Cellular Protection of Rat Dopaminergic Neurons by an Adenoviral Vector Encoding Glial Cell Line-Derived Neurotrophic Factor, Experimental Neurology, 154:261-275 (1998).
Choi-Lundberg, D.L. et al., Dopaminergic Neurons Protected from Degeneration by GDNF Gene Therapy, Science, 275:838-841 (1997).
Christine, C.W. et al., Safety and tolerability of putaminal *AADC* gene therapy for Parkinson disease, Neurology, 73:1662-1669 (2009).
Daya, S. et al., Gene Therapy Using Adeno-Associated Virus Vectors, Clinical Microbiology Reviews, 21(4):583-593 (2008).
Delikanaki-Skaribas, E. et al., Daily Energy Expenditure, Physical Activity, and Weight Loss in Parkinson's Disease Patients, Movement Disorders, 24(5):667-671 (2009).
Dodiya, H.B. et al., Differential Transduction Following Basal Ganglia Administration of Distinct Pseudotyped AAV Capsid Serotypes in Nonhuman Primates, Molecular Therapy, pp. 1-9 (2009).
Dowd, E. et al., The Corridor Task: A simple test of lateralised response selection sensitive to unilateral dopamine deafferentation and graft-derived dopamine replacement in the striatum, Brain Research Bulletin, 68:24-30 (2005).
During, M.J. et al., In vivo expression of therapeutic human genes for dopamine production in the caudates of MPTP-treated monkeys using an AAV vector, Gene Therapy, 5: 820-827 (1998).
During, M.J. et al., Long-Term Behavioral Recovery in Parkinsonian Rats by an HSV Vector Expressing Tyrosine Hydroxylase, Science, 266:1399-1403 (1994).
Emdad, R. et al., Morphometric and Psychometric Comparisons between Non-Substance-Abusing Patients with Posttraumatic Stress Disorder and Normal Controls, Psychotheraphy and Psychosomatics, 75:122-132 (2006).
Eslamboli, A. et al., Long-term consequences of human alpha-synuclein overexpression in the primate ventral midbrain, Brain, 130:799-815 (2007).
Fraley, R. et al., New generation liposomes: the engineering of an efficient vehicle for intracellular delivery of nucleic acids, Trends in Biochemical Science, 6:77-80 (1981).
Gabery, S. et al., Characterization of a rat model of Huntington's disease based on targeted expression of mutant *huntingtin* in the forebrain using adeno-associated viral vectors, European Journal of Neuroscience, pp. 1-12 (2012).
Gradinaru, V. et al., Molecular and Cellular Approaches for Diversifying and Extending Optogenetics, Cell, 141:154-165 (2010).
Grieger, J.C. et al., Packaging Capacity of Adeno-Associated Virus Serotypes: Impact of Larger Genomes on Infectivity and Postentry Steps, Journal of Virology, 79(15):9933-9944 (2005).
Grimm, D. et al., Novel Tools for Production and Purification of Recombinant Adenoassociated Virus Vectors, Human Gene Therapy, 9:2745-2760 (1998).
Hadaczek, P. et al., Eight Years of Clinical Improvement in MPTP-Lesioned Primates After Gene Therapy With AAV2-hAADC, Molecular Therapy, 18(8):1458-1461 (2010).
Hauswirth, W.W. et al., Production and Purification of Recombinant Adeno-associated Virus, Methods in Enzymology, 316:743-761 (2000).
Hioki, H. et al., Efficient gene transduction of neurons by lentivirus with enhanced neuron-specific promoters, Gene Therapy, 14:872-882 (2007).
Howells, D.W. et al., Direct analysis of tetrahydrobiopterin in cerebrospinal fluid by high-performance liquid chromatography with redox electrochemistry: prevention of autoxidation during storage and analysis, Clinical Chimica Acta, 167:23-30 (1987).
Hult, S. et al., Mutant Huntingtin Causes Metabolic Imbalance by Disruption of Hypothalamic Neurocircuits, Cell Metabolism, 13:428-439 (2011).
International Search Report for PCT/EP10/67155, 8 pages (May 23, 2011).
Iwamoto, M. et al., A General Chemical Method to Regulate Protein Stability in the Mammalian Central Nervous System, Chemistry & Biology, 17:981-988 (2010).
Jarraya, B. et al. Dopamine Gene Therapy for Parkinson's Disease in a Nonhuman Primate Without Associated Dyskinesia, Science Translational Medicine, 1(2):1-11 (2009).
Kaplitt, M.G. et al., Long-term gene expression and phenotypic correction using adeno-associated virus vectors in the mammalian brain; Nature Genetics, 8:148-154 (1994).
Kaplitt, M.G. et al., Safety and tolerability of gene therapy with an adeno-associated virus (AAV) borne *GAD* gene for Parkinson's disease: an open label, phase I trial, Lancet, 369:2097-2105 (2007).
Kim, J. et al., mGRASP enables mapping mammalian synaptic connectivity with light microscopy, Nature Methods, 9(1):96-104 (2012).
Kim, S.J. et al. Effective relief of neuropathic pain by adeno-associated virus-mediated expression of a small hairpin RNA against GTP cyclohydrolase 1, Molecular Pain, 5:67 (2009).

(56) References Cited

OTHER PUBLICATIONS

Kirik, D. et al., Growth and Functional Efficacy of Intrastriatal Nigral Transplants Depend or the Extent of Nigrostriatal Degeneration, The Journal of Neuroscience, 21(8): 2889-2896 (2001).
Kirik, D. et al., Imaging in cell-based therapy for neurodegenerative diseases, European Journal of Nuclear Medicine and Molecular Imaging, 32(14):5417-5434 (2005).
Kirik, D. et al., Reversal of motor impairments in parkinsonian rats by continuous intrastriatal delivery of L-dopa using rAAV-mediated gene transfer, Proceedings of the National Academy of Sciences of the United States of America, 99(7):4708-4713 (2002).
Kornum, B.R. et al., Adeno-associated viral vector serotypes 1 and 5 targeted to the neonatal rat and pig striatum induce widespread transgene expression in the forebrain, Experimental Neurology, 222:70-85 (2010).
Kugler, S. et al., Differential transgene expression in brain cells in vivo and in vitro from AAV-2 vectors with small transcriptional control units, Virology, 311:89-95 (2003).
Kugler, S. et al., Human synapsin 1 gene promoter confers highly neuron-specific long-term transgene expression from an adenoviral vector in the adult rat brain depending on the transduced area, Gene Therapy, 10:337-347 (2003).
Leriche, L. et al., Positron Emission Tomography Imaging Demonstrates Correlation between Behavioral Recovery and Correction of Dopamine Neurotransmission after Gene Therapy, The Journal of Neuroscience, 29(5):1544-1553 (2009).
Lewitt, P.A. et al., AAV2-GAD gene therapy for advanced Parkinson's disease: a double-blind, sham-surgery controlled, randomised trial, The Lancet Neurology, 10:309-319 (2011).
Lin, D., et al., Central nervous system-directed AAV2/5-mediated gene therapy synergizes with bone marrow transplantation in the murine model of globoid-cell leukodystrophy, Mol. Ther., 15(1): 44-52, 2007.
Lu, L. et al., Therapeutic benefit of TH-engineered mesenchymal stem cells for Parkinson's disease, Brain Research Protocols, 15:46-51 (2005).
Lundberg, C. et al., Applications of Lentiviral Vectors for Biology and Gene Therapy of Neurological Disorders, Current Gene Therapy, 8:461-473 (2008).
Mandel, R.J. et al., Characterization of Intrastriatal Recombinant Adeno-Associated Virus-Mediated Gene Transfer of Human Tyrosine Hydroxylase and Human GTP-Cyclohydrolase I in a Rat Model of Parkinson's disease, The Journal of Neuroscience, 18(11):4271-4284 (1998).
Mandel, R.J. et al., Midbrain injection of recombinant adeno-associated virus encoding rat glial cell line-derived neurotrophic factor protects nigral neurons in a progressive 6-hydroxydopamine-induced degeneration model of Parkinson's disease in rats, Proceedings of the National Academy of Sciences of the United States of America, 94:14083-14088 (1997).
Manfredsson, F.P. et al., Tight Long-term Dynamic Doxycycline Responsive Nigrostriatal GDNF Using a Single rAAV Vector, Molecular Therapy, pp. 1-11 (2009).
Markakis, E.A. et al., Comparative Transduction Efficiency of AAV Vector Serotypes 1-6 in the Substantia Nigra and Striatum of the Primate Brain, Molecular Therapy, 18(3):588-593 (2010).
Marks, W.J. et al., Gene delivery of AAV2-neurturin for Parkinson's disease: a double-blind, randomised, controlled trial The Lancet Neurology, 9:1164-1172 (2010).
Merrifield, R.B., Solid Phase Peptide Synthesis. I. The Synthesis of a Tetrapeptide, Journal of the American Chemical Society, 85:2149-2146 (1963).
Mizuguchi, H. et al., IRES-Dependent Second Gene Expression Is Significantly Lower Than Cap-Dependent First Gene Expression in a Bicistronic Vector, Molecular Therapy, 1(4):376-382 (2000).
Montoya, C.P. et al., The "staircase test": a measure of independent forelimb reaching and grasping abilities in rats, Journal of Neuroscience Methods, 36:219-228 (1991).
Mouradian, M.M. et al., Pathogenesis of Dyskinesias in Parkinson's Disease, Annals of Neurology, 25(5):523-527 (1989).
Muramatsu, S. et al., A Phase I Study of Aromatic $_L$-Amino Acid Decarboxylase Gene Therapy for Parkinson's Disease, Molecular Therapy, 18(9):1731-1735 (2010).
Muramatsu, S. et al., Behavioral Recovery in a Primate Model of Parkinson's Disease by Triple Transduction of Striatal Cells with Adeno-Associated Viral Vectors Expressing Dopamine-Synthesizing Enzymes, Human Gene Therapy, 13:345-354 (2002).
Needleman, S.B. et al., A General Method Applicable to the Search for Similarities in the Amino Acid Sequence of Two Proteins, Journal of Molecular Biology, 48:443-453 (1970).
Olsson, M. et al., Forelimb Akinesia in the Rat Parkinson Model: Differential Effects of Dopamine Agonists and Nigral Transplants as Assessed by a New Stepping Test, The Journal of Neuroscience, 15(5):3863-3875 (1995).
Pearson, W.R. et al., Improved tools for biological sequence comparison, Proceedings of the National Academy of Sciences of the United States of America, 85:2444-2448 (1988).
Romero-Ramos, M. et al., Low selenium diet induces tyrosine hydroxylase enzyme in nigrostriatal system of the rat, Molecular Brain Research, 84:7-16 (2000).
Rotstein, M. et al., Consideration of gene therapy for paediatric neurotransmitter diseases, Journal of Inherited Metabolic Disease, 32:387-394 (2009).
Schallert, T. et al., Excessive Bracing Reactions and Their Control by Atropine and $_L$-DOPA in an Animal Analog of Parkinsonism, Experimental Neurology, 64:33-43 (1979).
Shen, Y. et al., Triple Transduction with Adeno-Associated Virus Vectors Expressing Tyrosine Hydroxylase, Aromatic-$_L$-Amino-Acid Decarboxylase, and GTP Cyclohydrolase I for Gene Therapy of Parkinson's Disease, Human Gene Therapy, 11:1509-1519 (2000).
Shevtsova, Z. et al., Promoters and serotypes: targeting of adeno-associated virus vectors for gene transfer in the rat central nervous system in vitro and in vivo, Experimental Physiology, 90(1):53-59 (2005).
Smith, T. et al., Comparison of Biosequences, Advances in Applied Mathematics, 2:482-489 (1981).
Tsai, H. et al., Phasic Firing in Dopaminergic Neurons is Sufficient for Behavioral Conditioning, Science, 324:1080-1084 (2009).
UC, E.Y. et al., Predictors of Weight Loss in Parkinson's Disease, Movement Disorders, 21(7):930-936 (2006).
Uchino, H. et al., Transport of Amino Acid-Related Compounds Mediated by $_L$-Type Amino Acid Transporter 1 (LAT1): Insights Into the Mechanisms of Substrate Recognition, Molecular Pharmacology, 61(4):729-737 (2002).
Ulusoy, A. et al., Dose Optimization for Long-term rAAV-mediated RNA Interference in the Nigrostriatal Projection Neurons, Molecular Therapy, 17:1574-1584 (2009).
Ulusoy, A. et al., Dysregulated dopamine storage increases the vulnerability to x-synuclein in nigral neurons, Neurobiology of Disease, 47:367-377 (2012).
Ulusoy, A. et al., In vivo gene delivery for development of mammalian models for Parkinson's disease, Experimental Neurology, 209:89-100 (2008).
Ulusoy, A. et al., Presynaptic dopaminergic compartment determines the susceptibility to L-DOPA-induced dyskinesia in rats, Proceedings of the National Academy of Sciences of the United States of America, 107(29):13159-13164 (2010).
Ungerstedt, U. et al., Quantitative recording of rotational behavior in rats after 6-hydroxy-dopamine lesions of the nigrostriatal dopamine system, Brain Research, 24:485-493 (1970).
Van Der Perren, A. et al., Efficient and stable transduction of dopaminergic neurons in rat substantia nigra by rAAV 2/1, 2/2, 2/5, 2/6.2, 2/7, 2/8 and 2/9, Gene Therapy, 18:517-527 (2011).
Waymire, J.C. et al., Lack of regulation of aromatic $_L$-amino acid decarboxylase in intact bovine chromaffin cells, Journal of Neurochemistry, 81:589-593 (2002).
Winkler, C. et al., Intranigral Transplants of GABA-Rich Striatal Tissue Induce Behavioral Recovery in the Rat Parkinson Model and Promote the Effects Obtained by Intrastriatal Dopaminergic Transplants, Experimental Neurology, 155:165-186 (1999).
Winkler, C. et al., $_L$-DOPA-Induced Dyskinesia in the Intrastriatal 6-Hydroxydopamine Model of Parkinson's Disease: Relation to

(56) References Cited

OTHER PUBLICATIONS

Motor and Cellular Parameters of Nigrostriatal Function, Neurobiology of Disease, 10:165-186 (2002).
Written Opinion for PCT/EP10/67155, 12 pages (May 23, 2011).
Wu, Z. et al., Effect of Genome Size on AAV Vector Packaging, Molecular Therapy, 18(1):80-86 (2010).
Yin, D. et al., Striatal volume differences between non-human and human primates, Journal of Neuroscience Methods, 176(2):200-205 (2009).
Zufferey, R. et al., Woodchuck Hepatitis Virus Posttransciptional Regulatory Element Enhances Expression of Transgenes Delivered by Retroviral Vectors, Journal of Virology, 73(4):2886-2892 (1999).
Chaudhuri, A. et al., Interaction of Genetic and Environmental Factors in a Drosophila Parkinsonism Model, The Journal of Neuroscience, 27(10):2457-2467 (2007).
Yu, X. et al., Lentiviral Vectors with Two Independent Internal Promoters Transfer High-Level Expression of Multiple Transgenes to Human Hematopoietic Stem-Progenitor Cells, Molecular Therapy, 7(6):827-838 (2003).

\* cited by examiner

```
                10        20        30        40        50
                 *         *         *         *         *
  1  ttggccactccctctctgcgcgctcgctcgctcactgaggccgggcgacc  50
     >>>>>>>>>>>>>>>>>>>>>>>>>>>>>>>>>>>>>>>>>>>>>>>>>>
     AAV ITR 60        70        80        90       100
                 *         *         *         *         *
 51  aaaggtcgcccgacgcccgggctttgcccgggcggcctcagtgagcgagc 100
     >>>>>>>>>>>>>>>>>>>>>>>>>>>>>>>>>>>>>>>>>>>>>>>>>>
     AAV ITR 110       120       130       140       150
                 *         *         *         *         *
101  gagcgcgcagagagggagtggccaactccatcactaggggttcctcagat 150
     >>>>>>>>>>>>>>>>>>>>>>>>>>>>>>>>>>>>>>>>>>>>>>>>>>
     AAV ITR 160       170       180       190       200
                 *         *         *         *         *
151  cgggcTGCAGGAATTGGCCGCTCTAGACTCTAGCTGCAGAGGGACCTGCG 200
                                >>>>>>>>>>>>>>>>>>>>>>>>
                                Human Synapsin Promoter 210       220       230       240       250
                 *         *         *         *         *
201  TATGAGTGCAAGTGGGTTTTAGGACCAGGATGAGGCGGGGTGGGGGTGCC 250
     >>>>>>>>>>>>>>>>>>>>>>>>>>>>>>>>>>>>>>>>>>>>>>>>>>
     Human Synapsin Promoter 260       270       280       290       300
                 *         *         *         *         *
251  TACCTGACGACCGACCCCGACCCACTGGACAAGCACCCAACCCCCATTCC 300
     >>>>>>>>>>>>>>>>>>>>>>>>>>>>>>>>>>>>>>>>>>>>>>>>>>
     Human Synapsin Promoter 310       320       330       340       350
                 *         *         *         *         *
301  CCAAATTGCGCATCCCCTATCAGAGAGGGGGAGGGAAACAGGATGCGGC 350
     >>>>>>>>>>>>>>>>>>>>>>>>>>>>>>>>>>>>>>>>>>>>>>>>>>
     Human Synapsin Promoter 360       370       380       390       400
                 *         *         *         *         *
```

FIG. 6

```
                                 410        420        430        440        450
                                  *          *          *          *          *
351 GAGGCGCGTGCGCACTGCCAGCTTCAGCACCGCGGACAGTGCCTTCGCCC 400
    >>>>>>>>>>>>>>>>>>>>>>>>>>>>>>>>>>>>>>>>>>>>>>>>>>
    Human Synapsin Promoter 410        420        430        440        450
                   *          *          *          *          *
401 CCGCCTGGCGGCGCGCGCCACCGCCGCCTCAGCACTGAAGGCGCGCTGAC 450
    >>>>>>>>>>>>>>>>>>>>>>>>>>>>>>>>>>>>>>>>>>>>>>>>>>
    Human Synapsin Promoter 460        470        480        490        500
                   *          *          *          *          *
451 GTCACTCGCCGGTCCCCCGCAAACTCCCCTTCCCGGCCACCTTGGTCGCG 500
    >>>>>>>>>>>>>>>>>>>>>>>>>>>>>>>>>>>>>>>>>>>>>>>>>>
    Human Synapsin Promoter 510        520        530        540        550
                   *          *          *          *          *
501 TCCGCGCCGCCGCCGGCCCAGCCGGACCGCACCACGCGAGGCGCGAGATA 550
    >>>>>>>>>>>>>>>>>>>>>>>>>>>>>>>>>>>>>>>>>>>>>>>>>>
    Human Synapsin Promoter 560        570        580        590        600
                   *          *          *          *          *
551 GGGGGGCACGGGCGCGACCATCTGCGCTGCGGCGCCGGCGACTCAGCGCT 600
    >>>>>>>>>>>>>>>>>>>>>>>>>>>>>>>>>>>>>>>>>>>>>>>>>>
    Human Synapsin Promoter 610        620        630        640        650
                   *          *          *          *          *
601 GCCTCAGTCTGCGGTGGGCAGCGGAGGAGTCGTGTCGTGCCTGAGAGCGC 650
    >>>>>>>>>>>>>>>>>>>>>>>>>>>>>>>>>>>>>>>>>>>>>>>>>>
    Human Synapsin Promoter 660        670        680        690        700
                   *          *          *          *          *
651 AGTCGAATTCAAGCTGCTAGCAAGGATCCACCGGTAACATGGAGAAGGGC 700
                                          M  E  K  G
                                          >>>>>>>>>>>>
                                          GTP cyclohydrolase 1
    >>>>>>
    Human Synapsin Promoter 710        720        730        740        750
                   *          *          *          *          *
701 CCTGTGCGGGCACCGGCGGAGAAGCCGCGGGGCGCCAGGTGCAGCAATGG 750
    P  V  R  A  P  A  E  K  P  R  G  A  R  C  S  N  G
```

FIG. 6
CONTINUED

```
                                >>>>>>>>>>>>>>>>>>>>>>>>>>>>>>>>>>>>>>>>>>>>>>>>>>>
                                GTP cyclohydrolase 1 isoform 1

760        770        780        790        800
                                   *     *     *     *     *     *     *     *     *     *
              751  GTTCCCCGAGCGGGATCCGCCGCGGCCCGGGCCCAGCAGGCCGGCGGAGA  800
                    F  P  E  R  D  P  P  R  P  G  P  S  R  P  A  E  K
                                >>>>>>>>>>>>>>>>>>>>>>>>>>>>>>>>>>>>>>>>>>>>>>>>>>>
                                GTP cyclohydrolase 1 isoform 1

810        820        830        840        850
                                   *     *     *     *     *     *     *     *     *     *
              801  AGCCCCCGCGGCCCGAGGCCAAGAGCGCGCAGCCCGCGGACGGCTGGAAG  850
                     P  P  R  P  E  A  K  S  A  Q  P  A  D  G  W  K
                                >>>>>>>>>>>>>>>>>>>>>>>>>>>>>>>>>>>>>>>>>>>>>>>>>>>
                                GTP cyclohydrolase 1 isoform 1

860        870        880        890        900
                                   *     *     *     *     *     *     *     *     *     *
              851  GGCGAGCGGCCCCGCAGCGAGGAGGATAACGAGCTGAACCTCCCTAACCT  900
                    G  E  R  P  R  S  E  E  D  N  E  L  N  L  P  N  L
                                >>>>>>>>>>>>>>>>>>>>>>>>>>>>>>>>>>>>>>>>>>>>>>>>>>>
                                GTP cyclohydrolase 1 isoform 1

910        920        930        940        950
                                   *     *     *     *     *     *     *     *     *     *
              901  GGCAGCCGCCTACTCGTCCATCCTGAGCTCGCTGGGCGAGAACCCCCAGC  950
                      A  A  A  Y  S  S  I  L  S  S  L  G  E  N  P  Q  R
                                >>>>>>>>>>>>>>>>>>>>>>>>>>>>>>>>>>>>>>>>>>>>>>>>>>>
                                GTP cyclohydrolase 1 isoform 1

960        970        980        990        1000
                                   *     *     *     *     *     *     *     *     *     *
              951  GGCAAGGGCTGCTCAAGACGCCCTGGAGGGCGGCCTCGGCCATGCAGTTC  1000
                     Q  G  L  L  K  T  P  W  R  A  A  S  A  M  Q  F
                                >>>>>>>>>>>>>>>>>>>>>>>>>>>>>>>>>>>>>>>>>>>>>>>>>>>
                                GTP cyclohydrolase 1 isoform 1

1010       1020       1030       1040       1050
                                   *     *     *     *     *     *     *     *     *     *
             1001  TTCACCAAGGGCTACCAGGAGACCATCTCAGATGTCCTAAACGATGCTAT  1050
                    F  T  K  G  Y  Q  E  T  I  S  D  V  L  N  D  A  I
                                >>>>>>>>>>>>>>>>>>>>>>>>>>>>>>>>>>>>>>>>>>>>>>>>>>>
                                GTP cyclohydrolase 1 isoform 1

```
1051 ATTTGATGAAGATCATGATGAGATGGTGATTGTGAAGGACATAGACATGT 1100
      F  D  E  D  H  D  E  M  V  I  V  K  D  I  D  M  F
     >>>>>>>>>>>>>>>>>>>>>>>>>>>>>>>>>>>>>>>>>>>>>>>>>
     GTP cyclohydrolase 1 isoform 1

1110      1120      1130      1140      1150
               *    *    *    *    *    *    *    *    *    *
1101 TTTCCATGTGTGAGCATCACTTGGTTCCATTTGTTGGAAAGGTCCATATT 1150
      S  M  C  E  H  H  L  V  P  F  V  G  K  V  H  I
     >>>>>>>>>>>>>>>>>>>>>>>>>>>>>>>>>>>>>>>>>>>>>>>>>
     GTP cyclohydrolase 1 isoform 1

1160      1170      1180      1190      1200
               *    *    *    *    *    *    *    *    *    *
1151 GGTTATCTTCCTAACAAGCAAGTCCTTGGCCTCAGCAAACTTGCGAGGAT 1200
      G  Y  L  P  N  K  Q  V  L  G  L  S  K  L  A  R  I
     >>>>>>>>>>>>>>>>>>>>>>>>>>>>>>>>>>>>>>>>>>>>>>>>>
     GTP cyclohydrolase 1 isoform 1

1210      1220      1230      1240      1250
               *    *    *    *    *    *    *    *    *    *
1201 TGTAGAAATCTATAGTAGAAGACTACAAGTTCAGGAGCGCCTTACAAAAC 1250
      V  E  I  Y  S  R  R  L  Q  V  Q  E  R  L  T  K  Q
     >>>>>>>>>>>>>>>>>>>>>>>>>>>>>>>>>>>>>>>>>>>>>>>>>
     GTP cyclohydrolase 1 isoform 1

1260      1270      1280      1290      1300
               *    *    *    *    *    *    *    *    *    *
1251 AAATTGCTGTAGCAATCACGGAAGCCTTGCGGCCTGCTGGAGTCGGGGTA 1300
      I  A  V  A  I  T  E  A  L  R  P  A  G  V  G  V
     >>>>>>>>>>>>>>>>>>>>>>>>>>>>>>>>>>>>>>>>>>>>>>>>>
     GTP cyclohydrolase 1 isoform 1

1310      1320      1330      1340      1350
               *    *    *    *    *    *    *    *    *    *
1301 GTGGTTGAAGCAACACACATGTGTATGGTAATGCGAGGTGTACAGAAAAT 1350
      V  V  E  A  T  H  M  C  M  V  M  R  G  V  Q  K  M
     >>>>>>>>>>>>>>>>>>>>>>>>>>>>>>>>>>>>>>>>>>>>>>>>>
     GTP cyclohydrolase 1 isoform 1

1360      1370      1380      1390      1400
               *    *    *    *    *    *    *    *    *    *
1351 GAACAGCAAAACTGTGACCAGCACAATGTTGGGTGTGTTCCGGGAGGATC 1400
      N  S  K  T  V  T  S  T  M  L  G  V  F  R  E  D  P
     >>>>>>>>>>>>>>>>>>>>>>>>>>>>>>>>>>>>>>>>>>>>>>>>>
     GTP cyclohydrolase 1 isoform 1
```

FIG. 6
CONTINUED

```
              1410       1420       1430       1440       1450
                *    *    *    *    *    *    *    *    *    *
1401  CAAAGACTCGGGAAGAGTTCCTGACTCTCATTAGGAGCTAATGCATCCCC  1450
        K  T  R  E  E  F  L  T  L  I  R
      >>>>>>>>>>>>>>>>>>>>>>>>>>>>>>>>>>>
      GTP cyclohydrolase 1 isoform 1

1460       1470       1480       1490       1500
                *    *    *    *    *    *    *    *    *    *
1451  ATCGATGATCCAGACATGATAAGATACATTGATGAGTTTGGACAAACCAC  1500
                >>>>>>>>>>>>>>>>>>>>>>>>>>>>>>>>>>>>>>>>
                SV40 late polyA 1510       1520       1530       1540       1550
                *    *    *    *    *    *    *    *    *    *
1501  AACTAGAATGCAGTGAAAAAAATGCTTTATTTGTGAAATTTGTGATGCTA  1550
      >>>>>>>>>>>>>>>>>>>>>>>>>>>>>>>>>>>>>>>>>>>>>>>>>>
      SV40 late polyA 1560       1570       1580       1590       1600
                *    *    *    *    *    *    *    *    *    *
1551  TTGCTTTATTTGTAACCATTATAAGCTGCAATAAACAAGTTAACAACAAC  1600
      >>>>>>>>>>>>>>>>>>>>>>>>>>>>>>>>>>>>>>>>>>>>>>>>>>
      SV40 late polyA 1610       1620       1630       1640       1650
                *    *    *    *    *    *    *    *    *    *
1601  AATTGCATTCATTTTATGTTTCAGGTTCAGGGGGAGGTGTGGGAGGTTTT  1650
      >>>>>>>>>>>>>>>>>>>>>>>>>>>>>>>>>>>>>>>>>>>>>>>>>>
      SV40 late polyA 1660       1670       1680       1690       1700
                *    *    *    *    *    *    *    *    *    *
1651  TTAGTCGACCGAATTGGCCGCTCTAGACTCTAGCTGCAGAGGGACCTGCG  1700
                            >>>>>>>>>>>>>>>>>>>>>>>>>>>
                            Human Synapsin Promoter
      >>
      SV40 late polyA 1710       1720       1730       1740       1750
                *    *    *    *    *    *    *    *    *    *
1701  TATGAGTGCAAGTGGGTTTTAGGACCAGGATGAGGCGGGGTGGGGGTGCC  1750
      >>>>>>>>>>>>>>>>>>>>>>>>>>>>>>>>>>>>>>>>>>>>>>>>>>
      Human Synapsin Promoter 1760       1770       1780       1790       1800
                *    *    *    *    *    *    *    *    *    *
```

FIG. 6
CONTINUED

```
1751 TACCTGACGACCGACCCCGACCCACTGGACAAGCACCCAACCCCCATTCC 1800
     >>>>>>>>>>>>>>>>>>>>>>>>>>>>>>>>>>>>>>>>>>>>>>>>>>
     Human Synapsin Promoter 1810      1820      1830      1840      1850
          *    *    *    *    *    *    *    *    *    *
1801 CCAAATTGCGCATCCCCTATCAGAGAGGGGGAGGGGAAACAGGATGCGGC 1850
     >>>>>>>>>>>>>>>>>>>>>>>>>>>>>>>>>>>>>>>>>>>>>>>>>>
     Human Synapsin Promoter 1860      1870      1880      1890      1900
          *    *    *    *    *    *    *    *    *    *
1851 GAGGCGCGTGCGCACTGCCAGCTTCAGCACCGCGGACAGTGCCTTCGCCC 1900
     >>>>>>>>>>>>>>>>>>>>>>>>>>>>>>>>>>>>>>>>>>>>>>>>>>
     Human Synapsin Promoter 1910      1920      1930      1940      1950
          *    *    *    *    *    *    *    *    *    *
1901 CCGCCTGGCGGCGCGCGCCACCGCCGCCTCAGCACTGAAGGCGCGCTGAC 1950
     >>>>>>>>>>>>>>>>>>>>>>>>>>>>>>>>>>>>>>>>>>>>>>>>>>
     Human Synapsin Promoter 1960      1970      1980      1990      2000
          *    *    *    *    *    *    *    *    *    *
1951 GTCACTCGCCGGTCCCCCGCAAACTCCCCTTCCCGGCCACCTTGGTCGCG 2000
     >>>>>>>>>>>>>>>>>>>>>>>>>>>>>>>>>>>>>>>>>>>>>>>>>>
     Human Synapsin Promoter 2010      2020      2030      2040      2050
          *    *    *    *    *    *    *    *    *    *
2001 TCCGCGCCGCCGCCGGCCCAGCCGGACCGCACCACGCGAGGCGCGAGATA 2050
     >>>>>>>>>>>>>>>>>>>>>>>>>>>>>>>>>>>>>>>>>>>>>>>>>>
     Human Synapsin Promoter 2060      2070      2080      2090      2100
          *    *    *    *    *    *    *    *    *    *
2051 GGGGGGCACGGGCGCGACCATCTGCGCTGCGGCGCCGGCGACTCAGCGCT 2100
     >>>>>>>>>>>>>>>>>>>>>>>>>>>>>>>>>>>>>>>>>>>>>>>>>>
     Human Synapsin Promoter 2110      2120      2130      2140      2150
          *    *    *    *    *    *    *    *    *    *
2101 GCCTCAGTCTGCGGTGGGCAGCGGAGGAGTCGTGTCGTGCCTGAGAGCGC 2150
     >>>>>>>>>>>>>>>>>>>>>>>>>>>>>>>>>>>>>>>>>>>>>>>>>>
     Human Synapsin Promoter 2160      2170      2180      2190      2200
```

FIG. 6
CONTINUED

```
              *         *         *         *         *         *         *         *         *         *
2151 AGTCGAATTCAAGCTGCTAGCAAGGATCCACCGGTCACCATGCCCACCCC 2200
                                                   M   P   T   P
     >>>>>>                                        >>>>>>>>>>>>
     Human Synapsin Promoter                       tyrosine hydroxylase 2210      2220      2230      2240      2250
              *         *         *         *         *         *         *         *         *         *
2201 CGACGCCACCACGCCACAGGCCAAGGGCTTCCGCAGGGCCGTGTCTGAGC 2250
      D  A  T  T  P  Q  A  K  G  F  R  R  A  V  S  E  L
     >>>>>>>>>>>>>>>>>>>>>>>>>>>>>>>>>>>>>>>>>>>>>>>>>>
     tyrosine hydroxylase isoform a 2260      2270      2280      2290      2300
              *         *         *         *         *         *         *         *         *         *
2251 TGGACGCCAAGCAGGCAGAGGCCATCATGTCCCCGCGGTTCATTGGGCGC 2300
       D  A  K  Q  A  E  A  I  M  S  P  R  F  I  G  R
     >>>>>>>>>>>>>>>>>>>>>>>>>>>>>>>>>>>>>>>>>>>>>>>>>>
     tyrosine hydroxylase isoform a 2310      2320      2330      2340      2350
              *         *         *         *         *         *         *         *         *         *
2301 AGGCAGAGCCTCATCGAGGACGCCCGCAAGGAGCGGGAGGCGGCGGTGGC 2350
       R  Q  S  L  I  E  D  A  R  K  E  R  E  A  A  V  A
     >>>>>>>>>>>>>>>>>>>>>>>>>>>>>>>>>>>>>>>>>>>>>>>>>>
     tyrosine hydroxylase isoform a 2360      2370      2380      2390      2400
              *         *         *         *         *         *         *         *         *         *
2351 AGCAGCGGCCGCTGCAGTCCCCTCGGAGCCCGGGGACCCCCTGGAGGCTG 2400
       A  A  A  A  A  V  P  S  E  P  G  D  P  L  E  A  V
     >>>>>>>>>>>>>>>>>>>>>>>>>>>>>>>>>>>>>>>>>>>>>>>>>>
     tyrosine hydroxylase isoform a 2410      2420      2430      2440      2450
              *         *         *         *         *         *         *         *         *         *
2401 TGGCCTTTGAGGAGAAGGAGGGGAAGGCCGTGCTAAACCTGCTCTTCTCC 2450
        A  F  E  E  K  E  G  K  A  V  L  N  L  L  F  S
     >>>>>>>>>>>>>>>>>>>>>>>>>>>>>>>>>>>>>>>>>>>>>>>>>>
     tyrosine hydroxylase isoform a 2460      2470      2480      2490      2500
              *         *         *         *         *         *         *         *         *         *
2451 CCGAGGGCCACCAAGCCCTCGGCGCTGTCCCGAGCTGTGAAGGTGTTTGA 2500
       P  R  A  T  K  P  S  A  L  S  R  A  V  K  V  F  E
     >>>>>>>>>>>>>>>>>>>>>>>>>>>>>>>>>>>>>>>>>>>>>>>>>>
     tyrosine hydroxylase isoform a
```

FIG. 6
CONTINUED

```
              2510      2520      2530      2540      2550
                *    *    *    *    *    *    *    *    *    *
2501  GACGTTTGAAGCCAAAATCCACCATCTAGAGACCCGGCCCGCCCAGAGGC  2550
       T  F  E  A  K  I  H  H  L  E  T  R  P  A  Q  R  P
      >>>>>>>>>>>>>>>>>>>>>>>>>>>>>>>>>>>>>>>>>>>>>>>>>
      tyrosine hydroxylase isoform a 2560      2570      2580      2590      2600
                *    *    *    *    *    *    *    *    *    *
2551  CGCGAGCTGGGGGCCCCCACCTGGAGTACTTCGTGCGCCTCGAGGTGCGC  2600
        R  A  G  G  P  H  L  E  Y  F  V  R  L  E  V  R
      >>>>>>>>>>>>>>>>>>>>>>>>>>>>>>>>>>>>>>>>>>>>>>>>>
      tyrosine hydroxylase isoform a 2610      2620      2630      2640      2650
                *    *    *    *    *    *    *    *    *    *
2601  CGAGGGGACCTGGCCGCCCTGCTCAGTGGTGTGCGCCAGGTGTCAGAGGA  2650
        R  G  D  L  A  A  L  L  S  G  V  R  Q  V  S  E  D
      >>>>>>>>>>>>>>>>>>>>>>>>>>>>>>>>>>>>>>>>>>>>>>>>>
      tyrosine hydroxylase isoform a 2660      2670      2680      2690      2700
                *    *    *    *    *    *    *    *    *    *
2651  CGTGCGCAGCCCCGCGGGGCCCAAGGTCCCCTGGTTCCCAAGAAAAGTGT  2700
       V  R  S  P  A  G  P  K  V  P  W  F  P  R  K  V  S
      >>>>>>>>>>>>>>>>>>>>>>>>>>>>>>>>>>>>>>>>>>>>>>>>>
      tyrosine hydroxylase isoform a 2710      2720      2730      2740      2750
                *    *    *    *    *    *    *    *    *    *
2701  CAGAGCTGGACAAGTGTCATCACCTGGTCACCAAGTTCGACCCTGACCTG  2750
        E  L  D  K  C  H  H  L  V  T  K  F  D  P  D  L
      >>>>>>>>>>>>>>>>>>>>>>>>>>>>>>>>>>>>>>>>>>>>>>>>>
      tyrosine hydroxylase isoform a 2760      2770      2780      2790      2800
                *    *    *    *    *    *    *    *    *    *
2751  GACTTGGACCACCCGGGCTTCTCGGACCAGGTGTACCGCCAGCGCAGGAA  2800
       D  L  D  H  P  G  F  S  D  Q  V  Y  R  Q  R  R  K
      >>>>>>>>>>>>>>>>>>>>>>>>>>>>>>>>>>>>>>>>>>>>>>>>>
      tyrosine hydroxylase isoform a 2810      2820      2830      2840      2850
                *    *    *    *    *    *    *    *    *    *
2801  GCTGATTGCTGAGATCGCCTTCCAGTACAGGCACGGCGACCCGATTCCCC  2850
        L  I  A  E  I  A  F  Q  Y  R  H  G  D  P  I  P  R
```

FIG. 6
CONTINUED

>>>>>>>>>>>>>>>>>>>>>>>>>>>>>>>>>>>>>>>>>>>>>>>>>>
tyrosine hydroxylase isoform a

```
            2860      2870      2880      2890      2900
              *    *    *    *    *    *    *    *    *    *
2851 GTGTGGAGTACACCGCCGAGGAGATTGCCACCTGGAAGGAGGTCTACACC 2900
       V  E  Y  T  A  E  E  I  A  T  W  K  E  V  Y  T
```
>>>>>>>>>>>>>>>>>>>>>>>>>>>>>>>>>>>>>>>>>>>>>>>>>>
tyrosine hydroxylase isoform a

```
            2910      2920      2930      2940      2950
              *    *    *    *    *    *    *    *    *    *
2901 ACGCTGAAGGGCCTCTACGCCACGCACGCCTGCGGGGAGCACCTGGAGGC 2950
      T  L  K  G  L  Y  A  T  H  A  C  G  E  H  L  E  A
```
>>>>>>>>>>>>>>>>>>>>>>>>>>>>>>>>>>>>>>>>>>>>>>>>>>
tyrosine hydroxylase isoform a

```
            2960      2970      2980      2990      3000
              *    *    *    *    *    *    *    *    *    *
2951 CTTTGCTTTGCTGGAGCGCTTCAGCGGCTACCGGGAAGACAATATCCCCC 3000
      F  A  L  L  E  R  F  S  G  Y  R  E  D  N  I  P  Q
```
>>>>>>>>>>>>>>>>>>>>>>>>>>>>>>>>>>>>>>>>>>>>>>>>>>
tyrosine hydroxylase isoform a

```
            3010      3020      3030      3040      3050
              *    *    *    *    *    *    *    *    *    *
3001 AGCTGGAGGACGTCTCCCGCTTCCTGAAGGAGCGCACGGGCTTCCAGCTG 3050
       L  E  D  V  S  R  F  L  K  E  R  T  G  F  Q  L
```
>>>>>>>>>>>>>>>>>>>>>>>>>>>>>>>>>>>>>>>>>>>>>>>>>>
tyrosine hydroxylase isoform a

```
            3060      3070      3080      3090      3100
              *    *    *    *    *    *    *    *    *    *
3051 CGGCCTGTGGCCGGCCTGCTGTCCGCCCGGGACTTCCTGGCCAGCCTGGC 3100
      R  P  V  A  G  L  L  S  A  R  D  F  L  A  S  L  A
```
>>>>>>>>>>>>>>>>>>>>>>>>>>>>>>>>>>>>>>>>>>>>>>>>>>
tyrosine hydroxylase isoform a

```
            3110      3120      3130      3140      3150
              *    *    *    *    *    *    *    *    *    *
3101 CTTCCGCGTGTTCCAGTGCACCCAGTATATCCGCCACGCGTCCTCGCCCA 3150
      F  R  V  F  Q  C  T  Q  Y  I  R  H  A  S  S  P  M
```
>>>>>>>>>>>>>>>>>>>>>>>>>>>>>>>>>>>>>>>>>>>>>>>>>>
tyrosine hydroxylase isoform a

```
3151 TGCACTCCCCTGAGCCGGACTGCTGCCACGAGCTGCTGGGGCACGTGCCC 3200
      H  S  P  E  P  D  C  C  H  E  L  L  G  H  V  P
     >>>>>>>>>>>>>>>>>>>>>>>>>>>>>>>>>>>>>>>>>>>>>>>>>>
     tyrosine hydroxylase isoform a 3210      3220      3230      3240      3250
              *    *    *    *    *    *    *    *    *    *
3201 ATGCTGGCCGACCGCACCTTCGCGCAGTTCTCGCAGGACATTGGCCTGGC 3250
      M  L  A  D  R  T  F  A  Q  F  S  Q  D  I  G  L  A
     >>>>>>>>>>>>>>>>>>>>>>>>>>>>>>>>>>>>>>>>>>>>>>>>>>
     tyrosine hydroxylase isoform a 3260      3270      3280      3290      3300
              *    *    *    *    *    *    *    *    *    *
3251 GTCCCTGGGGGCCTCGGATGAGGAAATTGAGAAGCTGTCCACGCTGTACT 3300
      S  L  G  A  S  D  E  E  I  E  K  L  S  T  L  Y  W
     >>>>>>>>>>>>>>>>>>>>>>>>>>>>>>>>>>>>>>>>>>>>>>>>>>
     tyrosine hydroxylase isoform a 3310      3320      3330      3340      3350
              *    *    *    *    *    *    *    *    *    *
3301 GGTTCACGGTGGAGTTCGGGCTGTGTAAGCAGAACGGGGAGGTGAAGGCC 3350
      F  T  V  E  F  G  L  C  K  Q  N  G  E  V  K  A
     >>>>>>>>>>>>>>>>>>>>>>>>>>>>>>>>>>>>>>>>>>>>>>>>>>
     tyrosine hydroxylase isoform a 3360      3370      3380      3390      3400
              *    *    *    *    *    *    *    *    *    *
3351 TATGGTGCCGGGCTGCTGTCCTCCTACGGGGAGCTCCTGCACTGCCTGTC 3400
      Y  G  A  G  L  L  S  S  Y  G  E  L  L  H  C  L  S
     >>>>>>>>>>>>>>>>>>>>>>>>>>>>>>>>>>>>>>>>>>>>>>>>>>
     tyrosine hydroxylase isoform a 3410      3420      3430      3440      3450
              *    *    *    *    *    *    *    *    *    *
3401 TGAGGAGCCTGAGATTCGGGCCTTCGACCCTGAGGCTGCGGCCGTGCAGC 3450
      E  E  P  E  I  R  A  F  D  P  E  A  A  A  V  Q  P
     >>>>>>>>>>>>>>>>>>>>>>>>>>>>>>>>>>>>>>>>>>>>>>>>>>
     tyrosine hydroxylase isoform a 3460      3470      3480      3490      3500
              *    *    *    *    *    *    *    *    *    *
3451 CCTACCAAGACCAGACGTACCAGTCAGTCTACTTCGTGTCTGAGAGCTTC 3500
      Y  Q  D  Q  T  Y  Q  S  V  Y  F  V  S  E  S  F
     >>>>>>>>>>>>>>>>>>>>>>>>>>>>>>>>>>>>>>>>>>>>>>>>>>
     tyrosine hydroxylase isoform a
```

FIG. 6
CONTINUED

```
            3510      3520      3530      3540      3550
              *    *    *    *    *    *    *    *    *    *
3501 AGTGACGCCAAGGACAAGCTCAGGAGCTATGCCTCACGCATCCAGCGCCC 3550
       S  D  A  K  D  K  L  R  S  Y  A  S  R  I  Q  R  P
     >>>>>>>>>>>>>>>>>>>>>>>>>>>>>>>>>>>>>>>>>>>>>>>>>>
     tyrosine hydroxylase isoform a 3560      3570      3580      3590      3600
              *    *    *    *    *    *    *    *    *    *
3551 CTTCTCCGTGAAGTTCGACCCGTACACGCTGGCCATCGACGTGCTGGACA 3600
       F  S  V  K  F  D  P  Y  T  L  A  I  D  V  L  D  S
     >>>>>>>>>>>>>>>>>>>>>>>>>>>>>>>>>>>>>>>>>>>>>>>>>>
     tyrosine hydroxylase isoform a 3610      3620      3630      3640      3650
              *    *    *    *    *    *    *    *    *    *
3601 GCCCCCAGGCCGTGCGGCGCTCCCTGGAGGGTGTCCAGGATGAGCTGGAC 3650
       P  Q  A  V  R  R  S  L  E  G  V  Q  D  E  L  D
     >>>>>>>>>>>>>>>>>>>>>>>>>>>>>>>>>>>>>>>>>>>>>>>>>>
     tyrosine hydroxylase isoform a 3660      3670      3680      3690      3700
              *    *    *    *    *    *    *    *    *    *
3651 ACCCTTGCCCATGCGCTGAGTGCCATTGGCTAACTAGTGGATCCGTCGAC 3700
       T  L  A  H  A  L  S  A  I
     >>>>>>>>>>>>>>>>>>>>>>>>>>>>>>>>>             >>>>>>>
     tyrosine hydroxylase isoform a                WPRE 3710      3720      3730      3740      3750
              *    *    *    *    *    *    *    *    *    *
3701 AATCAACCTCTGGATTACAAAATTTGTGAAAGATTGACTGGTATTCTTAA 3750
     >>>>>>>>>>>>>>>>>>>>>>>>>>>>>>>>>>>>>>>>>>>>>>>>>>
     WPRE 3760      3770      3780      3790      3800
              *    *    *    *    *    *    *    *    *    *
3751 CTATGTTGCTCCTTTTACGCTATGTGGATACGCTGCTTTAATGCCTTTGT 3800
     >>>>>>>>>>>>>>>>>>>>>>>>>>>>>>>>>>>>>>>>>>>>>>>>>>
     WPRE 3810      3820      3830      3840      3850
              *    *    *    *    *    *    *    *    *    *
3801 ATCATGCTATTGCTTCCCGTATGGCTTTCATTTTCTCCTCCTTGTATAAA 3850
     >>>>>>>>>>>>>>>>>>>>>>>>>>>>>>>>>>>>>>>>>>>>>>>>>>
     WPRE
```

FIG. 6
CONTINUED

```
              3860      3870      3880      3890      3900
                *         *         *         *         *
3851  TCCTGGTTGCTGTCTCTTTATGAGGAGTTGTGGCCCGTTGTCAGGCAACG  3900
      >>>>>>>>>>>>>>>>>>>>>>>>>>>>>>>>>>>>>>>>>>>>>>>>>>
      WPRE
              3910      3920      3930      3940      3950
                *         *         *         *         *
3901  TGGCGTGGTGTGCACTGTGTTTGCTGACGCAACCCCCACTGGTTGGGGCA  3950
      >>>>>>>>>>>>>>>>>>>>>>>>>>>>>>>>>>>>>>>>>>>>>>>>>>
      WPRE
              3960      3970      3980      3990      4000
                *         *         *         *         *
3951  TTGCCACCACCTGTCAGCTCCTTTCCGGGACTTTCGCTTTCCCCCTCCCT  4000
      >>>>>>>>>>>>>>>>>>>>>>>>>>>>>>>>>>>>>>>>>>>>>>>>>>
      WPRE
              4010      4020      4030      4040      4050
                *         *         *         *         *
4001  ATTGCCACGGCGGAACTCATCGCCGCCTGCCTTGCCCGCTGCTGGACAGG  4050
      >>>>>>>>>>>>>>>>>>>>>>>>>>>>>>>>>>>>>>>>>>>>>>>>>>
      WPRE
              4060      4070      4080      4090      4100
                *         *         *         *         *
4051  GGCTCGGCTGTTGGGCACTGACAATTCCGTGGTGTTGTCGGGGAAGCTGA  4100
      >>>>>>>>>>>>>>>>>>>>>>>>>>>>>>>>>>>>>>>>>>>>>>>>>>
      WPRE
              4110      4120      4130      4140      4150
                *         *         *         *         *
4101  CGTCCTTTCCATGGCTGCTCGCCTGTGTTGCCACCTGGATTCTGCGCGGG  4150
      >>>>>>>>>>>>>>>>>>>>>>>>>>>>>>>>>>>>>>>>>>>>>>>>>>
      WPRE
              4160      4170      4180      4190      4200
                *         *         *         *         *
4151  ACGTCCTTCTGCTACGTCCCTTCGGCCCTCAATCCAGCGGACCTTCCTTC  4200
      >>>>>>>>>>>>>>>>>>>>>>>>>>>>>>>>>>>>>>>>>>>>>>>>>>
      WPRE
              4210      4220      4230      4240      4250
                *         *         *         *         *
4201  CCGCGGCCTGCTGCCGGCTCTGCGGCCTCTTCCGCGTCTTCGCCTTCGCC  4250
      >>>>>>>>>>>>>>>>>>>>>>>>>>>>>>>>>>>>>>>>>>>>>>>>>>
      WPRE
```

FIG. 6
CONTINUED

```
            *         *         *         *         *         *         *         *         *         *
4251 CTCAGACGAGTCGGATCTCCCTTTGGGCCGCCTCCCCGCCTGGAATTCGA 4300
     >>>>>>>>>>>>>>>>>>>>>>>>>>>>>>>>>>>>>>>>>>>>>>>>>>
     WPRE
              4310      4320      4330      4340      4350
                *         *         *         *         *
4301 GCTCGGTACAGCTTATCGATACCGTCGACTTCGAGCAACTTGTTTATTGC 4350
     >>>                          >>>>>>>>>>>>>>>>>>>>>
     WPRE                         SV40 pA
              4360      4370      4380      4390      4400
                *         *         *         *         *
4351 AGCTTATAATGGTTACAAATAAAGCAATAGCATCACAAATTTCACAAATA 4400
     >>>>>>>>>>>>>>>>>>>>>>>>>>>>>>>>>>>>>>>>>>>>>>>>>>
     SV40 pA
              4410      4420      4430      4440      4450
                *         *         *         *         *
4401 AAGCATTTTTTTCACTGCATTCTAGTTGTGGTTTGTCCAAACTCATCAAT 4450
     >>>>>>>>>>>>>>>>>>>>>>>>>>>>>>>>>>>>>>>>>>>>>>>>>>
     SV40 pA
              4460      4470      4480      4490      4500
                *         *         *         *         *
4451 GTATCTTATCATGTCTGGATCGTCTAGCATCGAAGATCCCCCGATCTGAG 4500
                                          <<
                                          AAV ITR
     >>>>>>>>>>>>>>>>>>>>>>>>>>>>>>>>>>>
     SV40 pA
              4510      4520      4530      4540      4550
                *         *         *         *         *
4501 GAACCCCTAgtgatggagttggccactccctctctgcgcgctcgctcgct 4550
     <<<<<<<<<<<<<<<<<<<<<<<<<<<<<<<<<<<<<<<<<<<<<<<<<<
     AAV ITR
              4560      4570      4580      4590      4600
                *         *         *         *         *
4551 cactgaggccgcccgggcaaagcccgggcgtcgggcgacctttggtcgcc 4600
     <<<<<<<<<<<<<<<<<<<<<<<<<<<<<<<<<<<<<<<<<<<<<<<<<<
     AAV ITR
              4610      4620      4630      4640
                *         *         *         *
4601 cggcctcagtgagcgagcgagcgcgcagagagggagtggccaa 4643
     <<<<<<<<<<<<<<<<<<<<<<<<<<<<<<<<<<<<<<<<<<<
     AAV ITR
```

FIG. 6
CONTINUED

VIRAL VECTOR CONSTRUCT FOR NEURON SPECIFIC OPTIMIZED CONTINUOUS DOPA SYNTHESIS IN VIVO

CROSS-REFERENCE TO RELATED APPLICATIONS

The present application is a Continuation of U.S. patent application Ser. No. 13/505,879, filed Aug. 6, 2012, which is a 35 U.S.C. §371 National Stage of International Application No. PCT/EP2010/067155, filed Nov. 9, 2010, which claims the benefit of and priority to U.S. Provisional Application No. 61/259,502, filed Nov. 9, 2009, the contents of each of which is hereby incorporated by reference in its entirety.

In accordance with 37 CFR 1.52(e)(5), a Sequence Listing in the form of a text file (entitled "2006685-0482_ST25", created on Dec. 3, 2015, and having a size of 62,242 bytes) is incorporated herein by reference in its entirety.

FIELD OF INVENTION

The present invention relates to viral vector constructs especially single rAAV vector constructs comprising polynucleotide sequences encoding two polypeptides to be differentially expressed in a target cell. The invention also relates to pharmaceutical compositions comprising said vector and the delivery into human brain tissue and to the medical use of said vector for the treatment of diseases associated with catecholamine dysfunction. In particular the invention relates to the treatment of diseases associated with dopamine deficiency, such as Parkinson's disease and related disorders.

BACKGROUND OF INVENTION

Parkinson's disease is affecting people from 30 years of age and older. Mean age at onset is approx. 60 years. The major clinical symptoms are rigidity, bradykinesia and resting tremor. In addition the disease can show a range of other symptoms such as hypotension, cognitive impairment, postural instability, and many more.

The disease is primarily a basal ganglia disorder caused by degeneration of the nigrostriatal dopaminergic system in the brain (nerve cells using dopamine (DA) as their signaling substance, located in the substantia nigra of the brain stem projecting to the putamen and caudate nucleus). The disorder is progressive over many years.

The current treatment standard is based on substitution of dopamine by addition of L-dopa (which is converted to dopamine in the brain), or other dopamine-receptor stimulating agents. Although current treatment strategies aimed at substitution of the dopamine deficiency are often very efficient in the early phase of the disease (up to 7-10 years), eventually most patients start to experience diminishing treatment response and increasing adverse events. The most problematic of these is the L-dopa-induced dyskinesias that appear as a result of treatment with the current drug-of-choice, L-dopa, or dopamine agonists. Since patients with Parkinson's disease tend to live longer and longer with their disease, due to improved treatments in recent years, the L-dopa induced dyskinesia poses an increasing problem especially for patients with early onset of the disease. There are today few treatment options for dyskinesias, and these are often complicated and the access is limited.

One approach that has been tested in preclinical animal models of Parkinson's disease is to refine the classical pharmacological dopamine replacement strategy by using a gene therapy approach to obtain a local dopamine replacement in the putamen and caudate nucleus where the dopamine deficiency is most advanced. This approach is called the "enzyme replacement strategy". The rationale for this treatment stems from clinical observations in Parkinson's disease (PD) patients, which suggested that severe abnormal involuntary movements (i.e., dyskinesias), induced by oral L-DOPA medication, could be alleviated by L-DOPA or DA agonists infused either via the intravenous or duodenal route. Thus, the current hypothesis is that dyskinesias develop, at least in part, due to the intermittent, pulsatile supply of DA that the oral L-DOPA delivery paradigm gives rise to. These patients benefit from continuous DA stimulation also by dramatic reduction in total time spent in "off" state.

Three different enzymes are necessary for the production of dopamine, namely tyrosine hydroxylase (TH), GTP-cyclohydrolase 1 (GCH1) and aromatic amino acid decarboxylase (AADC). The two first regulate the production of L-DOPA from tyrosine (a dietary amino acid) while AADC converts L-DOPA to dopamine. None of these enzymes are unique to dopaminergic neurons but may also be present in non-dopaminergic cells. The addition of these enzymes to the denervated target area can result in production of L-DOPA or dopamine locally. The advantage of this strategy may be that it provides a constant production of L-DOPA in relative to the conventional oral therapies where the L-DOPA plasma levels (and also brain levels) are fluctuating. It also localizes the treatment to the brain area in need for substitution while other parts of the body are not "treated" resulting in a favourable effect versus side effect-ratio.

Published preclinical data using this approach have provided the following observations:

1. Expression of all three genes can be obtained in the putamen and caudate nucleus by transduction using multiple rAAV vectors [Kaplitt M G, et al: Long-term gene expression and phenotypic correction using adeno-associated virus vectors in the mammalian brain; *Nat Genet.* 1994 8 148-54; Mandel R J, et al: Characterization of intrastriatal recombinant adeno-associated virus-mediated gene transfer of human tyrosine hydroxylase and human GTP-cyclohydrolase I in a rat model of Parkinson's disease; *J Neurosci* 1998 18 4271-84; Shen Y, et al: Triple transduction with adeno-associated virus vectors expressing tyrosine hydroxylase, aromatic-L-amino-acid decarboxylase, and GTP cyclohydrolase I for gene therapy of Parkinson's disease; *Hum Gene Ther* 2000 11 1509-19].

2. The efficiency of TH is dependent on GCH1 (which produces the co-factor tetrahydrobiopterin, BH4). Mandel and collaborators have shown this by measuring levels of L-dopa using micro dialysis [Mandel R J, et al: Characterization of intrastriatal recombinant adeno-associated virus-mediated gene transfer of human tyrosine hydroxylase and human GTP-cyclohydrolase I in a rat model of Parkinson's disease; *J Neurosci* 1998 18 4271-84].

3. In a monkey model of Parkinson's disease (the MPTP-model) expression of AADC can result in more efficient conversion of oral L-dopa and through this mechanism improve function in a monkey UPDRS motor score (UPDRS is the standard clinical evaluation scale for Parkinson symptoms) [Bankiewicz K S, et al: Long-term clinical improvement in MPTP-lesioned primates after gene therapy with AAV-hAADC; *Mol Ther* 2006 14 564-70].

4. Expression of all three genes can result in improved function in both rat models [Shen Y, et al: Triple transduction with adeno-associated virus vectors expressing tyrosine hydroxylase, aromatic-L-aminoacid decarboxylase, and GTP cyclohydrolase I for gene therapy of Parkinson's disease; *Hum Gene Ther* 2000 11 1509-19] and monkey models [Muramatsu S, et al: Behavioral recovery in a primate model of Parkinson's disease by triple transduction of striatal cells with adeno-associated viral vectors expressing dopamine-synthesizing enzymes. *Hum Gene Ther* 2002 13 345-54] of Parkinson's disease].

5. Expression of TH and GCH1 is sufficient to obtain striatal L-dopa levels that can result in functional improvement in a rat model of Parkinson's disease and can furthermore significantly reduce the L-dopa induced dyskinesia [Kirik D, et al: Reversal of motor impairments in parkinsonian rats by continuous intrastriatal delivery of L-dopa using rAAV-mediated gene transfer; *Proc Natl Acad Sci* 2002 99 4708-13; Carlsson et al: Reversal of dyskinesias in an animal model of Parkinson's disease by continuous L-DOPA delivery using rAAV vectors; *Brain* 2005 128 559-69]. However, these studies were conducted using two separate AAV serotype 2 vectors each containing either the GCH1 gene or the TH gene, both under the control of a large synthetic promoter (chicken b-actin promoter containing a rabbit gamma-globulin intron, preceded with an enhancer element from the cytomegalovirus promoter, termed as the chicken b-actin, CBA, promoter). As such, there was no possible way to control the expression ratio of the two genes at a cellular level; nor did the promoter enable expression limited to neurons.

In respect of the current state of the art within the field of the present invention, Sun et al (2004), describes a non-AAV viral expression vector with two transcriptional units, each regulated by a neuron-specific promoter. It does not describe the relative level of transcription of the two units. In vitro there is comparable amounts of cells expressing TH and GCH-1 when transduced with both the 3-gene and the 4-gene vector. In both cases TH and GCH-1 are on different transcripts. In the 4-gene vector GCH-1 is translated from an IRES site (after the VMAT-2 ORF).

Shen et al 2000 describes co-transduction of HEK-293 cells with AAV-TH, AAV-AADC and AAV-GCH-1. In a titration study, 293 cells were transduced with AAV-TH and AAV-AADC and varying amounts of AAV-GCH-1. The results show an increase in both L-dopa and dopamine with increasing titer of AAV-GCH-1. AAVGCH-1 was tested in titers up to the same as for AAV-TH. The described ratios are 1:10, 1:2 and 1:1 (AAV-GCH-1:AAV-TH). In vivo gene therapy was conducted with a 1:1 ratio of the two vectors (with and without AAV-AADC).

Kirk et al, 2002 and Carlsson et al 2005 describe co-administration of a 1:1 mix of AAV-TH and AAVGCH1, in which the titer of AAV-TH is approximately 3.5 times that of AAV-GCH-1 (ratio of 1:3.5). Neither of these references states why this ratio was used.

U.S. Pat. No. 7,419,829 (Oxford Biomedica) describes a mutated WPRE element and its use in a three-gene vector (EIAV) with TH, AADC, and GCH-1 separated by IRES sequences. The WPRE element with enhance the expression of the three genes to the same extent.

WO 96/05319 (Arch Development) describes dicistronic vectors with either an IRES site or the promoter in the 5' retroviral LTR, which controls expression of both an upstream and a downstream cistron. In a double transduction experiment with fibroblasts, they disclose a TH activity of 242.6 pmol/mg/min and a GCH1 activity of 35.8 pmol/mg/min. This translates into a ratio of 1:6.8 between the two enzymes on an activity basis. In addition the reference describes an optimum BH4 concentration (500 QM) in order to achieve maximum TH activity. L-DOPA concentration in TH-transduced cells was maximum beyond 50 QM BH4 and did not increase further with higher concentrations of BH4.

None of the mentioned references describe an AAV vector with a construct coding for both TH and GCH-1. All the one-vector systems in the prior art coding for both TH and GCH-1 have been made in viral vectors that include much larger pieces of nucleic acid. Most of the one-vector systems of the prior art additionally comprise an expression construct coding for AADC. AAV vectors present advantages over the one vector systems based on HSV, EIAV and Retrovirus for clinical purposes. In addition, the absence of AADC is also an advantage over the prior art since this leads to generation of L-DOPA in the transduced cells instead of DA.

SUMMARY OF INVENTION

The purpose of the present invention has been to develop new molecular tools for the treatment of disorders where the present treatment strategies are insufficient or where present treatment is associated with severe side effects and/or where the treated individual develops resistance against said treatment. More specifically, the present invention relates to a novel expression construct regulating the level of enzymes involved in catecholamine biosynthesis, thus being useful in a method for restoring a normal catecholamine balance in a subject in need thereof.

In particular the invention relates to use of said expression construct in a method of treatment of neurological disorders, preferably non-curable degenerative neurological disorders wherein the majority of the patients experience diminishing treatment response and increased adverse events during prolonged treatment.

The present invention relates primarily to the treatment of Parkinson's disease, wherein the present treatment strategy involves the administration of L-DOPA or other dopamine receptor stimulating agents. The present treatment is efficient, particularly in the early phase of the disease, but during prolonged treatment most patients develop L-DOPA induced dyskinesia. Development of dyskenesia is believed to be associated with non-continuous delivery of L-DOPA or other dopamine receptor stimulating agents. It is a major object of the present invention to refine the present treatment by supplying the compounds necessary for treatment of particularly Parkinson's disease locally where needed and at continuous rates that diminishes any adverse effects.

The present invention relates to a one-vector expression system, comprising two polynucleotides encoding two polypeptides, to be administered locally in the central nervous system, wherein said vector expression system is capable of differentially expressing the two encoded polypeptides in order obtain the exact proportion of the expressed polypeptides necessary for the optimal treatment of a given neurological disorder.

In a first aspect, the present invention relates to a one-vector expression system comprising
a) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, with the proviso that said vector does not comprise a nucleotide sequence encoding an aromatic amino acid decarboxylase (AADC) polypeptide, or b) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, wherein the vector is an adeno associated vector (AAV), or c) an expression cassette comprising a promoter, a first nucleotide sequence, a translation initiating nucleotide sequence such as an internal ribosome entry site (IRES) and a second nucleotide sequence, wherein said promoter is operably linked to said first nucleotide sequence, and wherein said translation initiating nucleotide sequence is links said first and said second nucleotide sequence, wherein said first nucleotide sequence encodes a GTP-cyclohydrolase 1 (GCH1) polypeptide or a biologically active fragment or variant thereof, and wherein said second nucleotide sequence encodes a tyrosine hydroxylase (TH) polypeptide or a biologically active fragment or variant thereof, or d) an expression cassette comprising a first nucleotide sequence, a translation initiating nucleotide sequence such as an internal ribosome entry site (IRES) and a second nucleotide sequence wherein said translation initiating nucleotide sequence links said first and said second nucleotide sequence, and wherein the sequence comprising said first nucleotide sequence linked to said translation initiating nucleotide sequence linked to said second nucleotide sequence is flanked by 5' and 3' terminal repeats, and wherein said first nucleotide sequence encodes a GTP-cyclohydrolase 1 (GCH1) polypeptide or a biologically active fragment or variant thereof, and wherein said second nucleotide sequence encodes a tyrosine hydroxylase (TH) polypeptide or a biologically active fragment or variant thereof, wherein said terminal repeats comprises a sequence capable of directing the expression of an operably linked polypeptide.

In another aspect, the invention relates to a one-vector expression system comprising a) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, wherein said polypeptide or a biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14, with the proviso that said vector does not comprise a nucleotide sequence encoding an aromatic amino acid decarboxylase (AADC) polypeptide, or b) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, wherein said polypeptide or a biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14, wherein the vector is an adeno associated vector (AAV), or c) an expression cassette comprising a promoter, a first nucleotide sequence, a translation initiating nucleotide sequence such as an internal ribosome entry site (IRES) and a second nucleotide sequence, wherein said promoter is operably linked to said first nucleotide sequence, and wherein said translation initiating nucleotide sequence links said first and said second nucleotide sequence, wherein said first nucleotide sequence encodes a GTP-cyclohydrolase 1 (GCH1) polypeptide or a biologically active fragment or variant thereof, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5, SEQ ID NO. 6, and wherein said second nucleotide sequence encodes a tyrosine hydroxylase (TH) polypeptide or a biologically active fragment or variant thereof, wherein said polypeptide or a biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, or d) an expression cassette comprising a first nucleotide sequence, a translation initiating nucleotide sequence such as an internal ribosome entry site (IRES) and a second nucleotide sequence wherein said translation initiating nucleotide sequence links said first and said second nucleotide sequence, and wherein the sequence comprising said first nucleotide sequence linked to said translation initiating nucleotide sequence linked to said second nucleotide sequence is flanked by 5' and 3' terminal repeats, and wherein said first nucleotide sequence encodes a GTP-cyclohydrolase 1 (GCH1) polypeptide or a biologically active fragment or variant thereof, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said second nucleotide sequence encodes a tyrosine hydroxylase (TH) polypeptide or a biologically active fragment or variant thereof, wherein said polypeptide or a biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, wherein said terminal repeats comprise a sequence capable of directing the expression of an operably linked polypeptide.

In certain embodiments, the vector can be an adeno-associated viral vector (AAV). In preferred embodiments, the invention comprises regulatory elements, such as Woodchuck hepatitis virus post-transcriptional regulatory element (WPRE), within the vector construct in order to regulate the differentiated expression of the encoded polypeptides. In certain embodiments, differential expression of the polypeptides can be advantageous for the continuous flow of DOPA for intended treatment of Parkinson's disease. It can also be advantageous for said vector to be functional in mammalian cells, preferably neuronal cells.

A one-vector construct, wherein it is possible to differentially express two or more polypeptide-encoding polynucleotides may also be useful for other applications such as treatment of other disorders, wherein a specific stoichiometry between two or more polypeptides is desired.

In another aspect the invention relates to a method for determining the expression ratio of GTP cyclohydroxylase1 polypeptide (SEQ ID NOs. 1, 2, 3, 4, 5 and 6) and tyrosine hydroxylase polypeptide (SEQ ID NOs. 7, 8, 9, 10, 11, 12, 13 and 14), respectively, or variants thereof, said polypeptide encoded by the vector as defined herein, comprising measuring the:
  a. enzymatic activity of the polypeptides, or
  b. amount of $BH_4$ produced, or
  c. amount expressed of said polypeptides, or
  d. level of transcribed mRNA corresponding to the polypeptides of GTP cyclohydroxylase1 polypeptide and tyrosine hydroxylase, respectively.

In certain embodiments of the present invention, the ratio is preferably measured by determining the amount of expressed mRNA, more preferably by determining the amount of protein expressed or by determining the activity of the expressed TH (tyrosine hydroxylase) and GCH1 (GTP cyclohydroxylase1 polypeptide) enzymes. The ratio of the expressed TH and GCH1 enzymes is between 15:1 to 1:1, preferably between 10:1 to 3:1, more preferably between 8:1 and 3:1, more preferably between 7:1 and 4:1, such as between 7:1 and 5:1, e.g. 6:1. (Detailed in FIG. 3).

In another aspect, the invention relates to an isolated host cell comprising the vector as defined herein above.

In further aspects the invention relates to medical uses of the vector expression system of the invention, the polynucleotide of the vector and the encoded polypeptide.

Preferably the medical use is for the treatment of a disease, a disorder or damage of the nervous system, more preferably for the treatment of degenerative neurological disorders such as Parkinson's disease.

In further aspects the invention relates to an isolated host cell transformed or transduced with the vector of the invention and to a packaging cell line capable of producing an infective virion of the invention.

In one aspect the vector of the present invention, is used as a medicament.

Furthermore, the invention relates to a pharmaceutical composition comprising the vector as defined herein above and a pharmaceutically acceptable carrier or diluent.

In one aspect the pharmaceutical composition is for use in a method of treatment of Parkinson's Disease, said composition comprising a one-vector expression system and a formulation for delivering said vector to the basal ganglia, wherein said one-vector expression system comprises
  a) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, with the proviso that said vector does not comprise a nucleotide sequence encoding an aromatic amino acid decarboxylase (AADC) polypeptide, or
  b) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, wherein the vector is an adeno associated vector (AAV), or
  c) an expression cassette comprising a promoter, a first nucleotide sequence, a translation initiating nucleotide sequence such as an internal ribosome entry site (IRES) and a second nucleotide sequence, wherein said promoter is operably linked to said first nucleotide sequence, and wherein said translation initiating nucleotide sequence is linking said first and said second nucleotide sequence, wherein said first nucleotide sequence encodes a GTP-cyclohydrolase 1 (GCH1) polypeptide or a biologically active fragment or variant thereof, and wherein said second nucleotide sequence encodes a tyrosine hydroxylase (TH) polypeptide or a biologically active fragment or variant thereof, or
  d) an expression cassette comprising a first nucleotide sequence, a translation initiating nucleotide sequence such as an internal ribosome entry site (IRES) and a second nucleotide sequence wherein said translation initiating nucleotide sequence is linking said first and said second nucleotide sequence, and wherein the sequence comprising said first nucleotide sequence linked to said translation initiating nucleotide sequence linked to said second nucleotide sequence is flanked by 5' and 3' terminal repeats, and wherein said first nucleotide sequence encodes a GTP-cyclohydrolase 1 (GCH1) polypeptide or a biologically active fragment or variant thereof, and wherein said second nucleotide sequence encodes a tyrosine hydroxylase (TH) polypeptide or a biologically active fragment or variant thereof, wherein said terminal repeats comprises a sequence capable of directing the expression of an operably linked polypeptide.

In another aspect, the invention relates to a method of administering the pharmaceutical composition of the invention, wherein said pharmaceutical composition is administered by injection, orally through e.g. a tablet, by a spray, cutaneously or by inhalation. Said injection is preferably intracranial, intracerebral, intravitreous, intranasal, intravenous, intramuscular, intraspinal, intraperitoneal, subcutaneous or a bolus or continuous injection.

Also provided is a kit, comprising the pharmaceutical composition of the invention, said kit also comprising instructions for administering the pharmaceutical composition of the invention.

DESCRIPTION OF THE DRAWINGS

FIG. 6: Vector map with the construct of one embodiment of the present invention. FIG. 6 illustrates the nucleic acid sequence (top line of text; SEQ ID NO: 23) and corresponding amino acid sequence for each open reading frame (bottom line) of an exemplary portion of a vector construct which may be used in the one-vector expression system of the current invention.

DEFINITIONS

Figure 1A:
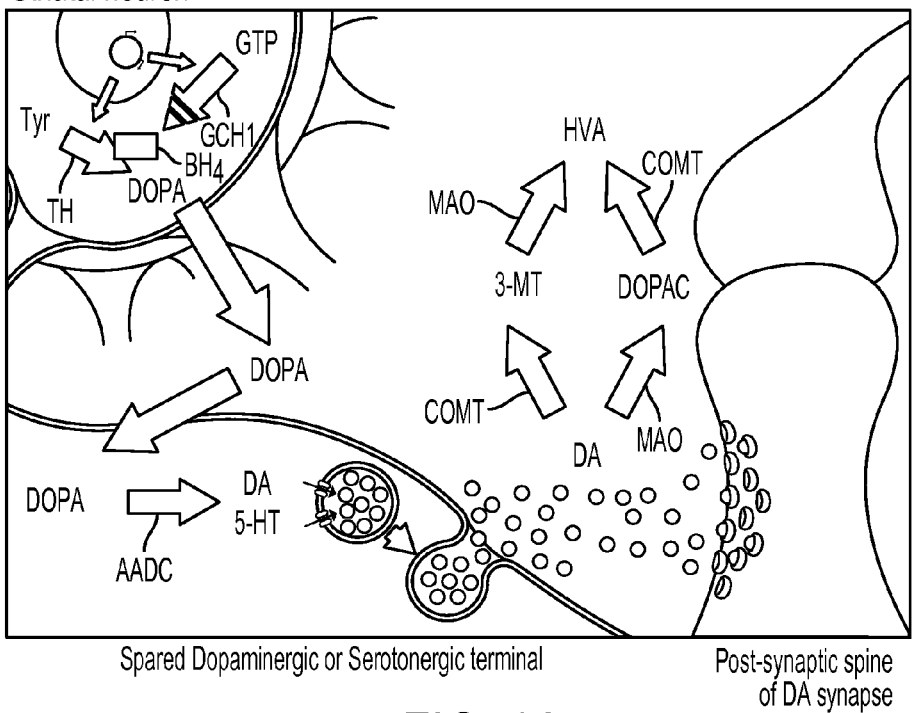
FIG. 1: (A) Overview of a continuous DOPA-delivery strategy of the present invention. (B) Comparative example using a traditional two-vector system lacking the possibility to control the relative expression levels of GCH and TH.

Agonist: The term 'agonist' used herein refers to a drug that binds to a receptor of a cell and triggers a response by the cell.

Biologically active: The term 'biologically active' when used herein in connection with enzymes encoded by the vector construct of the invention, refers to the enzymatic activity of said enzymes, meaning the capacity to catalyze a certain enzymatic reaction.

In particular biologic activity refers to the enzymatic activity of tyrosine hydroxylase (TH) and GTP-cyclohydrolase (GCH-1).

Biologically active fragment: The term "biologically active fragment" as used herein, refers to a part of a polypeptide, including enzymes, sharing the biological activity of the full length polypeptide. The biological activity of the fragment may be smaller than, larger than, or equal to the enzymatic activity of the native full length polypeptide.

Biologically active variant: The term "biologically active variant" as used herein, refers to a polypeptide part of a protein, such as an enzyme, having the same biological activity as a native full length protein. The biological activity of the fragment may be smaller than, larger than or equal to the enzymatic activity of the native full length polypeptide.

Catecholamine dysfunction: The term catecholamine dysfunction as used herein refers to abnormalities in catecholamine synthesis, regulation, storage, release, uptake or metabolism as compared to the same parameters in a healthy individual. In particular the catecholamine dysfunction is dopamine dysfunction, such as dopamine deficiency. The person skilled in the art is capable of diagnosing catecholamine dysfunction.

Cognitive impairment: The term 'cognitive impairment' used herein refers to a condition with poor mental function, associated with confusion, forgetfulness and difficulty concentrating.

Conservative substitution: The term 'conservative amino acid substitution' defined herein refers to a substitution by which one amino acid is substituted for another with one or more shared chemical and/or physical characteristics. Amino acids may be grouped according to shared characteristics. A conservative amino acid substitution is a substitution of one amino acid within a predetermined group of amino acids for another amino acid within the same group, wherein the amino acids within a predetermined groups exhibit similar or substantially similar characteristics.

Disorder: The term 'disorder' used herein refers to a disease or medical problem, and is an abnormal condition of an organism that impairs bodily functions, associated with specific symptoms and signs. It may be caused by external factors, such as invading organisms, or it may be caused by internal dysfunctions, such as impaired catecholamine production or transport. In particular, a disorder as used herein is a dysfunction of dopamine production or abnormal physiological concentration of dopamine.

Expression: The term 'expression' of a nucleic acid sequence encoding a polypeptide is meant transcription of that nucleic acid sequence as mRNA and/or transcription and translation of that nucleic acid sequence resulting in production of that protein.

Expression cassette: The term 'expression cassette' as used herein refers to a genomic sequence that provides all elements required to result in the synthesis of a protein in vivo. This could include, but is not necessarily limited to, a sequence that drives transcription from DNA to mRNA, i.e., a promoter sequence, an open reading frame that includes the genomic sequence for the protein of interest and a 3' untranslated region that enables polyadenylation of the mRNA.

Functional in mammalian cells: The term 'functional in mammalian cells' as used herein, means a sequence, e.g. a nucleotide sequence such as a vector, that when introduced into a mammalian cell results in the translation into a biologically active polypeptide.

Gene therapy: The term 'gene therapy' used herein refers to the insertion of genes into an individual's cells and tissues to treat a disease.

Nucleic acid sequence: The term nucleic acid sequence as used herein refers to a single-stranded or double-stranded chain of two or more nucleotide bases including, without limitation, deoxyribonucleic acid (DNA), ribonucleic acid (RNA), analogs of either DNA or RNA, mRNA, and cDNA.

Operably linked: The term 'operably linked' as used herein indicates that the nucleic acid sequence encoding one or more polypeptides of interest and transcriptional regulatory sequences are connected in such a way as to permit expression of the nucleic acid sequence when introduced into a cell.

Parkinson's Disease: The term 'Parkinson's disease' (also known as Parkinson disease or PD) used herein refers to a degenerative disorder of the central nervous system that often impairs the sufferers motor skills, speech, and other functions. Parkinson's disease belongs to a group of conditions called movement disorders. It is characterized by muscle rigidity, tremor, a slowing of physical movement and, in extreme cases, a loss of physical movement. PD is both chronic and progressive.

Pharmaceutical agent: The terms 'pharmaceutical agent' or 'drug' or 'medicament' refer to any therapeutic or prophylactic agent which may be used in the treatment (including the prevention, diagnosis, alleviation, or cure) of a malady, affliction, condition, disease or injury in a patient. Therapeutically useful genetic determinants, peptides, polypeptides and polynucleotides may be included within the meaning of the term pharmaceutical or drug. As defined herein, a "therapeutic agent", "pharmaceutical agent" or "drug" or "medicament" is a type of bioactive agent.

Pharmaceutical composition: or drug, medicament or agent refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical composition" and "medicament" encompass both the inactive drug and the active metabolite.

Polypeptide: The term 'polypeptide' as used herein refers to a molecule comprising at least two amino acids. The amino acids may be natural or synthetic. 'Oligopeptides' are defined herein as being polypeptides of length not more than 100 amino acids. The term "polypeptide" is also intended to include proteins, i.e. functional biomolecules comprising at least one polypeptide; when comprising at least two polypeptides, these may form complexes, be covalently linked or may be non-covalently linked. The polypeptides in a protein can be glycosylated and/or lipidated and/or comprise prosthetic groups.

Polynucleotide: The term 'polynucleotide' used herein refers to a molecule which is an organic polymer molecule composed of nucleotide monomers covalently bonded in a chain. A "polynucleotide" as used herein refers to a molecule comprising at least two nucleic acids. The nucleic acids may be naturally occurring or modified, such as locked nucleic acids (LNA), or peptide nucleic acids (PNA). Polynucleotide as used herein generally pertains to
  i) a polynucleotide comprising a predetermined coding sequence, or
  ii) a polynucleotide encoding a predetermined amino acid sequence, or
  iii) a polynucleotide encoding a fragment of a polypeptide encoded by polynucleotides (i) or (ii), wherein said fragment has at least one predetermined activity as specified herein; and
  iv) a polynucleotide the complementary strand of which hybridizes under stringent conditions with a polynucleotide as defined in any one of (i), (ii) and (iii), and encodes a polypeptide, or a fragment thereof, having at least one predetermined activity as specified herein; and
  v) a polynucleotide comprising a nucleotide sequence which is degenerate to the nucleotide sequence of polynucleotides (iii) or (iv);
  or the complementary strand of such a polynucleotide.

Promoter: The term 'promoter' used herein refers to a region of DNA that facilitates the transcription of a particular gene. Promoters are typically located near the genes they regulate, on the same strand and upstream.

Protein: The term 'protein' used herein refers to an organic compound, also known as a polypeptide, which is a peptide having at least, and preferably more than two amino acids. The generic term amino acid comprises both natural and non-natural amino acids any of which may be in the 'D' or 'L' isomeric form.

Sequence identity: Sequence identity is determined in one embodiment by utilising fragments of proneurotrophin activity modulator peptides comprising at least 25 contiguous amino acids and having an amino acid sequence which is at least 80%, such as 85%, for example 90%, such as 95%, for example 99% identical to the amino acid sequence of any of the SEQ ID NOs of the present invention, wherein the percent identity is determined with the algorithm GAP, BESTFIT, or FASTA in the Wisconsin Genetics Software Package Release 7.0, using default gap weights.

The following terms are used to describe the sequence relationships between two or more polynucleotides: "predetermined sequence", "comparison window", "sequence identity", "percentage of sequence identity", and "substantial identity".

A "predetermined sequence" is a defined sequence used as a basis for a sequence comparison; a predetermined sequence may be a subset of a larger sequence, for example, as a segment of a full-length DNA or gene sequence given in a sequence listing, such as a polynucleotide sequence selected from the group consisting of SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22, or may comprise a complete DNA or gene sequence. Generally, a predetermined sequence is at least 20 nucleotides in length, frequently at least 25 nucleotides in length, and often at least 50 nucleotides in length.

Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a predetermined sequence of at least 20 contiguous nucleotides and wherein the portion of the polynucleotide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a predetermined sequence over a comparison window of at least 20 nucleotide positions, frequently over a window of at least 25-50 nucleotides, wherein the percentage of sequence identity is calculated by comparing the predetermined sequence to the polynucleotide sequence which may include deletions or additions which total 20 percent or less of the predetermined sequence over the window of comparison. The predetermined sequence may be a subset of a larger sequence, for example, as a segment of the full-length SEQ ID NO: 15, SEQ ID NO: 16, SEQ ID NO: 17, SEQ ID NO: 18, SEQ ID NO: 19, SEQ ID NO: 20, SEQ ID NO: 21 or SEQ ID NO: 22 polynucleotide sequence illustrated herein.

As applied to polypeptides, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

The term "unrelated" or "non-homologous" sequence means a sequence that shares less than 40 percent identity with another sequence, though preferably less than 25 percent identity, with the polypeptides of the present invention.

The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:
i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

The polypeptide fragments according to the present invention, including any functional equivalents thereof, may in one embodiment comprise less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues.

"Functional equivalency" as used in the present invention is according to one preferred embodiment established by means of reference to the corresponding functionality of a predetermined fragment of the sequence.

Functional equivalents or variants of a TH or GCH-1 will be understood to exhibit amino acid sequences gradually differing from the preferred predetermined TH or GCH-1 sequence, as the number and scope of insertions, deletions and substitutions including conservative substitutions increases. This difference is measured as a reduction in homology between the preferred predetermined sequence and the fragment or functional equivalent.

All fragments or functional equivalents of SEQ ID NO: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14 are included within the scope of this invention, regardless of the degree of homology that they show to the respective, predetermined TH and GCH-1 sequences disclosed herein. The reason for this is that some regions of the TH and GCH-1 can be readily mutatable, or capable of being completely deleted, without any significant effect on the binding activity of the resulting fragment.

A functional variant obtained by substitution may well exhibit some form or degree of native TH and GCH-1 activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity is not a principal measure of a fragment being a variant or functional equivalent of a preferred predetermined fragment according to the present invention.

The homology between amino acid sequences may be calculated using well known scoring matrices such as any one of BLOSUM 30, BLOSUM 40, BLOSUM 45, BLO- SUM 50, BLOSUM 55, BLOSUM 60, BLOSUM 62, BLOSUM 65, BLOSUM 70, BLOSUM 75, BLOSUM 80, BLOSUM 85, and BLOSUM 90.

Fragments sharing homology with fragments of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14, respectively, are to be considered as falling within the scope of the present invention when they are preferably at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with said predetermined fragment sequences, respectively. According to one embodiment of the invention the homology percentages refer to identity percentages.

Additional factors that may be taken into consideration when determining functional equivalence according to the meaning used herein are i) the ability of antisera to detect a TH or GCH-1 fragment according to the present invention, or ii) the ability of the functionally equivalent TH or GCH-1 fragment to compete with the corresponding TH or GCH-1 fragment in an assay. One method of determining a sequence of immunogenically active amino acids within a known amino acid sequence has been described by Geysen in U.S. Pat. No. 5,595,915 and is incorporated herein by reference.

A further suitably adaptable method for determining structure and function relationships of peptide fragments is described by U.S. Pat. No. 6,013,478, which is herein incorporated by reference. Also, methods of assaying the binding of an amino acid sequence to a receptor moiety are known to the skilled artisan.

In addition to conservative substitutions introduced into any position of a preferred predetermined TH or GCH polypeptide, or a fragment thereof, it may also be desirable to introduce non-conservative substitutions in any one or more positions of such a polypeptide.

A non-conservative substitution leading to the formation of a functionally equivalent fragment of TH or GCH-1 would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Variants obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same or other TH or GCH-1 fragments and/or TH or GCH-1 molecules, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Covalent or aggregative functional equivalents and derivatives thereof are useful as reagents in immunoassays or for affinity purification procedures. For example, a fragment of TH or GCH-1 according to the present invention may be insolubilized by covalent bonding to cyanogen bromide-activated Sepharose by methods known per se or adsorbed to polyolefin surfaces, either with or without glutaraldehyde cross-linking, for use in an assay or purification of anti-TH or anti-GCH-1 antibodies or cell surface receptors. Fragments may also be labelled with a detectable group, e.g., radioiodinated by the chloramine T procedure, covalently bound to rare earth chelates or conjugated to another fluorescent moiety for use in, e.g., diagnostic assays.

Mutagenesis of a preferred predetermined fragment of TH or GCH-1 can be conducted by making amino acid insertions, usually on the order of about from 1 to 10 amino acid residues, preferably from about 1 to 5 amino acid residues, or deletions of from about from 1 to 10 residues, such as from about 2 to 5 residues.

In one embodiment the fragment of TH or GCH-1 is synthesised by automated synthesis. Any of the commercially available solid-phase techniques may be employed, such as the Merrifield solid phase synthesis method, in which amino acids are sequentially added to a growing amino acid chain. (See Merrifield, J. Am. Chem. Soc. 85:2149-2146, 1963).

Equipment for automated synthesis of polypeptides is commercially available from suppliers such as Applied Biosystems, Inc. of Foster City, Calif., and may generally be operated according to the manufacturers instructions. Solid phase synthesis will enable the incorporation of desirable amino acid substitutions into any fragment of TH or GCH-1 according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Oligomers including dimers including homodimers and heterodimers of fragments of TH and/or GCH-1 according to the invention are also provided and fall under the scope of the invention. TH or GCH-1 functional equivalents and variants can be produced as homodimers or heterodimers with other amino acid sequences or with native TH or GCH-1 sequences. Heterodimers include dimers containing immunoreactive TH fragments as well as GCH-1 fragments that need not have or exert any biological activity.

Sham surgery: is also known as placebo surgery and is an operative intervention that omits the step thought to be therapeutically necessary. In controlled studies sham surgery is performed in the control population to assess the effect of the intervention under study by neutralizing the placebo effect and reducing bias. Contrary however to a placebo, typically exemplified by the inert "sugar pill", sham surgery involves a real surgical intervention to compensate for the effect of anesthesia, the incisional trauma, and pre- and postoperative care and to maintain the illusion of a regular operation. In the present application Sham surgery has been performed in control group animals referred to as the "Les Sham group".

DETAILED DESCRIPTION OF THE INVENTION

The stoichiometric relationship between TH and GCH1 expression levels for optimal DOPA delivery has not been well studied in the brain. To date most studies utilizing TH and GCH1 delivery have utilized a design with no regard to controlling their relative expression levels. The TH enzyme requires the co-factor BH4 for DOPA synthesis. BH4 is synthesized from GTP in a three-step enzymatic reaction where GCH1 is the first and rate-limiting enzyme. The following two enzymes are ubiquitously expressed. There are a number of reasons to look carefully at this process. Firstly, the TH enzyme activity is intricately regulated and the stability of the TH protein is also regulated. One factor that affects the activity is the surrounding amount of BH4. Too little BH4 and the enzyme cannot work efficiently and too much BH4 can inhibit the function.

Secondly, although one molecule of BH4 is consumed for every conversion of tyrosine to DOPA, the GCH1 enzyme is never consumed. As the substrate GTP is abundant in the cell, the need for GCH1 expression may be much less than the TH expression. Continuous DOPA delivery depends on several factors contributing to the establishment of an environment for optimal TH enzyme functionality.

Results obtained by the present inventors suggest that the activation of the TH enzyme follows a three-phase kinetic relationship to the amounts of GCH1 expressed. In the initial phase with a GCH1:TH ratio up to 1:7, the TH function and BH4 synthesis both increase linearly with increasing GCH1. In the second phase when the GCH1 is further increased, up to 5.5E9 GCH1 genome copies, (a level corresponding to a 1:3 GCH1:TH ratio), the increase in BH4 levels continues linearly but the TH function starts to show signs of saturation. In the third phase, saturation is evident in both TH function and BH4 synthesis when increasing rAAV5-GCH1 titers beyond 5.5E9 genome copies Taken together, these data show that the working range between 1:3 and 1:7 GCH1:TH ratio can result in an efficient DOPA synthesis where TH function is optimized.

Accordingly, in certain embodiments, the TH gene is expressed at about 3-7 fold higher levels than GCH1. Furthermore, using the vectors and methods and vectors described herein, a stable well defined ratio of transgene expression levels can be maintained to provide predictable and optimized expression levels in vivo.

Earlier strategies have utilized either a two-vector design or single vector multi-cistronic vectors. The use of separate viral vectors each coding for one of the genes has a number of limitations. Firstly, the "Product" becomes in reality two drugs with each having its own production variation. As this is difficult to assess in vitro, clinical grade production may be very troublesome. Secondly, although at a global scale the expression pattern of the two genes might look similar, the number of copies of the two vectors in an individual cell might vary dramatically, thus resulting in varying levels of DOPA synthesis. In addition, the effect might be aggravated with many cells receiving none or only one of the genes and therefore display very limited DOPA synthesis, if any.

A more attractive approach is to merge the genes into a single vector as the two genes will always be expressed in the same cell, and there will just be one "product". However, this approach has been hindered by gene sequences too big to fit into certain vector constructs, for example, a recombinant AAV vector. The packaging capacity of AAV is optimized around the size of the wild-type AAV genome (4.7 kb). If the recombinant genome significantly exceeds this size, the production titers and in vivo efficacy are both severely impaired.

In gene therapy, a preferred type of viral vector is the AAV. AAV is advantageous for gene therapy due to a number of features. Of particular importance is the wild-type virus' lack of pathogenicity. It also can infect non-dividing cells and can provide long-term, stable gene expression. The desired gene together with a promoter to drive transcription of the gene can be inserted between the inverted terminal repeats (ITR) that aid in concatamer formation in the nucleus after the single-stranded vector DNA is converted by host cell DNA polymerase complexes into double-stranded DNA. AAV-based gene therapy vectors form episomal concatamers in the host cell nucleus. AAVs also present very low immunogenicity, seemingly restricted to generation of neutralizing antibodies, while they induce no clearly-defined cytotoxic response. These features make AAV an attractive candidate for gene therapy, particularly in the central nervous system (CNS).

While the dopamine synthesis pathway is commonly considered to include two major enzymes, TH and AADC, the inventors have shown herein that gene therapy using a vector or vectors that express TH and GCH1, without expressing AADC, can provide symptomatic and/or therapeutic relief. This is of outmost importance, as the limited packaging capacity of certain viral vectors, such as the AAV vector, prohibits or limits the inclusion of all three genes, TH, GCH1, and AADC. Moreover, the combination of the two genes TH and GCH1 is not possible with traditional bi-cistronic vector genome construction. While it might be possible to truncate the TH enzyme at the N-terminal to reduce the size of the gene, this comes at the expense of removing the intrinsic safety mechanism of feedback inhibition and phosphorylation. Such truncated enzyme would continue to be efficient even at times when cytosolic DA concentrations would approach toxic levels. This is not be the case with the full length TH cDNA as utilized in this invention.

Certain embodiments described herein include radically different plasmid designs. For example, instead of enabling dual gene expression through the use of an internal ribosome entry site, certain embodiments utilize a dual expression cassette with two promoters. With the synthetic fusion promoters traditionally used in gene therapy such as the synthetic chicken b-actin promoter containing a rabbit gamma-globulin intron, preceded with an enhancer element from the cytomegalovirus promoter (termed as the chicken b-actin, CBA, promoter) this plasmid design would not be possible. The use of a small, strong endogenous promoter has allowed this different plasmid design approach.

One-Vector Expression System

Figure 2:
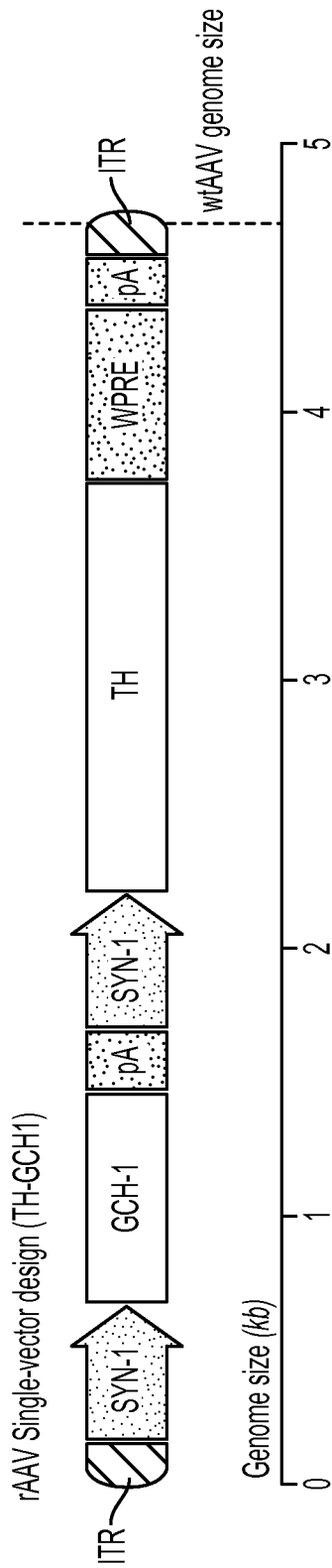
FIG. 2: Vector constructs. A gene construct was generated to express both tyrosine hydroxylase (TH) and GTP cyclohydrolase 1 (GCH-1) from a single vector genome. To achieve an increased expression of TH over the GCH1 gene, a woodchuck hepatitis virus post-transcriptional regulatory element (WPRE) was added. Both genes were driven by the human Synapsin 1 promoter (SYN-1) and trafficking was enhanced using a SV40 polyadenylation sequence (pA). The complete gene sequence was inserted between inverted terminal repeats (ITR) from AAV serotype 2.

In certain embodiments, the present invention relates to a one-vector expression system comprising two polynucleotides encoding two polypeptides designed to be differentially expressed (described in FIG. 2). The two encoded polypeptides, tyrosine hydroxylase (TH) and GTP-cyclohydrolase 1 (GCH1), can preferentially be expressed at a ratio between 3:1 and 7:1.

Along with other polypeptides, TH and GCH1 are essential enzymes in the production of dopamine as they regulate the production of L-dopa from tyrosine. Other factors are involved in dopamine synthesis, but the stoichiometric relationship between TH and GCH1 can be a restrictive factor in this process.

It is therefore a major object of the present invention to provide a vector construct that delivers optimized proportions of TH and GCH1. Moreover, the present invention provides a method to deliver the vector construct locally in order to limit the increased production of dopamine to the cells in need thereof.

Viral Vectors

Broadly, gene therapy seeks to transfer new genetic material to the cells of a patient with resulting therapeutic benefit to the patient. Such benefits include treatment or prophylaxis of a broad range of diseases, disorders and other conditions.

Gene therapy may be classified into two distinct types: germ line gene therapy, wherein genetic material is transferred into germ cells and will thus be heritable, and somatic gene therapy, wherein genetic material is transferred into somatic cells and will thus not be heritable.

Ex vivo gene therapy approaches involve modification of isolated cells such as stem cells, which can be infused, grafted or otherwise transplanted into the patient. See, e.g., U.S. Pat. Nos. 4,868,116, 5,399,346 and 5,460,959. In vivo gene therapy on the contrary seeks to directly target host patient tissue in vivo.

Viral vectors are useful tools for delivering genetic material into a host organism. Viruses useful as gene transfer vectors include papovavirus, adenovirus, vaccinia virus, adeno-associated virus (AAV), herpes virus, and retroviruses, such as HIV, SIV, FIV, EIAV, MoMLV.

Preferred viruses for treatment of disorders of the central nervous system are lentiviruses and adeno-associated viruses. Both types of viruses can integrate into the genome without cell divisions, and both types have been tested in pre-clinical animal studies for indications in the nervous system, in particular in the central nervous system.

A preferred type of viral vector is the AAV. AAV is interesting in gene therapy due to a number of features. Chief amongst these is the wild-type virus' apparent lack of pathogenicity and that it can also infect non-dividing cells. The wild-type AAV genome integrates most frequently into a specific site (designated AAVS1) in the human chromosome 19, while random incorporations into the genome take place with a negligible frequency. The feature makes it somewhat more predictable than retroviruses, which present the threats of a random insertion and of mutagenesis. With AAVs as gene therapy vectors, however, this integrative capacity can be eliminated by removal of the rep and cap from the DNA of the vector. As the rep and cap genes have no functional value in a replication deficient viral vector, they can be eliminated from the vector genome. In the place of these wild-type AAV genes, the desired gene(s) together with a promoter to drive transcription of the gene can be inserted between the inverted terminal repeats (ITR). The ITRs are important for the viral vector packaging of the vector DNA and aids in concatamer formation in the nucleus after the single-stranded vector DNA is converted by host cell DNA polymerase complexes into double-stranded DNA.

AAV-based gene therapy vectors can form episomal concatamers in the host cell nucleus. In non-dividing cells, these concatamers can remain intact for the life of the host cell. In dividing cells, AAV DNA can be lost through cell division, since the episomal DNA is not replicated along with the host cell DNA. Random integration of AAV DNA into the host genome is low but may be detectable. AAVs present low immunogenicity, seemingly restricted to the generation of neutralizing antibodies, while they induce no clearly-defined cytotoxic response. These features, along with the ability to infect quiescent cells, present some of their advantages over adenoviruses as vectors for the human gene therapy. These features make AAV an attractive candidate for creating viral vectors for gene therapy in the central nervous system (CNS).

Viral vectors, including AAV vectors, have certain cloning capacities i.e., they are able to carry a certain amount of polynucleotides. Thus, in certain embodiments, the present invention relates to a viral vector with a packaging capacity ranging from 1 to 40 kb, such as from 1 to 30 kb, for example from 1 to 20 kb, such as from 1 to 15 kb, for example from 1 to 10 kb, such as from 1 to 8 kb, for example from 2 to 7 kb, such as from 3 to 6 kb, for example from 4 to 5 kb. In a preferred embodiment, the present invention relates to an AAV vector with a packaging capacity of 4.8 kb.

At least 11 serotypes of the AAV presently exist. Serotype 2 has been most extensively investigated, and AAV2 presents natural tropism towards e.g., skeletal muscles, vascular smooth muscle cells, hepatocytes and in particular neurons. However, other serotypes have proved effective as tolls for gene therapy; for instance AAV6 appears particularly useful in infecting airway epithelial cells, AAV7 presents high transduction rate of murine skeletal muscle cells (similarly to AAV1 and AAV5), AAV8 is particularly useful in transducing hepatocytes, and AAV1 and 5 are efficient in gene delivery to vascular endothelial cells.

The humoral immunity instigated by infection with the wild type AAV is thought to be a very common event. The associated neutralising activity limits the usefulness of the most commonly used serotype AAV2 in certain applications. Accordingly the majority of clinical trials currently underway into the brain involve delivery of AAV2, a relatively immunologically privileged organ.

In addition to using different serotypes of the AAV, it is possible to combine different serotypes, such as using the plasmid of one serotype packaged in the capsid of another serotype.

In one embodiment the adeno associated vector (AAV) vector of the present invention is an AAV2 vector.

In a further embodiment the AAV2 vector is packaged in an AAV capsid other than an AAV2 capsid.

In yet a further embodiment the AAV2 vector is packed in an AAV5 capsid.

AAV vectors can be prepared using two major principles, transfection of human cell line monolayer culture or free floating insect cells. Monolayer cell cultures are transfected through calcium phosphate precipitation, lipofection or other means with a mix of two or three plasmid preparations containing a transfer plasmid with the vector genome and one or two helper plasmids containing the necessary genes for vector capsid synthesis. For insect sell cultures, this process is normally replaced by transfection of the cells using bacculovirus constructs that contain the same functions. The cells, supernatant or both are then collected for purification and concentration of the vector. This can be achieved through any combination of caesium chloride or iodixanol gradient purification, ion exchange chromatography, gel filtration and affinity chromatography and ultracentrifugation. Methods for preparation of AAV are described in the art, e.g. U.S. Pat. No. 5,677,158, U.S. Pat. No. 6,309,634, and U.S. Pat. No. 6,451,306 describe examples of delivery of AAV to the central nervous system.

Accordingly, in a main aspect, the present invention relates to a one-vector expression system comprising a) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, with the proviso that said vector does not comprise a nucleotide sequence encoding an aromatic amino acid decarboxylase (AADC) polypeptide, or b) a first and a second expression cassette, said first expression cassette comprising a nucleotide sequence comprising a first promoter sequence operably linked to a first nucleotide sequence, said first nucleotide sequence encodes a GTP-cyclohydrolase 1 (GCH1) polypeptide or a biologically active fragment or variant thereof, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, wherein the vector is an adeno associated vector (AAV), or c) an expression cassette comprising a promoter, a first nucleotide sequence, a translation initiating nucleotide sequence such as an internal ribosome entry site (IRES) and a second nucleotide sequence, wherein said promoter is operably linked to said first nucleotide sequence, and wherein said translation initiating nucleotide sequence is linking said first and said second nucleotide sequence, wherein said first nucleotide sequence encodes a GTP-cyclohydrolase 1 (GCH1) polypeptide or a biologically active fragment or variant thereof, and wherein said second nucleotide sequence encodes a tyrosine hydroxylase (TH) polypeptide or a biologically active fragment or variant thereof, or d) an expression cassette comprising a first nucleotide sequence, a translation initiating nucleotide sequence such as an internal ribosome entry site (IRES) and a second nucleotide sequence wherein said translation initiating nucleotide sequence links said first and said second nucleotide sequence, and wherein the sequence comprising said first nucleotide sequence linked to said translation initiating nucleotide sequence linked to said second nucleotide sequence is flanked by 5' and 3' terminal repeats, and wherein said first nucleotide sequence encodes a GTP-cyclohydrolase 1 (GCH1) polypeptide or a biologically active fragment or variant thereof, and wherein said second nucleotide sequence encodes a tyrosine hydroxylase (TH) polypeptide or a biologically active fragment or variant thereof, wherein said terminal repeats comprises a sequence capable of directing the expression of an operably linked polypeptide.

In one embodiment of the vector described herein above, the GTP-cyclohydrolase 1 (GCH1) polypeptide or the biologically active fragment or variant thereof, expressed by said first expression cassette, is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein the tyrosine hydroxylase (TH) polypeptide or the biologically active fragment or variant thereof, expressed by said second expression cassette is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14.

In another embodiment of the vector defined herein above, the GTP-cyclohydrolase 1 (GCH1) polypeptide or the biologically active fragment or variant thereof expressed by, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said tyrosine hydroxylase (TH) polypeptide or a biologically active fragment or variant thereof, expressed by said second expression cassette is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14.

In another embodiment of the vector defined herein above, the encoded GTP-cyclohydrolase 1 (GCH1) polypeptide or the biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5, SEQ ID NO. 6, and wherein the encoded tyrosine hydroxylase (TH) polypeptide or the biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14.

In another embodiment of the vector defined herein above, the GTP-cyclohydrolase 1 (GCH1) polypeptide or the biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5, and SEQ ID NO. 6, and wherein the encoded tyrosine hydroxylase (TH) polypeptide or the biologically active fragment or variant thereof, is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14.

In certain embodiments, inclusion of the AADC gene into the vector can be disadvantageous for any of a number of reasons. First, it generates a new system that can without modulation convert tyrosine to dopamine. As the transduced cells in the striatum lack the mechanisms for sequestering the dopamine into vesicles, the dopamine can accumulate rapidly in the cytosol. If the TH enzyme is left with the N-terminal regulatory domain the dopamine produced can directly inhibit the DOPA synthesis through negative feedback which can severely limit the efficacy of the treatment. On the other hand, if the TH enzyme is truncated, the cytosolic dopamine levels can rapidly increase as the transduced cells also lack mechanisms to release the dopamine. Such increases in cytosolic dopamine have been shown to lead to degeneration of the striatal neurons which would can not only remove the symptomatic relief, but also can convert the Parkinson's disease to Multi system atrophy (MSA), a L-DOPA unresponsive disorder with next to no treatment alternatives.

Second, the inclusion of the AADC gene also can affect the patient's response to oral L-DOPA pharmacotherapy. It is known that one of the major adverse events of L-DOPA pharmacotherapy is the dyskinesias. These are thought to result, at least in part, due to the fluctuations of dopamine levels in the striatum caused by the pulsatile administration route. If the conversion rate from L-DOPA to dopamine is enhanced focally in the striatum, this can aggravate the fluctuations and also increase the dyskinesias. This has in fact been observed in animal models transduced with the AADC gene.

Omission of the AADC gene on the other hand can provide shuttling of the DOPA out of striatal neurons through available large amino acid transporters and thereby provide a safety mechanism, as the available AADC enzyme can regulate the conversion speed. The neurons with endogenous AADC enzyme activity also can have the capacity to store and release the dopamine, thus reducing the risk of dopamine toxicity. Accordingly, in certain embodiments the vector does not comprise a nucleotide sequence encoding an aromatic amino acid decarboxylase (AADC) polypeptide.

Thus in another main aspect, the present invention relates to a one-vector expression system comprising a) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, wherein said polypeptide or a biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14, with the proviso that said vector does not comprise a nucleotide sequence encoding an aromatic amino acid decarboxylase (AADC) polypeptide, or b) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, wherein said polypeptide or a biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14, wherein the vector is an adeno associated vector (AAV), or c) an expression cassette comprising a promoter, a first nucleotide sequence, a translation initiating nucleotide sequence such as an internal ribosome entry site (IRES) and a second nucleotide sequence, wherein said promoter is operably linked to said first nucleotide sequence, and wherein said translation initiating nucleotide sequence is linking said first and said second nucleotide sequence, wherein said first nucleotide sequence encodes a GTP-cyclohydrolase 1 (GCH1) polypeptide or a biologically active fragment or variant thereof, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5, SEQ ID NO. 6, and wherein said second nucleotide sequence encodes a tyrosine hydroxylase (TH) polypeptide or a biologically active fragment or variant thereof, wherein said polypeptide or a biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, or d) an expression cassette comprising a first nucleotide sequence, a translation initiating nucleotide sequence such as an internal ribosome entry site (IRES) and a second nucleotide sequence wherein said translation initiating nucleotide sequence is linking said first and said second nucleotide sequence, and wherein the sequence comprising said first nucleotide sequence linked to said translation initiating nucleotide sequence linked to said second nucleotide sequence is flanked by 5' and 3' terminal repeats, and wherein said first nucleotide sequence encodes a GTP-cyclohydrolase 1 (GCH1) polypeptide or a biologically active fragment or variant thereof, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said second nucleotide sequence encodes a tyrosine hydroxylase (TH) polypeptide or a biologically active fragment or variant thereof, wherein said polypeptide or a biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, wherein said terminal repeats comprise a sequence capable of directing the expression of an operably linked polypeptide.

In another aspect, the present invention relates to a one-vector expression system comprising a) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, wherein said polypeptide or a biologically active fragment or variant thereof is at least 75% identical, such as at least 80% identical, e.g. at least 90% identical, such as at least 92% identical, e.g. at least 95% identical, such as at least 97% identical, e.g., at least 98% identical, such as at least 99% identical, e.g. at least 99.5% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, wherein said polypeptide or a biologically active fragment or variant thereof is at least 75% identical, such as at least 80% identical, e.g. at least 90% identical, such as at least 92% identical, e.g. at least 95% identical, such as at least 97% identical, e.g. at least 98% identical, such as at least 99% identical, e.g. at least 99.5% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14, with the proviso that said vector does not comprise a nucleotide sequence encoding an aromatic amino acid decarboxylase (AADC) polypeptide, or b) a first and a second expression cassette, said first expression cassette comprising a nucleotide sequence comprising a first promoter sequence operably linked to a first nucleotide sequence, said first nucleotide sequence encoding a GTP-cyclohydrolase 1 (GCH1) polypeptide or a biologically active fragment or variant thereof, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, wherein said polypeptide or a biologically active fragment or variant thereof is at least 75% identical, such as at least 80% identical, e.g. at least 90% identical, such as at least 92% identical, e.g. at least 95% identical, such as at least 97% identical, e.g. at least 98% identical, such as at least 99% identical, e.g. at least 99.5% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14, wherein the vector is an adeno associated vector (AAV), or c) an expression cassette comprising a promoter, a first nucleotide sequence, a translation initiating nucleotide sequence such as an internal ribosome entry site (IRES) and a second nucleotide sequence, wherein said promoter is operably linked to said first nucleotide sequence, and wherein said translation initiating nucleotide sequence is linking said first and said second nucleotide sequence, wherein said first nucleotide sequence encodes a GTP-cyclohydrolase 1 (GCH1)

polypeptide or a biologically active fragment or variant thereof, wherein said polypeptide or a biologically active fragment or variant thereof is at least 75% identical, such as at least 80% identical, e.g. at least 90% identical, such as at least 92% identical, e.g. at least 95% identical, such as at least 97% identical, e.g. at least 98% identical, such as at least 99% identical, e.g. at least 99.5% identical to a polypeptide selected from the group consisting of SEQ ID NO. 1, SEQ ID NO. 2, SEQ ID NO. 3, SEQ ID NO. 4, SEQ ID NO. 5, SEQ ID NO. 6, and wherein said second nucleotide sequence encodes a tyrosine hydroxylase (TH) polypeptide or a biologically active fragment or variant thereof, wherein said polypeptide or a biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, or d) an expression cassette comprising a first nucleotide sequence, a translation initiating nucleotide sequence such as an internal ribosome entry site (IRES) and a second nucleotide sequence wherein said translation initiating nucleotide sequence is linking said first and said second nucleotide sequence, and wherein the sequence comprising said first nucleotide sequence linked to said translation initiating nucleotide sequence linked to said second nucleotide sequence is flanked by 5' and 3' terminal repeats, and wherein said first nucleotide sequence encodes a GTP-cyclohydrolase 1 (GCH1) polypeptide or a biologically active fragment or variant thereof, wherein said polypeptide or a biologically active fragment or variant thereof is at least 75% identical, such as at least 80% identical, e.g. at least 90% identical, such as at least 92% identical, e.g. at least 95% identical, such as at least 97% identical, e.g., at least 98% identical, such as at least 99% identical, e.g., at least 99.5% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said second nucleotide sequence encodes a tyrosine hydroxylase (TH) polypeptide or a biologically active fragment or variant thereof, wherein said polypeptide or a biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, wherein said terminal repeats comprise a sequence capable of directing the expression of an operably linked polypeptide.

In one embodiment the vector of the present invention is a minimally integrating vector.

In one embodiment the vector of the present invention is the vector described in FIG. 6.

In one embodiment the vector as defined herein above has a packaging capacity from 1 to 40 kb, for example from 1 to 30 kb, such as from 1 to 20 kb, for example from 1 to 15 kb, such as from 1 to 10, for example from 1 to 8 kb, such as from 2 to 7 kb, for example from 3 to 6 kb, such as from 4 to 5 kb.

In a preferred embodiment, the vector as defined herein above has a packaging capacity from 4.5 to 4.8 kb.

In one embodiment the vector of the present invention is a viral vector, wherein said vector is selected from the group consisting of an adeno associated vector (AAV), lentiviral vector, adenoviral vector and retroviral vector.

In a preferred embodiment the vector is an adeno associated vector (AAV).

Even though AAV vectors are preferred, other vectors may be used for the present invention. Thus, in another embodiment the vector of the present invention is a plasmid vector.

In yet another embodiment the vector of the present invention is a synthetic vector.

In one embodiment the vector is functional in mammalian cells. In one embodiment the vector is only functional in mammalian cells.

In one embodiment the present invention relates to a vector based on any AAV serotype identified in humans, non-human primates, other mammalian species, or chimeric versions thereof.

In a preferred embodiment, the present invention relates to a vector based on AAV vectors of any serotype modified to express altered or novel coat proteins. In a more preferred embodiment, the present invention relates to an AAV vector, more preferably a serotype 2 AAV vector, more preferably a serotype 2 AAV vector packed in a serotype 5 AAV capsid. For capsid selection, two factors may contribute to the choice of preferred serotype. The first is the presence of neutralizing antibodies for the wild-type equivalents. It has been shown that the most prevalent serotype in various human populations is serotype 2. Thus, there is a value to use a serotype that shares the least capsid homology to serotype 2 and other serotypes. Serotype 5 stands out in that it shares only 53-57% capsid sequence homology to the other AAV serotypes 1 through 9 (Daya and Berns. Gene therapy using adeno-associated virus vectors. ClinMicrobiol Rev (2008) vol. 21 (4) pp. 583-93). A second factor that may contribute to the spread of the transduction in the human brain is the cell surface residues that the vector capsid displays affinity to. While the AAV serotype 2 has a strong affinity to heparin sulfate proteoglycan (HSPG), the AAV5 serotype does not. This may aid the spread as the HSPG is abundant in the brain.

Expression of a gene is controlled at the transcription, translation or post-translation levels. Transcription initiation is an early and critical event in gene expression. This depends on the promoter and enhancer sequences and is influenced by specific cellular factors that interact with these sequences. The AAV may be designed to contain one or more polynucleotides of different origin. A vector construct may comprise one or more promoters. In one embodiment of the present invention, said promoter(s) are specific to mammalian cells, selected from but not limited to the group consisting of human neural cells including human neurons, Chinese hamster ovary cells, CHO-K1, baby hamster kidney cells, mouse fibroblast-3T3 cells, African green monkey cell lines, rat adrenal pheochromocytoma, AT3 cells, rat glial tumor cells, rat neuronal cells and rat hippocampal cells.

In a preferred embodiment, the present invention relates to a vector containing a genomic sequence where the expression of the enzymes is controlled by one or more promoter(s) that permit high expression in neurons, such as for example striatal neurons. In a more preferred embodiment, said promoter(s) are neuron-specific. In a most preferred embodiment, said promoter(s) are human synapsin promoter(s).

In one embodiment, the first and/or second promoter of the expression construct of the present invention, as defined herein above, is a promoter specific for mammalian cells. In a further embodiment, said mammalian cell is a neural cell. In yet a further embodiment, said neural cell is a neuron.

In one embodiment, both said first and said second promoter are Synapsin1 promoters.

In another embodiment, one of either said first or said second promoters is a Synapsin1 promoter.

In one embodiment the promoter used in the present invention is a constitutive promoter, wherein said constitutively active promoter is selected from the group consisting of CAG, CMV, human UbiC, RSV, EF-1alpha, SV40, Mt1.

In another embodiment the promoter is an inducible promoter, wherein said inducible promoter is selected from the group consisting of Tet-On, Tet-Off, Mo-MLV-LTR, Mx1, progesterone, RU486 and Rapamycin-inducible promoter.

The promoter of the present invention may be a constitutive promoter, including but not limited to the group consisting of CAG promoter, CMV promoter, human UbiC promoter, RSV promoter, EF-1alpha promoter, SV40 promoter and Mt1 promoter.

In addition to promoters, an expression vector may also comprise one or more polyadenylation sequence(s). A polyadenylation sequence is necessary for production of mature mRNA for translation of the transcribed product into a polypeptide. In one embodiment of the present invention, a polyadenylation sequence is operably linked with the sequence encoding TH or GCH-1, of the present invention. In a more preferred embodiment, the 5' end of a polyadenylation sequence is operably linked to the 3' end of the sequence encoding TH or GCH-1 of present invention. In a more preferred embodiment, said polyadenylation sequence is a SV40 polyadenylation sequence.

In one embodiment of the present invention, either said first expression cassette or said second expression cassette comprises a polyadenylation sequence.

In another embodiment of the present invention, both said first expression cassette and said second expression cassette comprises polyadenylation sequences.

In one embodiment, the polyadenylation sequence is a SV40 polyadenylation sequence wherein the 5' end of said polyadenylation sequence is operably linked to the 3' of the first and/or said second nucleotide sequence defined herein above.

In one embodiment of the present invention, said first nucleotide sequence encoding a GTP-cyclohydrolase 1 (GCH1) polypeptide or a biologically active fragment or variant thereof comprises the sequence of SEQ ID NO. 18.

In another embodiment of the present invention said second nucleotide sequence encoding a tyrosine hydroxylase (TH) polypeptide or a biologically active fragment or variant thereof comprises the sequence of SEQ ID NO. 21.

IRES is the abbreviation for internal ribosome entry site and is a nucleotide sequence that allows for translation initiation in the middle of a mRNA sequence as part of the greater process of protein synthesis. In one embodiment an internal ribosome entry site (IRES) may also be included in the expression vector construct of the present invention.

To insert genetic sequences into host DNA, viruses often use sequences of DNA that repeats up to thousands of times, so called repeats, or terminal repeats including long terminal repeats (LTR) and inverted terminal repeats (ITR), wherein said repeat sequences may be both 5' and 3' terminal repeats. ITRs aid in concatamer formation in the nucleus after the single-stranded vector DNA is converted by host cell DNA polymerase complexes into double-stranded DNA. ITR sequences may be derived from viral vectors, preferably AAV, more preferably AAV2.

In one embodiment, the expression cassettes of the vector according to the present invention comprise a 5' terminal repeat and a 3' terminal repeat.

In one embodiment said 5' and 3' terminal repeats are selected from Inverted Terminal Repeats [ITR] and Long Terminal Repeats [LTR].

In one embodiment of said 5' and 3' terminal repeats are AAV Inverted Terminal Repeats [ITR].

In one further embodiment said Inverted Terminal Repeats comprises the sequences of SEQ ID NO. 15 and SEQ ID NO. 16.

An expression vector may also comprise one or more enhancers or regulatory elements, such as post-transcriptional regulatory elements, to increase or regulate the level of transgene expression. This means that the expression of one or more polynucleotide sequences comprised in a viral vector may be increased or decreased as compared to the expression efficacy in a vector without enhancers and/or regulators. By using said enhancers and/or regulators, it is also possible to differentially express two or more genes included in a vector. It is thus possible to direct an enhancer or regulator to a distinct polynucleotide sequence within a vector with two or more polynucleotide sequences. Enhancers and regulators include, but are not limited to, SP163, rat InsulinII-intron or other introns, CMV enhancer, and Chicken [beta]-globin insulator or other insulators.

In a preferred embodiment, the polynucleotide sequences of the present invention are regulated by a post-transcriptional regulatory element embedded within the vector. In a more preferred embodiment, said regulatory element is a Woodchuck hepatitis virus post-transcriptional regulatory element. In a more preferred embodiment (WPRE), said WPRE regulates the expression ratio between the two polynucleotides of the invention, preferably by increasing the expression of TH.

In one embodiment of the present invention, said second nucleotide sequence is operably linked to a post-transcriptional regulatory element, wherein said post-transcriptional regulatory element may be a Woodchuck hepatitis virus post-transcriptional regulatory element (WPRE), wherein said Woodchuck hepatitis virus post-transcriptional regulatory element may comprise the sequence of SEQ ID NO. 22.

In one particular embodiment, the expression of the two polypeptides of the invention occurs at a ratio wherein TH expression is higher than GCH 1 expression. In a preferred embodiment, the TH:GCH 1 ratio is between 1:1 and 50:1, such as between 1:1 and 45:1, for example between 1:1 and 40:1, such as between 1:1 and 35:1, for example between 1:1 and 30:1, such as between 1:1 and 29:1, for example between 1:1 and 28:1, such as between 1:1 and 27:1, for example between 1:1 and 26:1, such as between 1:1 and 25:1, for example between 1:1 and 24:1, such as between 1:1 and 23:1, for example between 1:1 and 22:1, such as between 1:1 and 21:1, for example between 1:1 and 20:1, such as between 1:1 and 19:1, for example between 1:1 and 18:1, such as between 1:1 and 17:1, for example between 1:1 and 16:1, such as between 1:1 and 15:1, for example between 1:1 and 14:1, such as between 1:1 and 13:1, for example between 1:1 and 12:1, such as between 1:1 and 11:1, for example between 1:1 and 10:1, such as between 1:1 and 9:1, such as between 1:1 and 8:1, for example between 1:1 and 7:1, such as 7:1, for example 6:1, such as 5:1, for example 4:1, such as 3:1, for example between 2:1 and 8:1, such as between 3:1 and 7:1.

In order to control that the expression ratio is in the desired range, several possibilities exist. The level of mRNA present in a sample may be measured by RT PCR. RT-PCR utilizes a pair of primers, which are complementary to a defined sequence on each of the two strands of the cDNA. These primers are then extended by a DNA polymerase and a copy of the strand is made after each cycle, leading to logarithmic amplification. RT-PCR includes three major steps. The first step is the reverse transcription where RNA is reversely transcribed to cDNA using a reverse transcriptase and primers. The next step involves the denaturation of the dsDNA, to make the two strands separate and the primers can bind again at lower temperatures and begin a new chain reaction.

The final step of PCR amplification is the DNA extension from the primers which is done by the thermostable Taq DNA polymerase. The amplicons can be visualised as the amplification progresses using a fluorescent reporter molecule.

The amount of protein may be measured in several ways.

Polynucleotide levels may be detected by radioimmunoassay (RIA). RIA is a very sensitive technique used to measure concentrations of antigens without the need to use a bioassay. To perform a radioimmunoassay, a known quantity of an antigen is made radioactive, frequently by labeling it with gamma-radioactive isotopes of iodine attached to tyrosine. This radio labeled antigen is then mixed with a known amount of antibody for that antigen, and as a result, the two chemically bind to one another. Then, a sample of serum from a patient containing an unknown quantity of that same antigen is added. This causes the unlabeled (or "cold") antigen from the serum to compete with the radio labeled antigen for antibody binding sites. As the concentration of "cold" antigen is increased, more of it binds to the antibody, displacing the radio labeled variant, and reducing the ratio of antibody-bound radio labeled antigen to free radio labeled antigen. The bound antigens are then separated from the unbound ones, and the radioactivity of the free antigen remaining in the supernatant is measured. Using known standards, a binding curve can then be generated which allows the amount of antigen in the patient's serum to be derived.

Enzyme-linked immunosorbent assay (ELISA) may also be employed. ELISA is a quantitative technique used to detect the presence of protein, or any other antigen, in a sample. In ELISA an unknown amount of antigen is affixed to a surface, and then a specific antibody is washed over the surface so that it can bind to the antigen. This antibody is linked to an enzyme, and in the final step a substance is added that the enzyme can convert to some detectable signal.

Several types of ELISA exist, including Indirect ELISA, Sandwich ELISA, Competitive ELISA and Reverse ELISA. Other immuno-based assays may also be used, such as chemiluminescent immunometric assays and Dissociation-Enhanced Lanthinide Immunoassays. Nephelometry and turbidimetry is also applicable for protein determination.

Another way to determine protein amount is by chromatography-based methods, more specifically liquid chromatography. Affinity chromatography is based on selective non-covalent interaction between an analyte and specific molecules.

Ion exchange chromatography uses ion exchange mechanisms to separate analytes. Ion exchange chromatography uses a charged stationary phase to separate charged compounds. In conventional methods the stationary phase is an ion exchange resin that carries charged functional groups which interact with oppositely charged groups of the compound to be retained. Size exclusion chromatography (SEC) is also known as gel permeation chromatography (GPC) or gel filtration chromatography. SEC is used to separate molecules according to their size (or more accurately according to their hydrodynamic diameter or hydrodynamic volume). Smaller molecules are able to enter the pores of the media and, therefore, take longer to elute, whereas larger molecules are excluded from the pores and elute faster.

Reversed-phase chromatography is an elution procedure in which the mobile phase is significantly more polar than the stationary phase. Hence, polar compounds are eluted first while non-polar compounds are retained.

Alternative methods include electrophoresis. Electrophoresis utilizes the motion of dispersed particles relative to a fluid under the influence of an electric field. Particles then move with a speed according to their relative charge. More specifically, the following electrophoretic methods may be used for detection of CD163: Sodium dodecyl sulfate polyacrylamide gel electrophoresis (SDS-PAGE), Rocket immunoelectrophoresis, Affinity immunoelectrophoresis and Isoelectric focusing.

Flow cytometry may also be used to determine protein amount. In flow cytometry a beam of light of a single wavelength is directed onto a hydrodynamically-focused stream of fluid. A number of detectors (some fluorescent) are aimed at the point where the stream passes through the light beam: one in line with the light beam and several detectors perpendicular to it. Each suspended particle from 0.2 to 150 micrometers passing through the beam scatters the light in some way, and fluorescent chemicals found in the particle or attached to the particle may be excited into emitting light at a longer wavelength than the light source. This combination of scattered and fluorescent light is picked up by the detectors, and, by analysing fluctuations in brightness at each detector, it is then possible to derive various types of information about the physical and chemical structure of each individual particle.

The Luminex technology, is based on a technique where microspheres are coated with reagents specific to capture a specific antigen from a sample.

MS is an analytical technique for the determination of the elemental composition of a sample or molecule. It is also used for elucidating the chemical structures of molecules, such as proteins and other chemical compounds. The MS principle consists of ionizing chemical compounds to generate charged molecules or molecule fragments and measurement of their mass-to-charge ratios.

Enzyme activity may be measured by a variety of methods. All enzyme assays measure either the consumption of substrate or production of product over time. In general, four types of experiments are mostly used: initial rate experiments, progress curve experiments, transient kinetics experiments or relaxation experiments. These assays include spectrophotometric, fluorometric, calorimetric, chemiluminescent, light scattering, radiometric, chromatographic and colorimetric assays, such as an MTT assay.

Therefore, in one embodiment, the expression ratio is determined by measuring amount of TH encoding polynucleotide versus the amount of GCH 1 encoding polynucleotide present, more preferably the amount of TH mRNA versus the amount of GCH 1 mRNA. In another embodiment, the expression of TH and GCH 1 polypeptides are measured by the amount of protein expressed. In yet another preferred embodiment, the expression ration is determined by measuring the enzymatic activity of the TH and GCH 1 polypeptides.

In one embodiment of the present invention the TH:GCH1 ratio is at least 3:1, such as at least 4:1, for example at least 5:1, such as at least 6:1, for example at least 7:1, such as at least 10:1, for example 15:1, such as 20:1, for example 25:1, such as 30:1, for example 35:1, such as 40:1, for example 45:1, such as 50:1.

In a preferred embodiment of the present invention the TH:GCH1 ratio is 7:1.

In one embodiment the ratio between the expression levels of the TH and GCH1 of the present invention, is determined by measuring the activity of the expressed TH and GCH1 enzymes.

In another embodiment the ratio between the expression levels of the TH and GCH1 of the present invention, is determined by measuring the amount of Tetrahydrobiopterin ($BH_4$), an intermediate product in the catecholamine/dopamine biosynthesis.

In another embodiment the ratio between the expression levels of the TH and GCH1 of the present invention, is determined by measuring the amount of mRNA transcribed.

In another embodiment the ratio between the expression levels of the TH and GCH1 of the present invention, is determined by measuring the amount of protein expressed.

Tyrosine Hydroxylase

Tyrosine hydroxylase, abbreviated TH, is a monooxygenase that catalyzes the conversion of tyrosine to 3,4-dihydroxyphenylalanine (DOPA), a precursor of dopamine. TH activity is modulated by transcriptional and post-translational mechanisms in response to changes in the environment and to neuronal and hormonal stimuli. The most acute regulation of TH activity occurs through post-translational modification of the protein via phosphorylation.

As mentioned, the main function of tyrosine hydroxylase is the conversion of tyrosine to dopamine. TH is primarily found in dopaminergic neurons, but is not restricted to these. The TH gene is essential in embryonic development as the TH knock out genotype is lethal within embryonic day 14 in mice, whereas mice heterozygous for the TH mutation develops normally with only a slight decrease in catecholamine levels. The TH enzyme is highly specific, not accepting indole derivatives, which is unusual as many other enzymes involved in the production of catecholamines do. As the rate-limiting enzyme in the synthesis of catecholamines, TH has a key role in the physiology of adrenergic neurons. Catecholamines, such as dopamine, are major players in the signaling of said adrenergic neurons. Malfunction of adrenergic neurons gives rise to several neurodegenerative disorders in general, such as peripheral neuropathy, amyotrophic lateral sclerosis, Alzheimer's disease, Parkinson's disease, Huntington's disease, ischemic stroke, acute brain injury, acute spinal cord injury, nervous system tumors, multiple sclerosis, peripheral nerve trauma or injury, exposure to neurotoxins, metabolic diseases such as diabetes or renal dysfunctions and damage caused by infectious agents, or to mood disorders such as depression.

TH administered with the constructs and methods of the present invention may be used in treating Parkinson's disease.

The polynucleotide sequence encoding TH in the present invention is set forth in SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14. In a preferred embodiment, the present invention relates to SEQ ID NO. 7, SEQ ID NO. 8, SEQ ID NO. 9, SEQ ID NO. 10, SEQ ID NO. 11 and SEQ ID NO. 12 and sequence variants of the polynucleotide encoding the TH polypeptide comprising a sequence identity of at least 70% to said SEQ ID NOs., more preferably 75% sequence identity, for example at least 80% sequence identity, such as at least 85% sequence identity, for example at least 90% sequence identity, such as at least 95% sequence identity, for example at least 96% sequence identity, such as at least 97% sequence identity, for example at least 98% sequence identity, such as at least 99% sequence identity with the SEQ ID NO. 7, SEQ ID NO. 8, SEQ ID NO. 9, SEQ ID NO. 10, SEQ ID NO. 11 and SEQ ID NO. 12.

The polynucleotide, encoding TH, comprised in the vector construct of the present invention may also encode biologically active fragments or variants of the TH polypeptide.

In a preferred embodiment, such fragments or variants of the TH polynucleotide encoded by the present invention comprise at least 50 contiguous amino acids, such as 75 contiguous amino acids, for example 100 contiguous amino acids, such as 150 contiguous amino acids, for example 200 contiguous amino acids, such as 250 contiguous amino acids, for example 300 contiguous amino acids, such as 350 contiguous amino acids, for example 400 contiguous amino acids, such as 450 contiguous amino acids, wherein any amino acid specified in the sequence in question is altered to a different amino acid, provided that no more than 15 of the amino acids in said fragment or variant are so altered.

Mutated and substituted versions of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14 and the encoded TH polypeptide of the present invention are also covered. In one embodiment, the substitutions in the amino acid sequence are conservative, wherein the amino acid is substituted with another amino acid with similar chemical and/or physical characteristics. Mutations may occur in one or more sites within SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14 and or in the encoded TH polypeptide. In a preferred embodiment, the present invention relates to any mutation that renders TH biologically active, such as for example neutral mutations or silent mutations. In a more preferred embodiment, the present invention relates to mutations, wherein one or more of the serine residues S8, S19, S31, S40 or S404 have been altered.

In one embodiment, the biologically active fragment expressed by the vector construct according to the present invention comprises at least 50 contiguous amino acids, wherein any amino acid specified in the selected sequence is altered to a different amino acid, provided that no more than 15 of the amino acid residues in the sequence are so altered.

In one embodiment, the tyrosine hydroxylase (TH) polypeptide expressed by the vector construct according to the present invention is at least is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, more preferably at least 75% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, more preferably at least 80% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, more preferably at least 85% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, more preferably at least 90% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, more preferably at least 95% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, more preferably at least 96% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, more preferably at least 97% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, more preferably at least 98% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, more preferably at least 99% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14, more preferably 100% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14.

In one embodiment, the biologically active fragment expressed by the vector construct according to the present invention is the catalytic domain of tyrosine hydroxylase.

In one embodiment, the biologically active fragment expressed by the vector construct according to the present invention is a mutated tyrosine hydroxylase polypeptide, wherein one or more of the residues S19, S31, S40 or S404 have been altered to another amino acid residue.

GTP-Cyclohydrolase 1

GTP-cyclohydrolase I (GCH 1) is a member of the GTP cyclohydrolase family of enzymes. GCH 1 is part of the folate and biopterin biosynthesis pathways. GCH 1 is the first and rate-limiting enzyme in tetrahydrobiopterin ($BH_4$) biosynthesis, catalyzing the conversion of GTP into 7,8-DHNP-3'-TP. $BH_4$ is an essential cofactor required by the aromatic amino acid hydroxylase (AAAH) in the biosynthesis of the monoamine neurotransmitters serotonin (5-hydroxytryptamine (5-HT), melatonin, dopamine, noradrenaline, and adrenaline. Mutations in this gene are associated with malignant phenylketonuria and hyperphenylalaninemia, as well as L-DOPA-responsive dystonia. Several alternatively spliced transcript variants encoding different isoforms have been described; however, not all of the variants give rise to a functional enzyme.

GCH 1 has a number of clinical implications, involving several disorders. Defects in GCH1 are the cause of GTP cyclohydrolase 1 deficiency (GCH1D; also known as atypical severe phenylketonuria due to GTP cyclohydrolase I deficiency. GCH1D is one of the causes of malignant hyperphenylalaninemia due to tetrahydrobiopterin deficiency. It is also responsible for defective neurotransmission due to depletion of the neurotransmitters dopamine and serotonin, resulting in diseases such as Parkinson's disease. The principal symptoms include: psychomotor retardation, tonicity disorders, convulsions, drowsiness, irritability, abnormal movements, hyperthermia, hypersalivation, and difficulty swallowing. Some patients may present a phenotype of intermediate severity between severe hyperphenylalaninemia and mild dystonia type 5 (dystonia-parkinsonism with diurnal fluctuation). In this intermediate phenotype, there is marked motor delay, but no mental retardation and only minimal, if any, hyperphenylalaninemia. Defects in GCH1 are the cause of dystonia type 5 (DYT5); also known as progressive dystonia with diurnal fluctuation, autosomal dominant Segawa syndrome or dystonia-parkinsonism with diurnal fluctuation. DYT5 is a DOPA-responsive dystonia.

Dystonia is defined by the presence of sustained involuntary muscle contractions, often leading to abnormal postures. DYT5 typically presents in childhood with walking problems due to dystonia of the lower limbs and worsening of the dystonia towards the evening. It is characterized by postural and motor disturbances showing marked diurnal fluctuation. Torsion of the trunk is unusual. Symptoms are alleviated after sleep and aggravated by fatigue and exercise. There is a favorable response to L-DOPA without side effects.

GCH 1 administered with the constructs and methods of the present invention may be used in treating Parkinson's disease.

The polynucleotide sequence encoding GCH 1 in the present invention is set forth in SEQ ID NO. 1, SEQ ID NO. 2, SEQ ID NO. 3, SEQ ID NO. 4, SEQ ID NO. 5 and SEQ ID NO. 6. In a preferred embodiment, the present invention relates to SEQ ID NO. 1, SEQ ID NO. 2, SEQ ID NO. 3 and SEQ ID NO. 4 and sequence variants of the polynucleotide encoding the GCH 1 polypeptide comprising a sequence identity of at least 70% to SEQ ID NO. 1, SEQ ID NO. 2, SEQ ID NO. 3 and SEQ ID NO. 4, more preferably 75% sequence identity, for example at least 80% sequence identity, such as at least 85% sequence identity, for example at least 90% sequence identity, such as at least 95% sequence identity, for example at least 96% sequence identity, such as at least 97% sequence identity, for example at least 98% sequence identity, such as at least 99% sequence identity with the SEQ ID NO. 1, SEQ ID NO. 2, SEQ ID NO. 3 and SEQ ID NO. 4.

The polynucleotide, encoding GCH 1, comprised in the vector construct of the present invention may also encode biologically active fragments or variants of the GCH 1 polypeptide.

In a preferred embodiment, such fragments or variants of the GCH 1 polynucleotide encoded by the present invention comprise at least 50 contiguous amino acids, such as 75 contiguous amino acids, for example 100 contiguous amino acids, such as 150 contiguous amino acids, for example 200 contiguous amino acids, such as 250 contiguous amino acids, wherein any amino acid specified in the sequence in question is altered to a different amino acid, provided that no more than 15 of the amino acids in said fragment or variant are so altered.

Mutated and substituted versions of SEQ ID NO. 1, SEQ ID NO. 2, SEQ ID NO. 3, SEQ ID NO. 4, SEQ ID NO. 5 and SEQ ID NO. 6 and the encoded GCH 1 polypeptide of the present invention are also covered. In one embodiment, the substitutions in the amino acid sequence are conservative, wherein the amino acid is substituted with another amino acid with similar chemical and/or physical characteristics. Mutations may occur in one or more sites within SEQ ID NO. 1, SEQ ID NO. 2, SEQ ID NO. 3, SEQ ID NO. 4, SEQ ID NO. 5 and SEQ ID NO. 6 and or in the encoded GCH 1 polypeptide. In a preferred embodiment, the present invention relates to any mutation that renders GCH 1 biologically active, such as for example neutral mutations or silent mutations.

In one embodiment, the biologically active fragment expressed by the vector construct according to the present invention comprises at least 50 contiguous amino acids, wherein any amino acid specified in the selected sequence is altered to a different amino acid, provided that no more than 15 of the amino acid residues in the sequence are so altered.

In one embodiment, the GTP-cyclohydrolase 1 (GCH1) polypeptide expressed by the vector construct according to the present invention is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, more preferably at least 75% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, more preferably at least 80% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, more preferably at least 85% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, more preferably at least 90% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, more preferably at least 95% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, more preferably at least 96% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, more preferably at least 97% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, more preferably at least 98% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, more preferably at least 99% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, more preferably 100% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6.

Target Tissues for Treatment of Neurodegenerative Disorders

One challenge in the treatment of neurodegenerative diseases is to apply the medicament locally to avoid abundant side effects. Currently, most medicaments for treating brain disorders are administered in a way, most often orally, so that they reach the whole brain. Moreover, when delivered orally the medicaments will reach the target areas in a pulsatile fashion where fluctuating levels may pose a problem to the patient. An important parameter for in vivo gene therapy is the selection of a suitable target tissue. For the treatment of Parkinson's disease, the putamen and caudate nucleus is of particular interest. More specifically, the treatment should be centered on the dopaminergic neurons of the pars compacta region in the substantia nigra.

In Parkinson's disease, it is believed that the dyskenesia that often follows prolonged treatment with the current drug-of-choice, L-dopa, is a result of fluctuating levels of the drug in the brain.

One approach that has been tested in preclinical animal models of Parkinson's disease is to refine the dopamine replacement strategy by using a gene therapy approach where dopamine replacement can be conducted locally in the putamen and caudate nucleus where the dopamine deficiency is most advanced. This approach is referred to as the "enzyme replacement strategy". The rationale for this treatment stems from clinical observations in PD patients, which suggested that severe dyskinesias, induced by oral L-DOPA medication, could be alleviated by L-DOPA infused either via the intravenous or duodenal route. Thus, the current hypothesis is that dyskinesias develop, at least in part, due to the intermittent, pulsatile supply of DA that the oral L-DOPA delivery paradigm gives rise to.

Instead of supplying dopamine or L-dopa, gene therapy enables regulation of the enzymes that produces dopamine.

Thus, in a particular embodiment of the present invention polynucleotides encoding the TH and GCH 1 enzymes are delivered into the brain of an individual to be treated for Parkinson's disease. In a preferred embodiment, said polynucleotides are delivered in a single AAV vector. In a more preferred embodiment, said vector comprising said polynucleotides is delivered into the brain of said individual, preferably in the caudate nucleus and/or the putamen. In a yet more preferred embodiment, said vector is delivered so that it is effective in the dopaminergic neurons of the pars compacta region in the substantia nigra.

Dosing and Delivery Protocol

Figure 7:
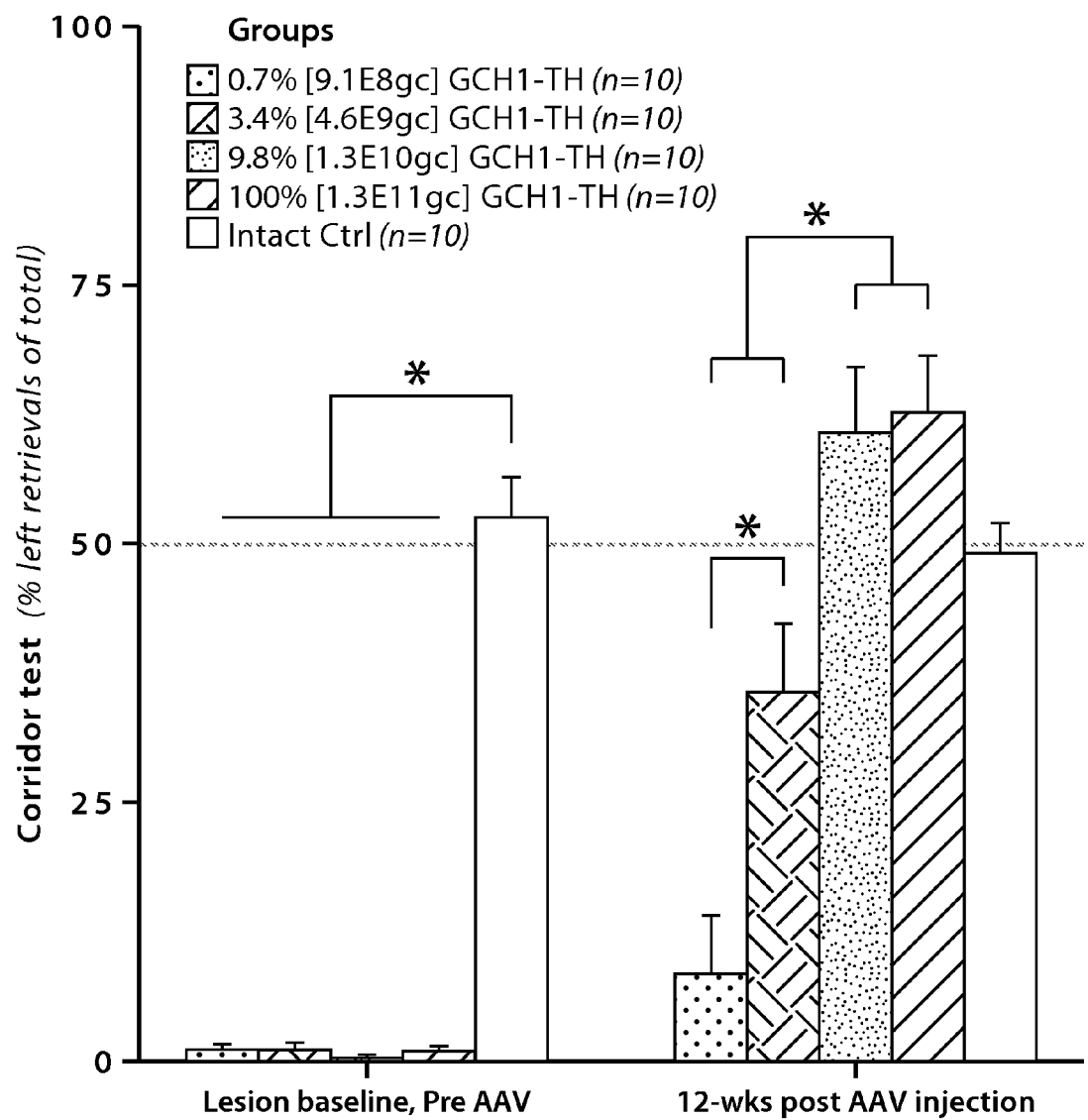
FIG. 7: Dose-response relationship with regards to recovery of motor function. Animals with a complete, unilateral DA denervation were tested in the corridor test prior to AAV injection (termed Lesion baseline). Thereafter, they were balanced into four groups based on their performance. All lesioned animals then received a stereotactic injection with equal volume of rAAV5-TH:GCH1 vector [5 μl] but with increasing concentration. This resulted in the following four dose groups; 0.7% [9.1E8 gc], 3.4% [4.6E9gc], 9.8% [1.3E10gc], 100% [1.3E11gc]. An equal sized intact, age matched, control group was included as reference at all time-points. The animals were then re-tested in the corridor test at 12 weeks post AAV injection. Complete recovery was seen in the two treatment groups that received the higher vector concentrations, i.e., down to a dose of 1.3E10gcrAAV5-TH:GCH1.4.6E9gc vector resulted in 50% recovery, whereas the recovery from the 9.1E8 gcdose was significantly lower.*=significant difference in a two-way factorial ANOVA followed by Tukey's HSD post-hoc test.

An important parameter is the dosage of TH and GCH 1 to be delivered into the target tissue. In this regard, "unit dosage" refers generally to the concentration of TH and GCH 1/ml of TH and GCH 1 composition. For viral vectors, the TH and GCH 1 concentration may be defined by the number of viral particles/ml of neurotrophic composition. Optimally, for delivery of TH and GCH 1 using a viral expression vector, each unit dosage of TH and GCH 1 will comprise 2.5 to 25 µL of a TH and GCH 1 composition, wherein the composition includes a viral expression vector in a pharmaceutically acceptable fluid and provides from $10^{10}$ up to $10^{15}$ TH and GCH 1 expressing viral particles per ml of TH and GCH 1 composition (exemplified in FIG. 7) Such high titers are particularly useful for adeno-associated virus, such as the AAV vector described in the present invention. Example 2 describes a dosage regime of the vector of the present invention.

In one embodiment the dosage of the vector administered to a patient in need thereof is between 1.5E+10 and 2.2E+12 vector genome copies per milliliter putaminal grey matter.

In another embodiment the dosage of the vector for use in the preparation of a medicament for the treatment of a catecholamine dysfunction is between 1.5E+10 and 2.2E+12 vector genome copies per milliliter putaminal grey matter of the individual to whom the vector is intended for administration.

In a preferred embodiment, the administration site is the striatum of the brain, in particular the caudate nucleus and/or the putamen. Injection into the putamen can label target sites located in various distant regions of the brain, for example, the globus pallidus, amygdala, subthalamic nucleus or the substantia nigra. In a preferred embodiment the (or one of the) target site(s) is the substantia nigra, more preferably the pars compacta region in the substantia nigra. Injection may also be into both the striatum and the substantia nigra.

Within a given target site, the vector system may transduce a target cell. The target cell may be a cell found in nervous tissue, such as a neuron, astrocyte, oligodendrocyte, microglia or ependymal cell. In a preferred embodiment, the target cell is a neuron, in particular a dopaminergic neuron of the pars compacta region in the substantia nigra.

The vector system is preferably administered by direct injection. Methods for injection into the brain (in particular the striatum) are well known in the art (Bilang-Bleuel et al (1997) Proc. Acad. Natl. Sci. USA 94:8818-8823; Choi-Lundberg et al (1998) Exp. Neurol. 154:261-275; Choi-Lundberg et al (1997) Science 275:838-841; and Mandel et al (1997)) Proc. Acad. Natl. Sci. USA 94:14083-14088). Stereotaxic injections may be given.

Those of skill in the art will appreciate that the direct delivery method employed by the invention obviates a limiting risk factor associated with in vivo gene therapy. In the invention, delivery is direct and the delivery sites are chosen so diffusion of secreted Th and GCH 1 takes place over a controlled and pre-determined region of the brain to optimise contact with targeted neurons, while minimizing contact with non-targeted cells.

Modifications of the vector capsid properties could enable targeting of the vector to the striatal region also after intrathecal (IT) injection or injection into the cerebral ventricles (ICV). This may be achieved by modification of specific domains of the capsid. For example, mutation of the amino acid at position 587 may remove the HSPG binding affinity of AAV serotype 2 and open up for binding to other cell surface residues that may be cell type specific. Another alternative approach is to generate chimeric AAV serotypes that would inherit different binding properties from the two serotypes mixed.

Pharmaceutical Preparations

To form a TH and GCH 1 composition for use in the invention, TH and GCH 1 encoding expression viral vectors may be placed into a pharmaceutically acceptable suspension, solution or emulsion. Suitable mediums include saline and liposomal preparations.

More specifically, pharmaceutically acceptable carriers may include sterile aqueous of non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils.

Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like. Further, a composition of TH and GCH 1 transgenes may be lyophilized using means well known in the art, for subsequent reconstitution and use according to the invention. A colloidal dispersion system may also be used for targeted gene delivery.

Colloidal dispersion systems include macromolecule complexes, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (LUV), which range in size from 0.2-4.0 μm can encapsulate a substantial percentage of an aqueous buffer containing large macro molecules. RNA, DNA and intact virions can be encapsulated within the aqueous interior and be delivered to cells in a biologically active form (Fraley, et al., Trends Biochem. Sci., 6: 77, 1981). In addition to mammalian cells, liposomes have been used for delivery of operatively encoding transgenes in plant, yeast and bacterial cells. In order for a liposome to be an efficient gene transfer vehicle, the following characteristics should be present: (1) encapsulation of the genes encoding the TH and GCH 1 at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6: 682, 1988).

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries.

Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted gene delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Thus in one aspect, the present invention relates to a pharmaceutical composition for use in a method of treatment of Parkinson's Disease, said composition comprising a one-vector expression system and a formulation for delivering said vector to the basal ganglia, wherein said one-vector expression system comprises a) a first and a second expression cassette, said first expression cassette comprising a nucleotide sequence comprising a first promoter sequence operably linked to a first nucleotide sequence, said first nucleotide sequence encodes a GTP-cyclohydrolase 1 (GCH1) polypeptide or a biologically active fragment or variant thereof, and wherein said second expression cassette comprising a nucleotide sequence comprising a second promoter sequence operably linked to a second nucleotide sequence encoding a tyrosine hydroxylase (TH) polypeptide or a biologically active fragment or variant thereof, with the proviso that said vector does not comprise a nucleotide sequence encoding an aromatic amino acid decarboxylase (AADC) polypeptide, or b) a first and a second expression cassette, said first expression cassette comprising a nucleotide sequence comprising a first promoter sequence operably linked to a first nucleotide sequence, said first nucleotide sequence encodes a GTP-cyclohydrolase 1 (GCH1) polypeptide or a biologically active fragment or variant thereof, and wherein said second expression cassette comprises a nucleotide sequence comprising a second promoter sequence operably linked to a second nucleotide sequence encoding a tyrosine hydroxylase (TH) polypeptide or a biologically active fragment or variant thereof, wherein the vector is an adeno associated vector (AAV), or c) an expression cassette comprising a promoter, a first nucleotide sequence, a translation initiating nucleotide sequence such as an internal ribosome entry site (IRES) and a second nucleotide sequence, wherein said promoter is operably linked to said first nucleotide sequence, and wherein said translation initiating nucleotide sequence is linking said first and said second nucleotide sequence, wherein said first nucleotide sequence encodes a GTP-cyclohydrolase 1 (GCH1) polypeptide or a biologically active fragment or variant thereof, and wherein said second nucleotide sequence encodes a tyrosine hydroxylase (TH) polypeptide or a biologically active fragment or variant thereof, or d) an expression cassette comprising a first nucleotide sequence, a translation initiating nucleotide sequence such as an internal ribosome entry site (IRES) and a second nucleotide sequence wherein said translation initiating nucleotide sequence is linking said first and said second nucleotide sequence, and wherein the sequence comprising said first nucleotide sequence linked to said translation initiating nucleotide sequence linked to said second nucleotide sequence is flanked by 5' and 3' terminal repeats, and wherein said first nucleotide sequence encodes a GTP-cyclohydrolase 1 (GCH1) polypeptide or a biologically active fragment or variant thereof, and wherein said second nucleotide sequence encodes a tyrosine hydroxylase (TH) polypeptide or a biologically active fragment or variant thereof, wherein said terminal repeats comprise a sequence capable of directing the expression of an operably linked polypeptide.

In one embodiment of the present invention the GTP-cyclohydrolase 1 (GCH1) polypeptide or the biologically active fragment or variant thereof, expressed by said first expression cassette, is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein the tyrosine hydroxylase (TH) polypeptide or the biologically active fragment or variant thereof, expressed by said second expression cassette is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14.

In one embodiment of the present invention the GTP-cyclohydrolase 1 (GCH1) polypeptide or the biologically active fragment or variant thereof expressed by, wherein said polypeptide or a biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein said tyrosine hydroxylase (TH) polypeptide or a biologically active fragment or variant thereof, expressed by said second expression cassette is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14.

In one embodiment of the present invention the GTP-cyclohydrolase 1 (GCH1) polypeptide or the biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5, SEQ ID NO. 6, and wherein the encoded tyrosine hydroxylase (TH) polypeptide or the biologically active fragment or variant thereof is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14.

In one embodiment of the present invention the GTP-cyclohydrolase 1 (GCH1) polypeptide or the biologically active fragment or variant thereof is at least 70% identical to a polypeptide selected from the group consisting of SEQ ID NO. 1, SEQ ID NO. 2, SEQ ID NO. 3, SEQ ID NO. 4, SEQ ID NO. 5 and SEQ ID NO. 6, and wherein the encoded tyrosine hydroxylase (TH) polypeptide or the biologically active fragment or variant thereof, is at least 70% identical to a polypeptide selected from the group consisting of SEQ ID NO. 7, SEQ ID NO. 8, SEQ ID NO. 9, SEQ ID NO. 10, SEQ ID NO. 11, SEQ ID NO. 12 SEQ ID NO. 13 and SEQ ID NO. 14.

In one embodiment of the present invention the pharmaceutical composition as defined herein above comprises manitol, heparin or gadolinium based MRI contrast agents.

In another embodiment the pharmaceutical composition as defined herein above comprises trophic factors or reversible proteasome inhibitors.

Medical Use and Methods of Treatment

In one aspect the vector of the present invention, is used as a medicament.

In one aspect, the present invention relates to the use of the vector as defined herein above, for the preparation of a medicament for the treatment of a disease associated with catecholamine dysfunction.

In one aspect, the present invention relates to the vector as defined herein above, for use in a method of treatment of a disease associated with catecholamine dysfunction.

In one aspect, the present invention relates to a method of treating a disease associated with catecholamine dysfunction, in a patient in need thereof, said method comprising administering to said individual the vector as defined herein above.

In one embodiment of the present invention, the catecholamine dysfunction is catecholamine deficiency.

In a further embodiment of the present invention, the catecholamine dysfunction is catecholamine excess.

In one preferred embodiment, the catecholamine deficiency is dopamine deficiency.

In another embodiment the catecholamine excess is dopamine excess.

In one embodiment said disease associated with catecholamine dysfunction is a disease, disorder or damage of the central and/or peripheral nervous system.

In a further embodiment, said disease, disorder or damage of the central and/or peripheral nervous system is a neurodegenerative disorder.

In another embodiment, said disease associated with catecholamine dysfunction is a disease of the basal ganglia.

In one embodiment the disease treatable by using the vector of the present invention is selected from the group consisting of Parkinson's Disease (PD), DOPA responsive dystonia, ADHD, schizophrenia, depression, vascular parkinsonism, essential tremor, chronic stress, genetic dopamine receptor abnormalities, chronic opioid, cocaine, alcohol or marijuana use, adrenal insufficiency, hypertension, noradrenaline deficiency, post-traumatic stress disorder, pathological gambling disorder, dementia, Lewy body dementia.

In a preferred embodiment the neurodegenerative disorder treatable by using the vector of the present invention is Parkinson's Disease (PD).

In one aspect the invention relates to the use of the vector according to the invention for the preparation of a medicament for the treatment of a nervous system disorder. The nervous system disorder can be a disorder of the peripheral nervous system or the central nervous system.

By treatment is not only intended curative treatment but also preventive (not absolute prevention) or prophylactic treatment. Treatment may also be ameliorative (not absolute amelioration) or symptomatic.

Preferably the CNS disorder is a neurodegenerative or neurological disease, in one preferred embodiment of the invention the neurodegenerative disease is Parkinson's disease.

Nervous system diseases may be treated by administering to an individual in need thereof a therapeutically effective amount of the virus vector of the invention; or a therapeutically effective amount of the pharmaceutical composition of the invention.

Pharmaceutical Composition

Accordingly, in one aspect the present invention relates to a pharmaceutical composition comprising the vector as defined herein above, and a pharmaceutically acceptable carrier or diluent.

In one embodiment of the present invention the pH of the pharmaceutical composition as defined herein above is between pH 4 and pH 9.

In another embodiment the injection of the pharmaceutical composition is intracranial, intracerebral, intravenous, intravitreous, intranasal, intramuscular, intraspinal, intraperitoneal, subcutaneous, a bolus or a continuous administration.

In one embodiment said pharmaceutical composition is formulated for administration by injection, sublingual tablet or spray, cutaneous administration or inhalation.

In one embodiment the pharmaceutical composition as defined herein above is formulated for administration by injection, suppository, oral administration, sublingual tablet or spray, cutaneous administration, inhalation or for local administration using an implantable biocompatible capsule.

In a further embodiment the injection is intravenous, intramuscular, intraspinal, intraperitoneal, subcutaneous, a bolus or a continuous administration.

In one embodiment the pharmaceutical composition is administered at intervals of 30 minutes to 24 hours.

In another embodiment the pharmaceutical composition is administered at intervals of 1 to 6 hours.

In one embodiment of the present invention, wherein the duration of the treatment is from 6 to 72 hours.

In one important aspect of the present invention the duration of the treatment is life long.

In a further embodiment the pharmaceutical composition as defined herein above is formulated for administration by injection, suppository, oral administration, sublingual tablet or spray, cutaneous administration, inhalation or for local administration using an implantable biocompatible capsule.

In one embodiment the dosage of the active ingredient, i.e. the vector, in the pharmaceutical composition according to the present invention is between 10 µg and 500 mg per kg body mass, such as between 20 µg and 400 mg, e.g. between 30 µg and 300 mg, such as between 40 µg and 200 mg, e.g. between 50 µg and 100 mg, such as between 60 µg and 90 µg, e.g. between 70 µg and 80 µg.

In a further embodiment the pharmaceutical composition according to the present invention is administered at intervals of 72 hours to at least 7 days, such as 80 hourse, e.g. 96 h, such as 5 days, e.g. 6 days, such as once a week.

In a further embodiment the pharmaceutical composition according to the present invention is administered at intervals of 7 days to 1 month, such as once every two weeks, e.g. every 3 weeks.

Implantable Host Cells

In one aspect, the present invention relates to an isolated host cell comprising the vector as defined herein above.

In one aspect the invention relates to isolated host cells transduced with the vector according to the invention. These cells preferably are mammalian host cells because these are capable of secreting and processing the encoded TH and GCH 1 correctly.

Preferred species include the group consisting of rodent (mouse, rat), rabbit, dog, cat, pig, monkey, human being.

Examples of primary cultures and cell lines that are good candidates for transduction with the vectors of the present invention include the group consisting of CHO, HEK293, COS, PC12, HiB5, RN33b, neuronal cells, foetal cells, ARPE-19, MDX12, C2C12, HeLa, HepG2, striatal cells, neurons, astrocytes, interneurons.

In one embodiment the host cell of the present invention is selected from the group consisting of eukaryotic cells, preferably mammalian cells, more preferably primate cells, more preferably human cells.

In another embodiment, the host cell of the present invention is selected from the group consisting of Chinese hamster ovary cells, CHO-K1, baby hamster kidney cells, mouse fibroblast-3T3 cells, African green monkey cell lines, rat adrenal pheochromocytoma, AT3 cells, rat glial tumor cells, rat neuronal cells and rat hippocampal cells.

EXAMPLES

Example 1

The Effect of a Single rAAV Vector for Continued DOPA Delivery in an Animal Model of Parkinson's Disease Materials and Methods Experimental Design All rats in the experiment below (with the exception of animals in the intact control groups) received a unilateral injection of 6-OHDA into the medial forebrain bundle (MFB) to achieve a complete lesion of the nigrostriatal pathway. At four to five weeks post-lesion, all lesioned animals were screened in a rotation test after an amphetamine-induced rotation test [Ungerstedt and Arbuthnott: Quantitative recording of rotational behavior in rats after 6-hydroxy-dopamine lesions of the nigrostriatal dopamine system; *Brain Res* 1970 24 485-93]. Only animals exhibiting >6.0 full-body turns/min towards the DA depleted side were included in the study (n=54).

Figure 3:
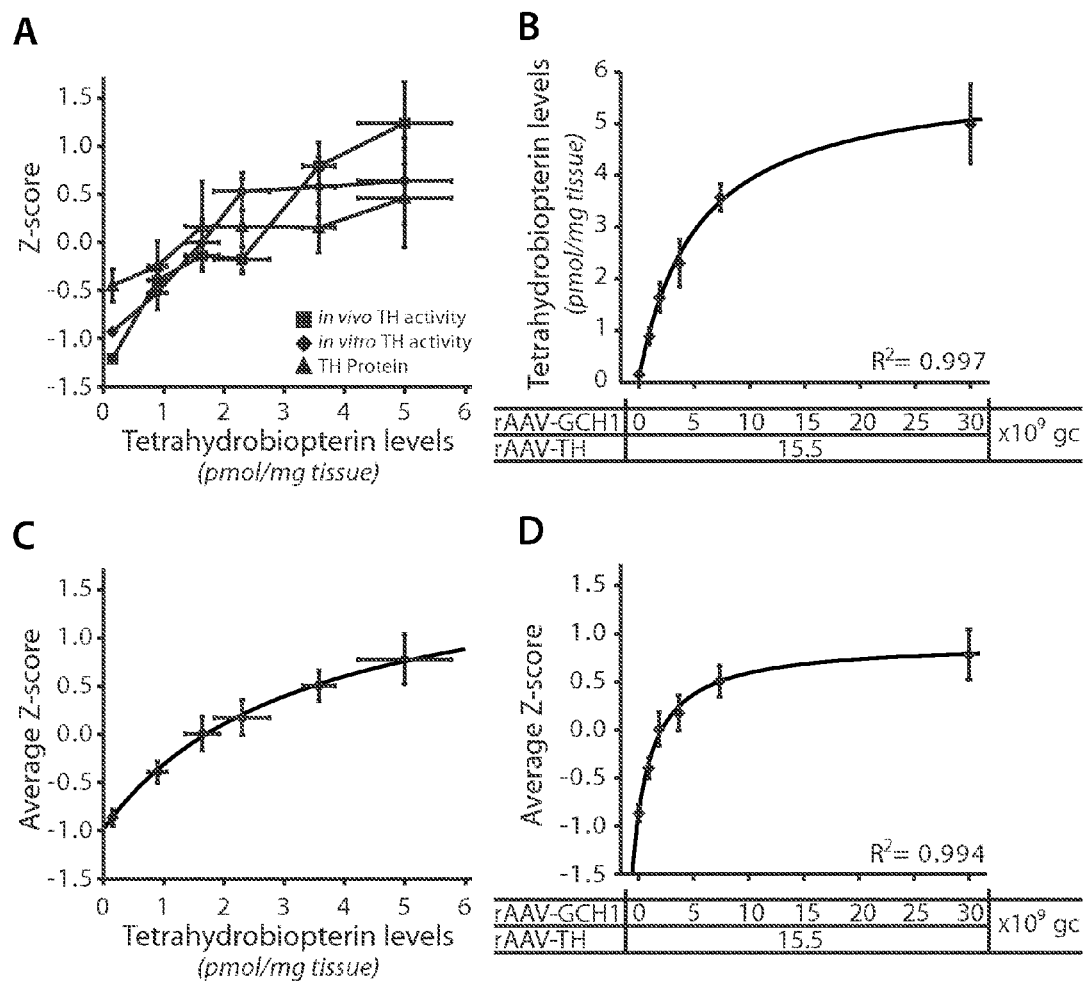
FIG. 3: Modelling of the BH4 and GCH1 dependency for TH function. Data values of the in vivo and in vitro TH enzyme activity measurements together with semi-quantitative western blots for TH protein measurements in the 6 groups where rAAV5-TH and rAAV5-GCH1 vectors were mixed in varying ratios were unified into a single readout variable by normalizing the quantities to Z-scores. This results in a dimensionless quantity that can then be directly compared and modelled. (a) Individual Z-scores of in vivo and in vitro TH enzyme activity and TH protein levels plotted as a function of BH4 synthesis in the DA depleted striatum after rAAV5-TH and rAAV5-GCH1 transduction. This operation revealed that the results from the three assays actually converged into one general pattern when plotted as a function of striatal BH4 levels. (b) Striatal BH4 levels plotted as a function of gc rAAV5-GCH1 injected. The BH4 levels in the striatum did not increasing linearly with increasing titers of rAAV5-GCH1, but instead showed a clear saturation at levels above 3.6E9 gc. (c) Grouping the Z-scores of the three tests of TH enzyme function into a single model, plotted as a function of striatal BH4 levels. (d) Average Z-scores of the three tests of TH function, plotted as a function of the genome copies of rAAV5-GCH1 injected. Solid lines in B-D represent the non-linear fit achieved after applying a saturation model $y=Ax/(B+x)+C$ using a modified Levenberg-Marquardt algorithm.
Figure 4:
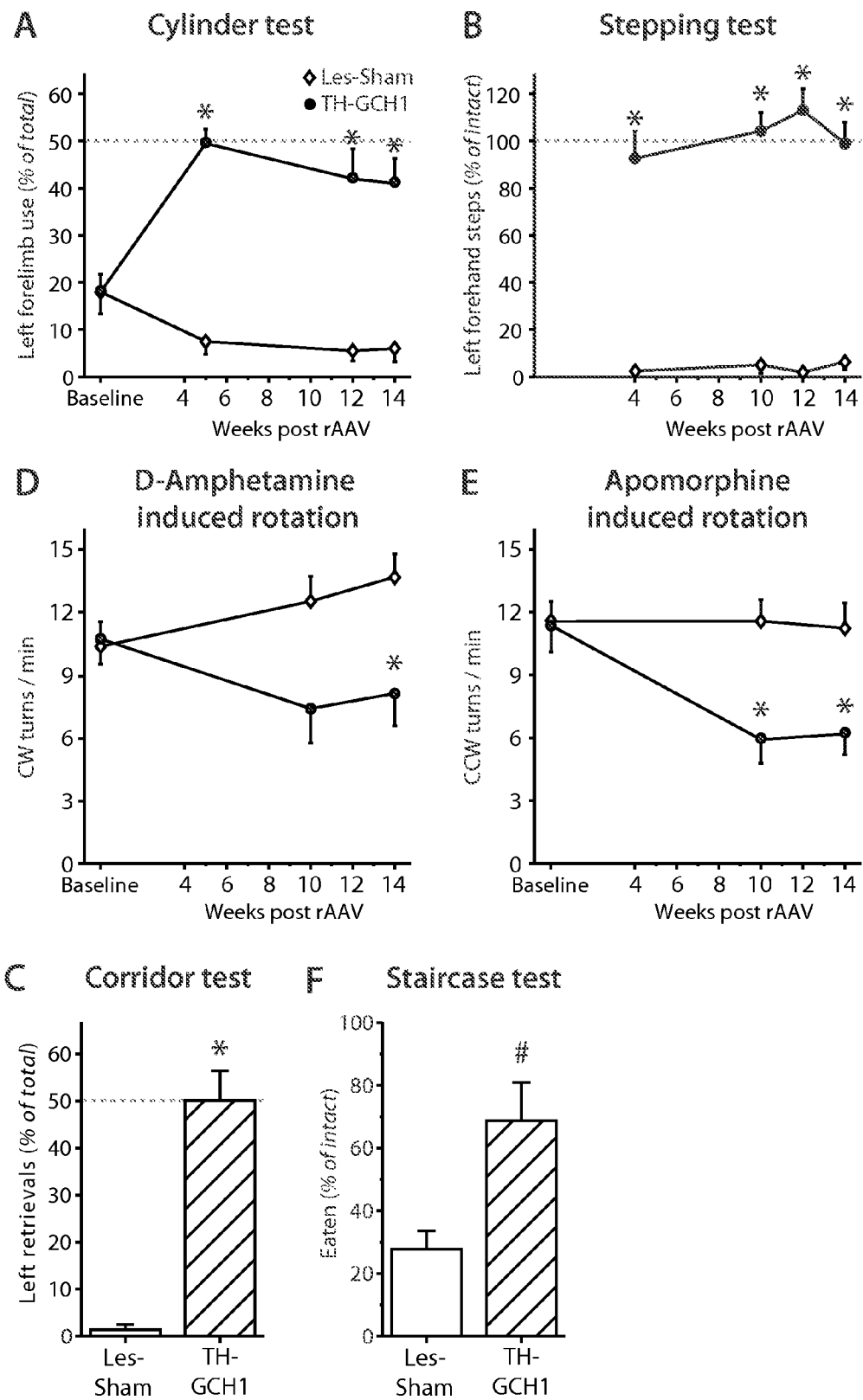
FIG. 4: Recovery of motor function. Animals with a complete, unilateral DA denervation were tested in a battery of behavioural tests. Based on their performance in the cylinder tests (a) and drug induced rotations (d,e) they either had a sham surgery (Les-Sham group) or receiver the therapeutic single rAAV vector (TH-GCH1). Complete recovery was seen in the TH-GCH1 group within 5 weeks in the cylinder test (a) and stepping test (b). This was maintained throughout the experiment. This was also seen in the corridor test (c) whereas the recovery was partial in amphetamine (d) and apomorphine (e) induced rotations. The recovery in complex motor function such as in the staircase test was also significant (f). *=significantly different from Les-Sham group.
Figure 5:
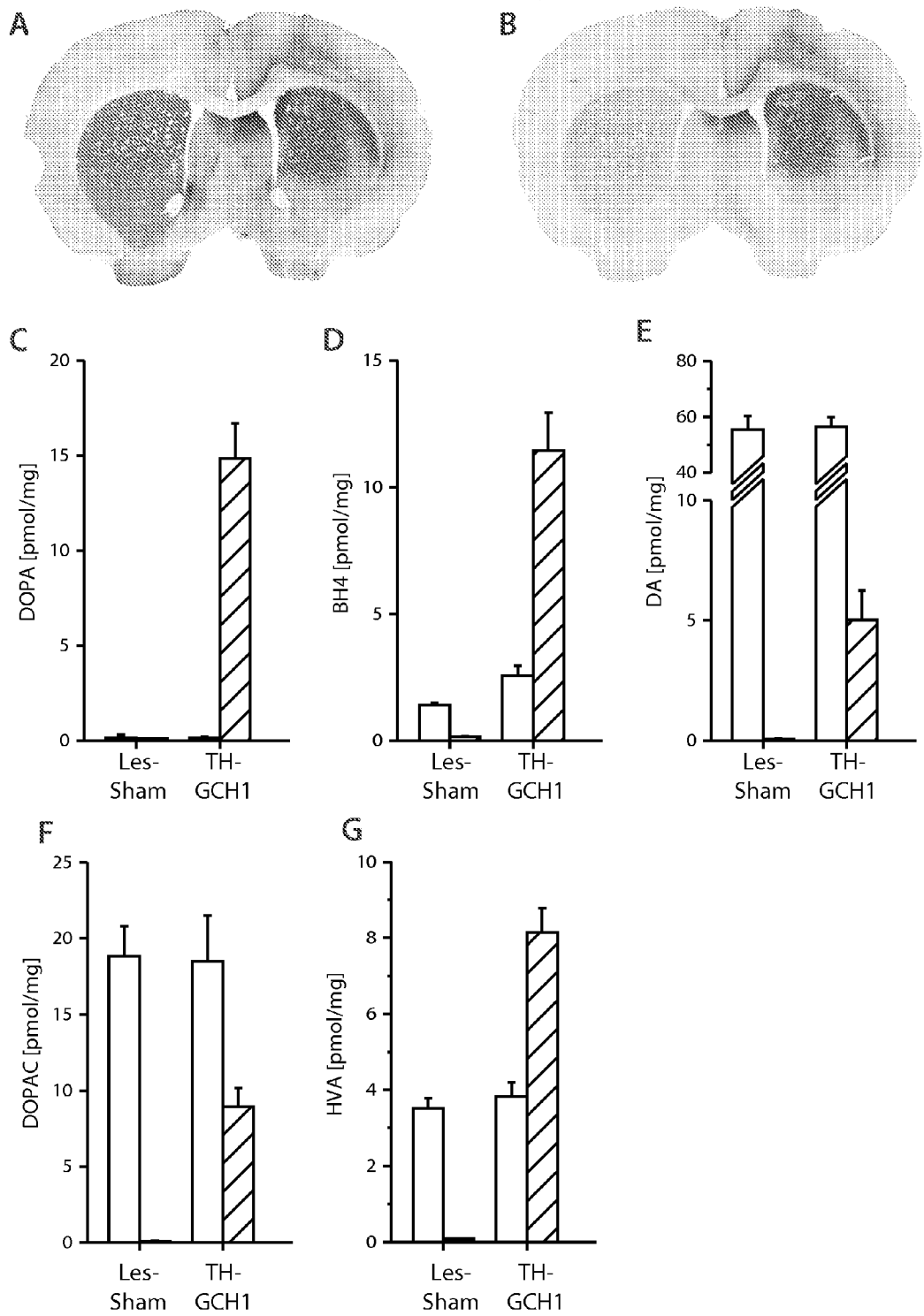
FIG. 5: Post mortem analysis of transgene expression and DA synthesis. Six month after rAAV injection into 6-OHDA lesioned animals the function of the single rAAV TH-GCH1 vector was evaluated biochemically and using immunohistochemistry. The immunohistochemistry revealed a robust expression of both TH (a) and GCH1 (b) transgenes. This expression was coupled to a very efficient production of both DOPA (closed bar in c) and BH4 (closed bar in d) to a much higher extent than in the intact striatum (open bar in d). Dopamine levels were also significantly reconstituted (e) and levels of the intermediary metabolite DOPAC restored to 50% of normal (f) and the end metabolite HVA (g) elevated to two time normal levels.

Twenty rats with a confirmed 6-OHDA lesion were balanced into two groups (Les-Sham and TH-GCH1) based on their performance in the cylinder tests and in amphetamine- and apomorphine-induced rotations (FIG. 3). At 6 weeks post lesion, the animals in the TH-GCH1 group received a stereotactic injection 3.5E10 gc rAAV5-TH:GCH1 vector and the control group received sham surgery, which involved opening the scalp and drilling a hole at the correct site but the dura was not penetrated. The animals were re-tested using the same drug-induced rotation tests at 5 and 10 weeks post-rAAV injection. At 5, 9 and 13 weeks post rAAV, the animals were scored in the same rotometer equipment without preceding pharmacological challenge (spontaneous rotation). The cylinder test was also repeated at 5, 12 and 14 weeks post-injection. To study the treatment effect on motor learning, sensorimotor integration as well as motor function, training in the stepping, staircase and corridor tests was initiated once the therapeutic effect of the treatment was well manifested. The stepping test was performed at 5, 10 and 12 weeks post-rAAV injection. The staircase test was performed as a single test session over 21 days between 22-24 weeks post-transduction. The animals were then subjected to the corridor test and killed at 28 weeks.

Forty rats with a confirmed 6-OHDA lesion were balanced into four groups based on their performance in the cylinder test, stepping test and corridor test. At 6 weeks post lesion, the animals a stereotactic injection with equal volume of rAAV5-TH:GCH1 vector [5 μl]. The four groups received vector preparations of increasing concentration resulting in the following four dose groups; 0.7% [9.1E8gc] GCH1-TH (n=10), 3.4% [4.6E9gc] GCH1-TH (n=10), 9.8% [1.3E10gc] GCH1-TH (n=10), 100% [1.3E11gc] GCH1-TH (n=10). An equal sized intact, age matched, control group was included as reference (n=10). The animals were Scored in the corridor test both at five weeks post 6-OHDA lesion (prior to AAV injection) and 12 wks post AAV.

Eight animals with a confirmed 6-OHDA lesion were divided into two groups (Les-Sham and TH-GCH1) based on their performance in the corridor and in amphetamine-induced rotation. The animals in the TH-GCH1 group received the stereotactic injection of the full titer AAV5-TH: GCH1 vector as described below and assessed using on-line microdialysis at a minimum of 6 months post AAV injection. All animals were decapitated and the brains were quickly removed and striatal tissue was dissected out and then snap-frozen for biochemical analysis. The midbrain was post-fixed in 4% paraformaldehyde (PFA) for validation of the 6-OHDA lesion.

Vector Construction

Figure 1B:
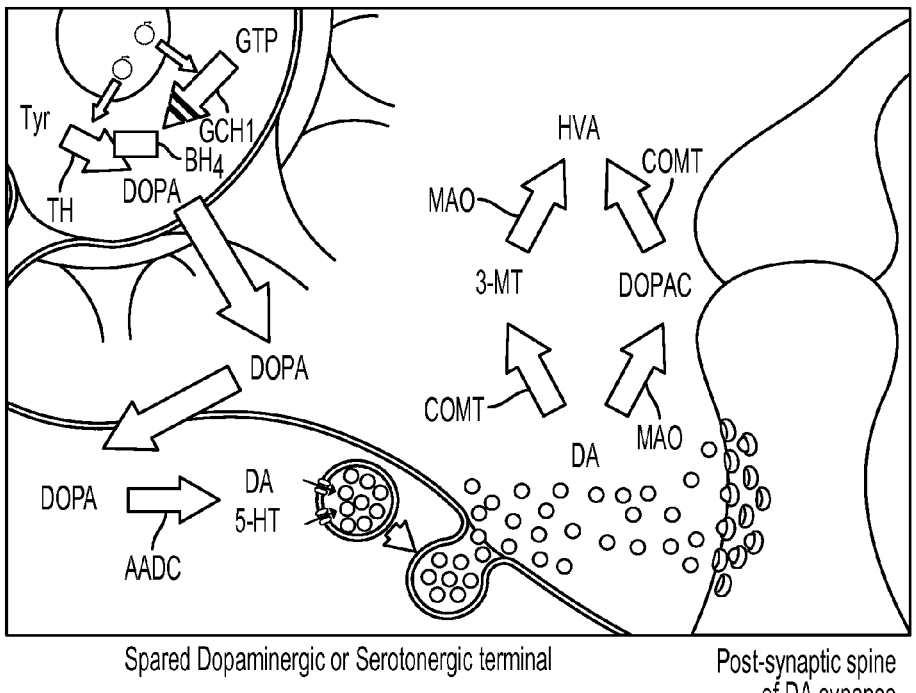

The viral vectors utilized in this study were pseudotyped rAAV2/5 vectors, where the transgene of interest is flanked by inverted terminal repeats of the AAV2 packaged in an AAV5 capsid (herein referred to as simply rAAV). In this invention, a novel plasmid expressing both the transgenes TH and GCH1 was constructed. Here, two expression cassettes were fused into a single AAV2 plasmid. TH and GCH1 were expressed under the human Synapsin 1 (Syn-1) promoter. The GCH1 gene was followed by a late SV40 poly-A sequence that then preceded the second Syn-1 promoter controlling the expression of the TH gene. To achieve a superior expression of the TH gene over GCH1, the trafficking of the TH mRNA was improved by the addition of a woodchuck hepatitis virus post-transcriptional regulatory element (WPRE). The full sequence was terminated by an early SV40 poly-A sequence (FIG. 1). The rAAV vectors were produced using a double-transfection method with the appropriate transfer plasmid and the helper plasmid containing the essential adenoviral packaging genes as described previously [Grimm et al: Novel tools for production and purification of recombinant adenoassociated virus vectors; *Hum Gene Ther* 1998 18 2745-60; Hauswirth et al: Production and purification of recombinant adeno-associated virus; *Meth Enzymol* 2000 316 743-61]. They were thereafter purified by iodixanol step gradients and Sepharose Q column chromatography, as described in detail elsewhere [Ulusoy et al: Dose Optimization for Long-term rAAV-mediated RNA Interference in the Nigrostriatal Projection Neurons; *Mol Ther* 2009 17 1574-84]. The purified viral vector suspension was titered using TaqMan quantitative PCR as described elsewhere [Ulusoy et al: Dose Optimization for Long-term rAAV-mediated RNA Interference in the Nigrostriatal Projection Neurons; *Mol Ther* 2009 17 1574-84]), but with primers and probe targeted towards the WPRE sequence. The final titer of the injected vector suspension was 1.0E13 gc/m Surgical Procedures All surgical procedures were conducted under anesthesia induced by a 20:1 mixture of Fentanyl and Dormitor (Apoteksbolaget, Sweden) injected i.p. at a total volume of approx. 6 ml/kg. The injections were conducted using a 10 μl Hamilton syringe with the animal mounted in a stereotactic frame (Stoelting, Wood Dale, Ill.). The anteroposterior (AP) and mediolateral (ML) coordinates were calculated from bregma and the dorsoventral (DV) coordinates from the dural surface [Watson and Paxinos: The rat brain in stereotaxic coordinates. *Academic Press San Diego* 1986].

6-OHDA lesions. The animals received 6-OHDA (Sigma-Aldrich AB, Sweden) injections into the right MFB (14 μg free base in ascorbate-saline (0.02%) injected at a concentration of 3.5 μg/μl) in order to achieve a complete lesion of the nigrostriatal pathway [Ungerstedt and Arbuthnott: Quantitative recording of rotational behavior in rats after 6-hydroxy-dopamine lesions of the nigrostriatal dopamine system. *Brain Res* 1970 24 485-93]. The injection was conducted at the following coordinate: AP: −4.4 mm; ML: −1.2 mm and DV: −7.8 mm with the tooth bar set to −2.4 mm [Carlsson et al: Serotonin neuron transplants exacerbate L-DOPA-induced dyskinesias in a rat model of Parkinson's disease; *J Neurosci* 2007 27 8011-22]. The injection was performed with a 26-gauge needle attached to the Hamilton syringe at an injection speed of 1 μl/min and the needle kept in place for an additional 3 min before it was slowly retracted.

rAAV vector injections. The animals in the vector treatment group received a stereotactic injection of 5 μl rAAV5 vectors in ringer lactate suspension. The injections were performed as one 1.5 μl and one 1 μl deposit along each of two needle tracts at the following coordinates: (1) AP: +1.0 mm; ML: −2.6 mm and DV: −4.5, −3.5 mm and (2) AP: 0 mm; ML: −3.2 mm and DV: −5.0, −4.0 mm with the tooth bar set at −2.4 mm. The injection was performed using a pulled glass capillary (outer diameter 60-80 μm diameter) mounted on a 22 s gauge needle attached to the Hamilton syringe. The injection rate was 0.4 μl/min and the needle kept in place for 1 min after the first deposit and 3 min after the second deposit was delivered and then before it was slowly retracted from the brain parenchyma.

Behavioural Tests

Drug-induced rotation was assessed measuring left and right full body turns using automated rotometer bowls (AccuScan Instruments Inc., Columbus, Ohio) after either injection of D-amphetamine sulfate (2.5 mg/kg, ip; Apoteksbolaget, Sweden) or apomorphine-HCl (0.05 mg/kg, sc; Sigma-Aldrich AB, Sweden) and monitored for 90 and 40 min, respectively. Rotational asymmetry scores are expressed as net 360° turns/min and ipsilateral rotations (i.e. toward the injected side) were assigned a positive value.

Cylinder test assessing forelimb use asymmetry was conducted essentially as described by [Kirik et al: Growth and functional efficacy of intrastriatal nigral transplants depend on the extent of nigrostriatal degeneration; *J Neurosci* 2001 21 2889-96] with minor modifications from [Schallert and Tillerson: Innovative models of cns disease: from molecule to therapy. Intervention strategies for degeneration of dopamine neurons in parkinsonism: optimising behavioral assessment of outcome; 1999 131-51]. The rats were placed individually in a 20 cm glass cylinder and allowed to move freely while being recorded with a digital video camera. Two perpendicular mirrors were placed behind the glass cylinder that allowed the complete surface of the cylinder to be clearly visible on the screen. The animals were left in the cylinder until at least 20 touches on the cylinder wall were observed. Forelimb placement and use on the cylinder wall during this exploratory phase was then scored off-line using frame-by-frame analysis by an observer blinded to the group identity of the animals. The paw used during 20 contacts with the cylinder walls during rearing was scored and presented as left forepaw touches as a percentage of the total number of touches. In this test, normal animals would score on average 50%.

Stepping (forelimb akinesia) test. Forelimb akinesia was assessed by an investigator blinded to the group identity of the individual rats using the stepping test initially described by [Schallert et al: Excessive bracing reactions and their control by atropine and L-DOPA in an animal analog of Parkinsonism; Exp Neurol 1979 64 33-43], modified to a side-stepping test by [Olsson et al: Forelimb akinesia in the rat Parkinson model: differential effects of dopamine agonists and nigral transplants as assessed by a new stepping test; J Neurosci 1995 15 3863-75] and deployed as previously described [Winkler et al: L-DOPA-induced dyskinesia in the intrastriatal 6-hydroxydopamine model of parkinson's disease: relation to motor and cellular parameters of nigrostriatal function; Neurobiol Dis 2002 10 165-86]. Briefly, the investigator firmly held the rat using both hands lifting the hind paws and one forepaw off the table but enabling the unrestrained paw to contact the table surface. The animal was then moved over a defined distance of 90 cm across the table surface at a slow constant pace over 5 s. The investigator scored the numbers of adjusting side steps in both forehand and backhand direction twice, and the average was calculated. The animals were trained for 4 days during the third week post 6-OHDA-lesion. The average score of days 5-7, when the animals had reached a stable baseline performance, formed the final dependent variable. The data from this time point constituted the pre-treatment baseline score. Thus, the average of the three last days was used as a pre-treatment performance score. At the three following test sessions, 6-, 9- and 12-weeks post-rAAV injection, the animals were first habituated to the test for one or two days and then assessed for three consecutive days.

Staircase test was used to assess the skilled forelimb reaching and grasping abilities by employing a modified version of the original test design described by [Montoya et al: The "staircase test": a measure of independent forelimb reaching and grasping abilities in rats; J Neurosci Methods 1991 36 219-28] as described previously [Winkler et al: Intranigral transplants of GABA-rich striatal tissue induce behavioral recovery in the rat Parkinson model and promote the effects obtained by intrastriatal dopaminergic transplants; Exp Neurol 1999 155 165-86]. Sugar pellets (TestDiet, Richmond, Va.) are placed on steps of a double staircase divided by a wide central platform (35 mm), all enclosed in a small Plexiglas box (285×60×90 mm). The animals were food deprived 48 hours before the first testing day and kept on a restricted food intake (6-8 g/day) throughout the test period with food only administrated after the daily test session. The staircase test was performed as a single session 21 weeks post-rAAV injections. The animals were trained in the staircase test for 21 consecutive days (15 min/day) with 10 sugar pellets placed on each of step 2-5 on both sides (total 40 pellets/side) where day 1 was defined as the first day the rats started retrieving sugar pellets. The data from day 11-15 was used as a stable performance score. At day 16-18 and 19-21, sugar pellets were only placed on the left and right shelf, respectively, challenging the rats with a forced choice. Skilled forelimb performance is expressed as the number of pellets eaten (taken−dropped) on the parkinsonian (left) side. The error rate was defined as percentage dropped ((taken−eaten/taken)×100).

Corridor test was performed at 5 weeks post 6-OHDA MFB lesion, pre AAV injection (defined lesion baseline) week 12 or week 25 post-AAV injections, as previously described [Dowd et al: The Corridor Task: a simple test of lateralised response selection sensitive to unilateral dopamine deafferentation and graft-derived dopamine replacement in the striatum; Brain Res Bull 2005 68 24-30] to study lateralized sensorimotor response selection. Briefly, the rats were placed in the end of a corridor (150 cm×7 cm×23 cm) with 10 adjacent pairs of lids, evenly distributed along the floor. Each lid was filled with 5-10 sugar pellets. Retrieval was defined as each time the rat poked its nose into a unique cup, regardless of if it ate any pellets. Revisits without interleaving other retrievals were not scored. Each rat was tested until 20 retrievals were made or a maximum time of 5 minutes elapsed. The rats were food restricted prior and throughout testing, as described above in the staircase test, and habituated for 10 minutes for 2 days in the corridor, with sugar pellets scattered along the floor. To reduce exploratory behaviour the rats were placed in an empty corridor before scoring. The rats were then scored for 4 days and the results are presented as an average of the last 2 days. Data is expressed as the number of contralateral retrievals as a percentage of total retrievals made.

Biochemical Analyses

Twelve rats were killed by decapitation, whereafter the brain was removed and sliced in the coronal axis into two parts using a brain mould. The striatal tissue from each hemisphere of the anterior part was then rapidly dissected and frozen individually on dry ice and stored at −80° C. until further analysis. The caudal part containing the midbrain-hindbrain regions was post-fixed in 4% paraformaldehyde (PFA) for 24 hours at 4° C. and then kept in 25% sucrose for at least 24 hours. The dissected brain tissue was homogenized and prepared using a modified version of a previously described protocol, which enables detection of monoamines and BH4 by high performance liquid chromatography (HPLC), in vitro TH activity and western blot analysis from the same sample [Romero-Ramos et al: Low selenium diet induces tyrosine hydroxylase enzyme in nigrostriatal system of the rat; Brain Res Mol Brain Res 2000 84 7-16]. Briefly, the tissue was homogenized on ice in Tris-acetate buffer (5 μl/mg, 20 mM, pH 6.1) using an ultrasonic disintegrator. One hundred μl of the homogenate was then pipetted into equal amount of ice-cold 0.8 mM perchloric acid for HPLC measurements. Remaining homogenate was centrifuged for 10 min at 17,000×g at 4° C. Forty μl of the supernatant was further diluted in 10 μl of Tris-acetate buffer (20 mM, pH 6.1) containing 0.6% Triton X-100 and stored at −20° C. for in vitro TH activity assay.

Microdialysis

Figure 8:
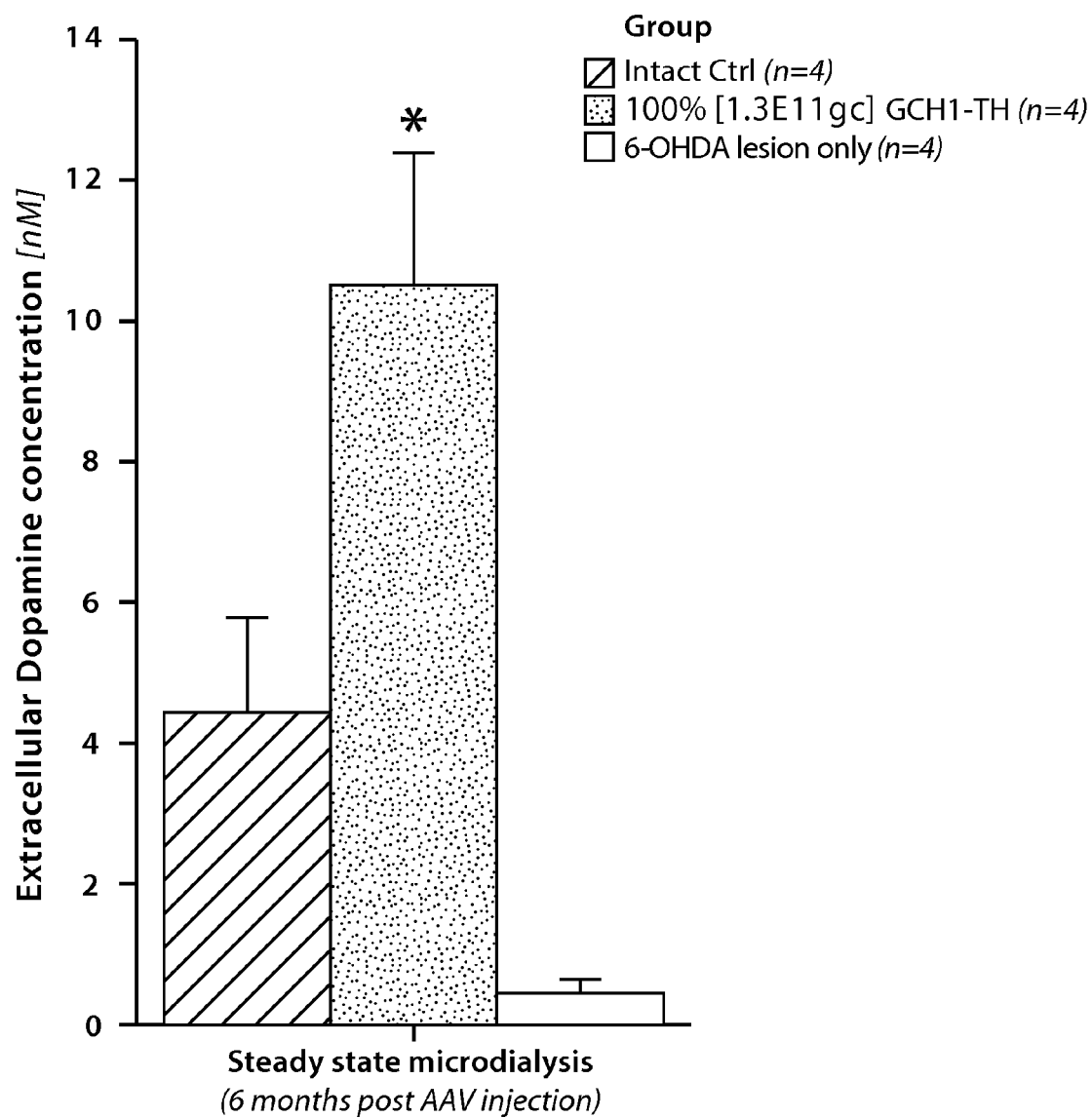
FIG. 8: Microdialysis quantification of extracellular dopamine levels. Animals with a complete, unilateral DA denervation were divided into two groups (TH-GCH1 group and 6-OHDA lesion only). Animals in the TH-GCH1 group then received a stereotactic injection of full titer rAAV5-TH: GCH1 vector. Unlesioned, intact age matched animals were also included in the study (Intact Ctrl). At least 6 months later, extracellular dopamine levels were quantified using on-line microdialysis. Extracellular dopamine levels were reduced by close to 90% in the Lesion control group. After rAAV5-TH:GCH1 injection on the other hand, the extracellular dopamine levels were restored to more than double those of intact animals. *=significantly different from Lesion controlin a one-way ANOVA followed by Tukey's HSD post-hoc test.

The microdialysis experiment (FIG. 8) was performed under isoflurane anaesthesia. A microdialysis probe with a 3 mm long semi-permeable membrane (35 kD cut-off PES membrane, Microbiotech AB) was inserted into the right (lesioned and transdiced) striatum at the coordinates AP: +0.5 mm; ML: −2.9 mm and DV: −4.25, −3.5 mm and (2) AP: 0 mm; ML: −3.2 mm and DV: −5.5 with the tooth bar set at −2.4 mm. The probe was flushed using aCSF at a flow rate of 0.67 μl/min loading the injection loops of a directly connected HPLC-EC equipment enabling analysis with a time resolution of 15 min. DA and metabolites were detected and quantified as described previously (Ulusoy et al. Presynaptic dopaminergic compartment determines the susceptibility to L-DOPA-induced dyskinesia in rats. Proc Natl Acad Sci USA (2010) vol. 107 (29) pp. 13159-64). The data is presented as an average of three consecutive measurements collected after a minimum of one hour of equilibration after probe implantation.

HPLC Analysis of Monoamines and BH4

The tissue homogenate in perchloric acid was incubated on ice for at least 20 min before centrifugation (15 min at 9,000×g at 4° C.). The supernatant was filtered through Whatman filter plate filters for additional 2 min at 9,000×g. Thereafter the sample was diluted 1:4 in Mili-Q filtered de-ionized water and stored in −80° C. until analysis. The tissue extracts were then analyzed HPLC-EC in three separate measurements for (1) DA and serotonin (5-HT); (2) DOPA; and (3) BH4. For each measurement, 25 µl of each sample was injected by a cooled autosampler (Spark Holland Midas) into an electrochemical detector (ESA Coulochem III) coupled to a guard cell (ESA 5020) and a glass-carbon electrode analytical cell (ESA 5011). For DA/5-HT and DOPA detection a reverse phase C18 column (3 µm ReproSil-pur, 4.6 mm Ø, 150 mm length, Chrompack) was used for compound separation, whereas for BH4 detection, this was replaced with another reverse phase C18 column (5 µm ReproSil-pur, 4.6 mm Ø, 250 mm length, Chrompack) preceded by a C8 column (5 µm ReproSil 80, 4.6 mm Ø, 33 mm length, Chrompack).

The mobile phase for DA/5-HT detection contained 60 mM sodium acetate, 90 µM $Na_2$-EDTA, 460 µM 1-octane-sulfonic acid in 9% methanol, where pH was adjusted to 4.2. For DOPA detection it contained 100 mM $NaH_2PO_4$ adjusted to pH 3.0 with $H_3PO_4$, 90 µM $Na_2$-EDTA, 1 mM sodium octyl sulphate in 10% methanol. The mobile phase used for BH4 detection, on the other hand, was modified from a previously described EC BH4 detection protocol [Howells and Hyland: Direct analysis of tetrahydrobiopterin in cerebrospinal fluid by high-performance liquid chromatography with redox electrochemistry: prevention of autoxidation during storage and analysis; Clin Chim Acta 1987 167 23-30] and composed of 50 mM sodium acetate, 5 mM citric acid, 48 µM EDTA, 160 µM DTE in 5% methanol, pH 5.2. The mobile phases were delivered at a flow rate of 500 µl/min for catecholamines and 1 ml/min for BH4. Peak identification and quantification was conducted using the Clarity Chromatographic software package (DataApex, Prague, Czech Republic).

Histological Analysis

Eight of the animals were deeply anesthetized by sodium pentobarbital overdose (Apoteksbolaget, Sweden) and transcardially perfused with 50 ml physiological saline solution followed by 250 ml of freshly prepared, ice-cold, 4% PFA in 0.1 M phosphate buffer adjusted to pH=7.4. The brains were removed and post-fixed for 2 hours in the same solution before cryoprotection in 25% sucrose for 24-48 hours before sectioning. The fixed brains and the post-fixed midbrain regions were cut into 40 µm coronal sections on a semi-automated freezing microtome (Microm HM 450) and collected into 6 series and stored in anti-freeze solution (0.5M sodium phosphate buffer, 30% glycerol and 30% ethylene glycol) at −20° C. until further processing. Immunohistochemistry was performed using antibodies raised against TH (rabbit IgG 1:10,000 Pel-Freez, Rogers, Ark.), and GCH1 (custom made rabbit IgG, 1:5,000). The staining was visualized using biotinylated secondary antibodies (goat anti-rabbit BA1000, Vector Laboratories, Burlingame, Calif.) followed by a 1-hour incubation with avidin-biotin peroxidase solution (ABC Elite, Vector Laboratories) developed by 3,3'-diaminobenzidine in 0.01% $H_2O_2$ colour reaction.

Example 2

Dosage Calculations

Findings in the rodent studies utilizing the single vector AAV mediated DOPA delivery in the rat model of complete dopamine denervation has enabled us to precisely determine the dose range required for functional recovery. Through careful evaluation, we have found that a dose of 9.1E8 gc GCH1-TH (defined as 0.7%, Table 1A) resulted in a significant recovery in 2 out of 10 animals in the corridor test. The next dose 4.6E9 gc GCH1-TH (3.4%) resulted in recovery in 8 out of 10 animals while the two highest doses tested, 1.3E10 gc GCH1-TH (9.8%) and 1.3E11 gc GCH1-TH (100%) enabled total recovery in 10 out of 10 animals in this test. The 100% dose however resulted in a more rapid recovery, complete already at three weeks post surgery.

For calculations on dosing equivalents in non-human primates and humans, a scaling factor for the putaminal region was calculated based on literature data on MR and histological evaluation (Table 1B). These data provide a scaling factor between rodents and humans of 1:60. These figure enabled the calculation of equivalent total dose between species (Table 1C) and also confirmation that such doses are realistic based on the currently achievable viral production titers. Based on an assumed production titer of 3E13 gc/ml, the injected dose per human putamen would fall between 1.82 µl and 260 µl (Table 1D).

For definitions that are adjusted to the individual patients differences in putaminal volume and bodyweight, the dose was re-defined as $gc/cm^3$ putaminal grey matter or kg body weight (Table 1E). In addition equivalents for µg single stranded DNA (ssDNA) of the vector preparation was generated based on the molecular weight of the vector genome (1.4 g/µmol).

Table 1, Definition of Therapeutic Dose Range

TABLE 1A

Dose definition

| Dose | Vector batch titers [gc/ml] |
| --- | --- |
| 0.7% | 1.8E+11 |
| 3.4% | 9.2E+11 |
| 9.8% | 2.6E+12 |
| 100% | 2.6E+13 |

TABLE 1B

Scaling factor of putaminal volume between species

| Species | Putamen volume [$cm^3$] | Scaling factor |
| --- | --- | --- |
| Rat | 0.06 (1) | 1 |
| Cynomolgus Macaque | 0.54 (2) | 9 |
| Rhesus Macaque | 0.81 (2) | 13.5 |
| Human | 3.6 (2) | 60 |

TABLE 1C

Total dose calculation

| Species | Total dose [gc@0.7%] | Total dose [gc@3.4%] | Total dose [gc@9.8%] | Total dose [gc@100%] |
| --- | --- | --- | --- | --- |
| Rat | 9.1E+08 | 4.6E+09 | 1.3E+10 | 1.3E+11 |
| Cynomolgus Macaque | 8.2E+09 | 4.1E+10 | 1.2E+11 | 1.2E+12 |

TABLE 1C-continued

Total dose calculation

| Species | Total dose [gc@0.7%] | Total dose [gc@3.4%] | Total dose [gc@9.8%] | Total dose [gc@100%] |
|---|---|---|---|---|
| Rhesus Macaque | 1.2E+10 | 6.2E+10 | 1.8E+11 | 1.8E+12 |
| Human | 5.5E+10 | 2.8E+11 | 7.8E+11 | 7.8E+12 |

TABLE 1D

Calculation of required volume

| | Req. Vol* [µl@0.7%] | Req. Vol* [µl@3.4%] | Req. Vol* [µl@9.8%] | Req. Vol* [µl@100%] |
|---|---|---|---|---|
| Rat | 0.03 | 0.15 | 0.43 | 4.3 |
| Cynomolgus Macaque | 0.273 | 1.38 | 3.9 | 39 |
| Rhesus Macaque | 0.41 | 2.1 | 5.85 | 58.5 |
| Human | 1.82 | 9.2 | 26 | 260 |

*Calculated from an assumed production titer of 3E13 gc/ml

TABLE 1E

Calculation of specific dose calculations for human therapy

| Dose level | Dose [gc/cm³ grey substance] | Dose [gc/kg body weight] | Dose [µg ssDNA/cm³ grey substance] | Dose [µg ssDNA/kg body weight] |
|---|---|---|---|---|
| 0.7% | 1.5E+10 | 1.5E+09 | 0.04 | 0.004 |
| 3.4% | 7.7E+10 | 7.5E+09 | 0.2 | 0.02 |
| 9.8% | 2.2E+11 | 2.1E+10 | 0.5 | 0.05 |
| 100% | 2.2E+12 | 2.1E+11 | 5.2 | 0.50 |

Patient average weight 74 kg calculated from refs (3, 4, 5)
Viral vector genome molecular weight calculated to 1.4 g/µmol The following references have been relied upon when determining the dose of the present invention.

(1) Chakos et al. Striatal enlargement in rats chronically treated with neuroleptic. Biol Psychiatry (1998) vol. 44 (8) pp. 675-84
(2) Yin et al. Striatal volume differences between non-human and human primates. Neurosci Methods (2009) vol. 176 (2) pp. 200-5
(3) Beyer et al. Weight change and body composition in patients with Parkinson's disease. J Am Diet Assoc (1995) vol. 95 (9) pp. 979-83
(4) Uc et al. Predictors of weight loss in Parkinson's disease. MovDisord (2006) vol. 21 (7) pp. 930-6
(5) Delikanaki-Skaribas et al. Daily energy expenditure, physical activity, and weight loss in Parkinson's disease patients. MovDisord (2009) vol. 24 (5) pp. 667-71

All experimental procedures performed and presented herein have been approved by the Ethical Committee for Use of Laboratory Animals in the Lund-Malmö region. Ethical permit numbers: M59-06 and M267-08.

Example 3

Sequences Included in the Invention

SEQ ID NO 1: GTP cyclohydrolase 1 (human)
SEQ ID NO 2: GTP cyclohydrolase 1 Isoform GCH-2 (human)
SEQ ID NO 3: GTP cyclohydrolase 1 Isoform GCH-3 (human)
SEQ ID NO 4: GTP cyclohydrolase 1 Isoform GCH-4 (human)
SEQ ID NO 5: GTP cyclohydrolase 1 (rat)
SEQ ID NO 6: GTP cyclohydrolase 1 (mouse)
SEQ ID NO 7: Tyrosine 3-hydroxylase (human)
SEQ ID NO 8: Tyrosine 3-monooxygenase (human)
SEQ ID NO 9: Tyrosine hydroxylase (human)
SEQ ID NO 10: Tyrosine hydroxylase (human)
SEQ ID NO 11: Tyrosine 3-monooxygenase (human)
SEQ ID NO 12: Tyrosine 3-monooxygenase (human)
SEQ ID NO 13: Tyrosine 3-hydroxylase (rat)
SEQ ID NO 14: Tyrosine 3-hydroxylase (mouse)
SEQ ID NO 15: Adeno-associated virus 2 left terminal sequence
SEQ ID NO 16: Adeno-associated virus 2 right terminal sequence
SEQ ID NO 17: *Homo sapiens* synapsin 1 (SYN1) promoter sequence
SEQ ID NO 18: *Homo sapiens* GTP cyclohydrolase 1 (GCH1), transcript variant 1
SEQ ID NO 19: Simian virus 40 early poly-adenylation sequence
SEQ ID NO 20: Simian virus 40 late poly-adenylation sequence
SEQ ID NO 21: *Homo sapiens* tyrosine hydroxylase (TH), transcript variant 2
SEQ ID NO 22: Woodchuck hepatitis B virus (WHV8) post-transcriptional regulatory element sequence

```
SEQ ID NO 1: GTP cyclohydrolase 1 (human)
>sp|P30793|GCH1_HUMAN GTP cyclohydrolase 1 OS = Homo sapiens GN = GCH1
PE = 1 SV = 1 EC = 3.5.4.16
Alternative name(s):
GTP cyclohydrolase I
Short names = GTP-CH-I or GCH-1 or GCH1 or GCH 1
Organism: Homo sapiens (Human)
http://www.uniprot.org/uniprot/P30793
MEKGPVRAPAEKPRGARCSNGFPERDPPRPGPSRPAEKPPRPEAKSAQPADGWKGERPRS
EEDNELNLPNLAAAYSSILSSLGENPQRQGLLKTPWRAASAMQFFTKGYQETISDVLNDA
IFDEDHDEMVIVKDIDMFSMCEHHLVPFVGKVHIGYLPNKQVLGLSKLARIVEIYSRRLQ
VQERLTKQIAVAITEALRPAGVGVVVEATHMCMVMRGVQKMNSKTVTSTMLGVFREDPKT
REEFLTLIRS
```

SEQ ID NO 2: GTP cyclohydrolase 1 Isoform GCH-2 (human)
>sp|P30793-2|GCH1_HUMAN Isoform GCH-2 of GTP cyclohydrolase 1 OS =
Homo sapiens GN = GCH1
MEKGPVRAPAEKPRGARCSNGFPERDPPRPGPSRPAEKPPRPEAKSAQPADGWKGERPRSEEDNELNL
PNLAAAYSSILSSLGENPQRQGLLKTPWRAASAMQFFTKGYQETISDVLNDAIFDEDHDEMVIVKDIDMFS
MCEHHLVPFVGKVHIGYLPNKQVLGLSKLARIVEIYSRRLQVQERLTKQIAVAITEALRPAGVGVVVEATSA
EP SEQ ID NO 3: GTP cyclohydrolase 1 Isoform GCH-3 (human)
>sp|P30793-3|GCH1_HUMAN Isoform GCH-3 of GTP cyclohydrolase 1 OS = Homo
sapiens GN = GCH1
MEKGPVRAPAEKPRGARCSNGFPERDPPRPGPSRPAEKPPRPEAKSAQPADGWKGERPRSEEDNELNL
PNLAAAYSSILSSLGENPQRQGLLKTPWRAASAMQFFTKGYQETISDVLNDAIFDEDHDEMVIVKDIDMFS
MCEHHLVPFVGKVHIGYLPNKQVLGLSKLARIVEIYSRRLQVQERLTKQIAVAITEALRPAGVGVVVEAT SEQ ID NO 4: GTP cyclohydrolase 1 Isoform GCH-4 (human)
>sp|P30793-4|GCH1_HUMAN Isoform GCH-4 of GTP cyclohydrolase 1 OS = Homo
sapiens GN = GCH1
MEKGPVRAPAEKPRGARCSNGFPERDPPRPGPSRPAEKPPRPEAKSAQPADGWKGERPRS
EEDNELNLPNLAAAYSSILSSLGENPQRQGLLKTPWRAASAMQFFTKGYQETISDVLNDA
IFDEDHDEMVIVKDIDMFSMCEHHLVPFVGKVHIGYLPNKQVLGLSKLARIVELYSRRLQ
VQERLTKQIAVAITEALRPAGVGVVVEATKSNKYNKGLSPLLSSCHLFVAILK SEQ ID NO 5: GTP cyclohydrolase 1 (rat)
>sp|P22288|GCH1_RAT GTP cyclohydrolase 1 OS = Rattus norvegicus GN = Gch1
PE = 1 SV = 1
MEKPRGVRCTNGFPERELPRPGASRPAEKSRPPEAKGAQPADAWKAGRPRSEEDNELNLP
NLAAAYSSILRSLGEDPQRQGLLKTPWRAATAMQFFTKGYQETISDVLNDAIFDEDHDEM
VIVKDIDMFSMCEHHLVPFVGRVHIGYLPNKQVLGLSKLARIVEIYSRRLQVQERLTKQI
AVAITEALQPAGVGVVIEATHMCMVMRGVQKMNSKTVTSTMLGVFREDPKTREEFLTLIR
S SEQ ID NO 6: GTP cyclohydrolase 1 (mouse)
>sp|Q05915|GCH1_MOUSE GTP cyclohydrolase 1 OS = Mus musculus GN = Gch1
PE = 2 SV = 1
MEKPRGVRCTNGFSERELPRPGASPPAEKSRPPEAKGAQPADAWKAGRHRSEEENQVNLP
KLAAAYSSILLSLGEDPQRQGLLKTPWRAATAMQYFTKGYQETISDVLNDAIFDEDHDEM
VIVKDIDMFSMCEHHLVPFVGRVHIGYLPNKQVLGLSKLARIVEIYSRRLQVQERLTKQI
AVAITEALQPAGVGVVIEATHMCMVMRGVQKMNSKTVTSTMLGVFREDPKTREEFLTLIR
S SEQ ID NO 7: Tyrosine 3-hydroxylase (human)
EC = 1.14.16.2
Alternative name(s): Tyrosine 3-monooxygenase or Tyrosine 3-hydroxylase or
Tyrosine hydroxylase Short name = TH
Organism: Homo sapiens (Human)
MPTPDATTPQAKGFRRAVSELDAKQAEAIMSPRFIGRRQSLIEDARKEREAAVAAAAAVPSEPGDPLEAV
AFEEKEGKAVLNLLFSPRATKPSALSRAVKVFETFEAKIHHLETRPAQRPRAGGPHLEYFVRLEVRRGDLA
ALLSGVRQVSEDVRSPAGPKVPWFPRKVSELDKCHHLVTKFDPDLDLDHPGFSDQVYRQRRKLIAEIAFQ
YRHGDPIPRVEYTAEEIATWKEVYTTLKGLYATHACGEHLEAFALLERFSGYREDNIPQLEDVSRFLKERT
GFQLRPVAGLLSARDFLASLAFRVFQCTQYIRHASSPMHSPEPDCCHELLGHVPMLADRTFAQFSQDIGL
ASLGASDEEIEKLSTLYWFTVEFGLCKQNGEVKAYGAGLLSSYGELLHCLSEEPEIRAFDPEAAAVQPYQD
QTYQSVYFVSESFSDAKDKLRSYASRIQRPFSVKFDPYTLAIDVLDSPQAVRRSLEGVQDELDTLAHALSAI SEQ ID NO 8: Tyrosine 3-monooxygenase (human)
>sp|P07101|TY3H_HUMAN Tyrosine 3-monooxygenase OS = Homo sapiens GN = TH
PE = 1 SV = 5
MPTPDATTPQAKGFRRAVSELDAKQAEAIMVRGQGAPGPSLTGSPWPGTAAPAASYTPTP
RSPRFIGRRQSLIEDARKEREAAVAAAAAVPSEPGDPLEAVAFEEKEGKAVLNLLFSPR
ATKPSALSRAVKVFETFEAKIHHLETRPAQRPRAGGPHLEYFVRLEVRRGDLAALLSGVR
QVSEDVRSPAGPKVPWFPRKVSELDKCHHLVTKFDPDLDLDHPGFSDQVYRQRRKLIAEI
AFQYRHGDPIPRVEYTAEEIATWKEVYTTLKGLYATHACGEHLEAFALLERFSGYREDNI
PQLEDVSRFLKERTGFQLRPVAGLLSARDFLASLAFRVFQCTQYIRHASSPMHSPEPDCC
HELLGHVPMLADRTFAQFSQDIGLASLGASDEEIEKLSTLYWFTVEFGLCKQNGEVKAYG
AGLLSSYGELLHCLSEEPEIRAFDPEAAAVQPYQDQTYQSVYFVSESFSDAKDKLRSYAS
RIQRPFSVKFDPYTLAIDVLDSPQAVRRSLEGVQDELDTLAHALSAIG SEQ ID NO 9: Tyrosine hydroxylase (human)
>tr|Q2M3B4|Q2M3B4_HUMAN Tyrosine hydroxylase OS = Homo sapiens GN = TH
PE = 2 SV = 1
MPTPDATTPQAKGFRRAVSELDAKQAEAIMSPRFIGRRQSLIEDARKEREAAVAAAAAV
PSEPGDPLEAVAFEEKEGKAMLNLLFSPRATKPSALSRAVKVFETFEAKIHHLETRPAQR
PRAGGPHLEYFVRLEVRRGDLAALLSGVRQVSEDVRSPAGPKVPWFPRKVSELDKCHHLV
TKFDPDLDLDHPGFSDQVYRQRRKLIAEIAFQYRHGDPIPRVEYTAEEIATWKEVYTTLK
GLYATHACGEHLEAFALLERFSGYREDNIPQLEDVSRFLKERTGFQLRPVAGLLSARDFL
ASLAFRVFQCTQYIRHASSPMHSPEPDCCHELLGHVPMLADRTFAQFSQDIGLASLGASD
EEIEKLSTLYWFTVEFGLCKQNGEVKAYGAGLLSSYGELLHCLSEEPEIRAFDPEAAAVQ
PYQDQTYQSVYFVSESFSDAKDKLRSYASRIQRPFSVKFDPYTLAIDVLDSPQAVRRSLE
GVQDELDTLAHALSAIG

```
SEQ ID NO 10: Tyrosine hydroxylase (human)
>tr|B7ZL73|B7ZL73_HUMAN TH protein OS = Homo sapiens GN = TH PE = 1 SV = 1
MPTPDATTPQAKGFRRAVSELDAKQAEAIMVRGQSPRFIGRRQSLIEDARKEREAAVAAA
AAAVPSEPGDPLEAVAFEEKEGKAMLNLLFSPRATKPSALSRAVKVFETFEAKIHHLETR
PAQRPRAGGPHLEYFVRLEVRRGDLAALLSGVRQVSEDVRSPAGPKVPWFPRKVSELDKC
HHLVTKFDPDLDLDHPGFSDQVYRQRRKLIAEIAFQYRHGDPIPRVEYTAEEIATWKEVY
TTLKGLYATHACGEHLEAFALLERFSGYREDNIPQLEDVSRFLKERTGFQLRPVAGLLSA
RDFLASLAFRVFQCTQYIRHASSPMHSPEPDCCHELLGHVPMLADHTFAQFSQDIGLASL
GASDEEIEKLSTLYWFTVEFGLCKQNGEVKAYGAGLLSSYGELLHCLSEEPEIRAFDPEA
AAVQPYQDQTYQSVYFVSESFSDAKDKLRSYASRIQRPFSVKFDPYTLAIDVLDSPQAVR
RSLEGVQDELDTLAHALSAIG SEQ ID NO 11: Tyrosine 3-monooxygenase (human)
>sp|P07101|TY3H_HUMAN Tyrosine 3-monooxygenase OS = Homo sapiens GN = TH
PE = 1 SV = 5
MPTPDATTPQAKGFRRAVSELDAKQAEAIMVRGQGAPGPSLTGSPWPGTAAPAASYTPTP
RSPRFIGRRQSLIEDARKEREAAVAAAAAAVPSEPGDPLEAVAFEEKEGKAVLNLLFSPR
ATKPSALSRAVKVFETFEAKIHHLETRPAQRPRAGGPHLEYFVRLEVRRGDLAALLSGVR
QVSEDVRSPAGPKVPWFPRKVSELDKCHHLVTKFDPDLDLDHPGFSDQVYRQRRKLIAEI
AFQYRHGDPIPRVEYTAEEIATWKEVYTTLKGLYATHACGEHLEAFALLERFSGYREDNI
PQLEDVSRFLKERTGFQLRPVAGLLSARDFLASLAFRVFQCTQYIRHASSPMHSPEPDCC
HELLGHVPMLADRTFAQFSQDIGLASLGASDEEIEKLSTLYWFTVEFGLCKQNGEVKAYG
AGLLSSYGELLHCLSEEPEIRAFDPEAAAVQPYQDQTYQSVYFVSESFSDAKDKLRSYAS
RIQRPFSVKFDPYTLAIDVLDSPQAVRRSLEGVQDELDTLAHALSAIG SEQ ID NO 12: Tyrosine 3-monooxygenase (human)
>sp|P07101|TY3H_HUMAN Tyrosine 3-monooxygenase OS = Homo sapiens GN = TH
PE = 1 SV = 5
MPTPDATTPQAKGFRRAVSELDAKQAEAIMVRGQGAPGPSLTGSPWPGTAAPAASYTPTP
RSPRFIGRRQSLIEDARKEREAAVAAAAAAVPSEPGDPLEAVAFEEKEGKAVLNLLFSPR
ATKPSALSRAVKVFETFEAKIHHLETRPAQRPRAGGPHLEYFVRLEVRRGDLAALLSGVR
QVSEDVRSPAGPKVPWFPRKVSELDKCHHLVTKFDPDLDLDHPGFSDQVYRQRRKLIAEI
AFQYRHGDPIPRVEYTAEEIATWKEVYTTLKGLYATHACGEHLEAFALLERFSGYREDNI
PQLEDVSRFLKERTGFQLRPVAGLLSARDFLASLAFRVFQCTQYIRHASSPMHSPEPDCC
HELLGHVPMLADRTFAQFSQDIGLASLGASDEEIEKLSTLYWFTVEFGLCKQNGEVKAYG
AGLLSSYGELLHCLSEEPEIRAFDPEAAAVQPYQDQTYQSVYFVSESFSDAKDKLRSYAS
RIQRPFSVKFDPYTLAIDVLDSPQAVRRSLEGVQDELDTLAHALSAIG SEQ ID NO 13: Tyrosine 3-hydroxylase (rat)
>sp|P04177|TY3H_RAT Tyrosine 3-monooxygenase OS = Rattus norvegicus GN = Th
PE = 1 SV = 3
MPTPSAPSPQPKGFRRAVSEQDAKQAEAVTSPRFIGRRQSLIEDARKEREAAAAAAAAAV
ASSEPGNPLEAVVFEERDGNAVLNLLFSLRGTKPSSLSRVRRVSDDVRSAREDKVPWFPR
RPLAGSPHLEYFVRFEVPSGDLAALLSSVRRVSDDVRSAREDKVPWFPRKVSELDKCHHL
VTKFDPDLDLDHPGFSDQVYRQRRKLIAEIAFQYKHGEPIPHVEYTAEEIATWKEVYVTL
KGLYATHACREHLEGFQLLERYCGYREDSIPQLEDVSRFLKERTGFQLRPVAGLLSARDF
LASLAFRVFQCTQYIRHASSPMHSPEPDCCHELLGHVPMLADRTFAQFSQDIGLASLGAS
DEEIEKLSTVYWFTVEFGLCKQNGELKAYGAGLLSSYGELLHLSEEPEVRAFDPDTAAV
QPYQDQTYQPVYFVSESFNDAKDKLRNYASRIQRPFSVKFDPYTLAIDVLDSPHTIQRSL
EGVQDELHTLAHALSAIS SEQ ID NO 14: Tyrosine 3-hydroxylase (mouse)
>sp|P24529|TY3H_MOUSE Tyrosine 3-monooxygenase OS = Mus musculus GN = Th
PE = 1 SV = 3
MPTPSASSPQPKGFRRAVSEQDTKQAEAVTSPRFIGRRQSLIEDARKEREAAAAAAAAAV
ASAEPGNPLEAVVFEERDGNAVLNLLFSLRGTKPSSLSRALKVFETFEAKIHHLETRPAQ
RPLAGSPHLEYFVRFEVPSGDLAALLSSVRRVSDDVRSAREDKVPWFPRKVSELDKCHHL
VTKFDPDLDLDHPGFSDQAYRQRRKLIAEIAFQYKQGEPIPHVEYTKEEIATWKEVYATL
KGLYATHACREHLEAFQLLERYCGYREDSIPQLEDVSHFLKERTGFQLRPVAGLLSARDF
LASLAFRVFQCTQYIRHASSPMHSPEPDCCHELLGHVPMLADRTFAQFSQDIGLASLGAS
DEEIEKLSTVYWFTVEFGLCKQNGELKAYGAGLLSSYGELLHLSEEPEVRAFDPDTAAV
QPYQDQTYQPVYFVSESFSDAKDKLRNYASRIQRPFSVKFDPYTLAIDVLDSPHTIRRSL
EGVQDELHTLTQALSAIS SEQ ID NO 15: Adeno-associated virus 2 left terminal sequence
ttggccactccctctctgcgcgctcgctcgctcactgaggccgggcgaccaaaggtcgcccgacgcccgggct
ttgcccgggcggcctcagtgagcgagcgagcgcgcagagagggagtggccaactccatcactagggggttcct SEQ ID NO 16: Adeno-associated virus 2 right terminal sequence
aggaaccccctagtgatggagttggccactccctctctgcgcgctcgctcgctcactgaggccgcccgggcaaa
gcccgggcgtcgggcgacctttggtcgcccggcctcagtgagcgagcgagcgcgcagagagggagtggccaa SEQ ID NO 17: Homo sapiens synapsin 1 (SYN1) promoter sequence
CTAGACTCTAGCTGCAGAGGGACCTGCGTATGAGTGCAAGTGGGTTTTAGGACCAGGATGAGGCGG
GGTGGGGGTGCCTACCTGACGACCGACCCCGACCCACTGGACAAGCACCCAACCCCCATTCCCCAA
ATTGCGCATCCCCTATCAGAGAGGGGGAGGGGAAACAGGATGCGGCGAGGCGCGTGCGCACTGCC
AGCTTCAGCACCGCGGACAGTGCCTTCGCCCCCGCCTGGCGGCGCGCGCCACCGCCGCCTCAGCA
CTGAAGGCGCGCTGACGTCACTCGCCGGTCCCCCGCAAACTCCCCTTCCCGGCCACCTTGGTCGCG
TCCGCGCCGCCGCCGGCCCAGCCGGACCGCACCACGCGAGGCGCGAGATAGGGGGGCACGGGCG
CGACCATCTGCGCTGCGGCGCCGGCGACTCAGCGCTGCCTCAGTCTGCGGTGGGCAGCGGAGGAG
TCGTGTCGTGCCTGAGAGCGCAGTCGA
```

SEQ ID NO 18: Homo sapiens GTP cyclohydrolase 1 (GCH1), transcript variant 1
ATGGAGAAGGGCCCTGTGCGGGCACCGGCGGAGAAGCCGCGGGGCGCCAGGTGCAGCAATGGGTT
CCCCGAGCGGGATCCGCCGCGGCCCGGGCCCAGCAGGCCGGCGGAGAAGCCCCCGCGGCCCGAG
GCCAAGAGCGCGCAGCCCGCGGACGGCTGGAAGGGCGAGCGGCCCCGCAGCGAGGAGGATAACG
AGCTGAACCTCCCTAACCTGGCAGCCGCCTACTCGTCCATCCTGAGCTCGCTGGGCGAGAACCCCC
AGCGGCAAGGGCTGCTCAAGACGCCCTGGAGGGCGGCCTCGGCCATGCAGTTCTTCACCAAGGGCT
ACCAGGAGACCATCTCAGATGTCCTAAACGATGCTATATTTGATGAAGATCATGATGAGATGGTGATT
GTGAAGGACATAGACATGTTTTCCATGTGTGAGCATCACTTGGTTCCATTTGTTGGAAAGGTCCATATT
GGTTATCTTCCTAACAAGCAAGTCCTTGGCCTCAGCAAACTTGCGAGGATTGTAGAAATCTATAGTAG
AAGACTACAAGTTCAGGAGCGCCTTACAAAACAAATTGCTGTAGCAATCACGGAAGCCTTGCGGCCT
GCTGGAGTCGGGGTAGTGGTTGAAGCAACACACATGTGTATGGTAATGCGAGGTGTACAGAAAATGA
ACAGCAAACTGTGACCAGCACAATGTTGGGTGTGTTCCGGGAGGATCCAAAGACTCGGGAAGAGTT
CCTGACTCTCATTAGGA SEQ ID NO 19: Simian virus 40 early poly-adenylation sequence
TTCGAGCAACTTGTTTATTGCAGCTTATAATGGTTACAAATAAAGCAATAGCATCACAAATTTCACAAAT
AAAGCATTTTTTTCACTGCATTCTAGTTGTGGTTTGTCCAAACTCATCAATGTATCTTATCATGTCTGGA
TCGTCTAGCATCGAA SEQ ID NO 20: Simian virus 40 late poly-adenylation sequence
CAGACATGATAAGATACATTGATGAGTTTGGACAAACCACAACTAGAATGCAGTGAAAAAAATGCTTTA
TTTGTGAAATTTGTGATGCTATTGCTTTATTTGTAACCATTATAAGCTGCAATAAACAAGTTAACAACAA
CAATTGCATTCATTTTATGTTTCAGGTTCAGGGGGAGGTGTGGGAGGTTTTTT SEQ ID NO 21: Homo sapiens tyrosine hydroxylase (TH), transcript variant 2
ATGCCCACCCCCGACGCCACCACGCCACAGGCCAAGGGCTTCCGCAGGGCCGTGTCTGAGCTGGA
CGCCAAGCAGGCAGAGGCCATCATGTCCCCGCGGTTCATTGGGCGCAGGCAGAGCCTCATCGAGGA
CGCCCGCAAGGAGCGGGAGGCGGCGGTGGCAGCAGCGGCCGCTGCAGTCCCCTCGGAGCCCGGG
GACCCCCTGGAGGCTGTGGCCTTTGAGGAGAAGGAGGGGAAGGCCGTGCTAAACCTGCTCTTCTCC
CCGAGGGCCACCAAGCCCTCGGCGCTGTCCCGAGCTGTGAAGGTGTTTGAGACGTTTGAAGCCAAA
ATCCACCATCTAGAGACCCGGCCCGCCCAGAGGCCGCGAGCTGGGGCCCCCACCTGGAGTACTTC
GTGCGCCTCGAGGTGCGCCGAGGGGACCTGGCCGCCCTGCTCAGTGGTGTGCGCCAGGTGTCAGA
GGACGTGCGCAGCCCCGCGGGGCCCAAGGTCCCCTGGTTCCCAAGAAAAGTGTCAGAGCTGGACAA
GTGTCATCACCTGGTCACCAAGTTCGACCCTGACCTGGACTTGGACCACCCGGGCTTCTCGGACCAG
GTGTACCGCCAGCGCAGGAAGCTGATTGCTGAGATCGCCTTCCAGTACAGGCACGGCGACCCGATT
CCCCGTGTGGAGTACACCGCCGAGGAGATTGCCACCTGGAAGGAGGTCTACACCACGCTGAAGGGC
CTCTACGCCACGCACGCCTGCGGGGAGCACCTGGAGGCCTTTGCTTTGCTGGAGCGCTTCAGCGGC
TACCGGGAAGACAATATCCCCCAGCTGGAGGACGTCTCCCGCTTCCTGAAGGAGCGCACGGGCTTC
CAGCTGCGGCCTGTGGCCGGCCTGCTGTCCGCCCGGGACTTCCTGGCCAGCCTGGCCTTCCGCGT
GTTCCAGTGCACCCAGTATATCCGCCACGCGTCCTCGCCCATGCACTCCCCTGAGCCGGACTGCTGC
CACGAGCTGCTGGGGCACGTGCCCATGCTGGCCGACCGCACCTTCGCGCAGTTCTCGCAGGACATT
GGCTTGGCGTCCCTGGGGGCCTCGGATGAGGAAATTGAGAAGCTGTCCACGCTGTACTGGTTCACG
GTGGAGTTCGGGCTGTGTAAGCAGAACGGGGAGGTGAAGGCCTATGGTGCCGGGCTGCTGTCCTCC
TACGGGGAGCTCCTGCACTGCCTGTCTGAGGAGCCTGAGATTCGGGCCTTCGACCCTGAGGCTGCG
GCCGTGCAGCCCTACCAAGACCAGACGTACCAGTCAGTCTACTTCGTGTCTGAGAGCTTCAGTGACG
CCAAGGACAAGCTCAGGAGCTATGCCTCACGCATCCAGCGCCCCTTCTCCGTGAAGTTCGACCCGTA
CACGCTGGCCATCGACGTGCTGGACAGCCCCCAGGCCGTGCGGCGCTCCCTGGAGGGTGTCCAGG
ATGAGCTGGACACCCTTGCCCATGCGCTGAGTGCCATTGG SEQ ID NO 22: Woodchuck hepatitis B virus (WHV8) post-transcriptional
regulatory element sequence
CGTCGACAATCAACCTCTGGATTACAAAATTTGTGAAAGATTGACTGGTATTCTTAACTATGTTGCTCC
TTTTACGCTATGTGGATACGCTGCTTTAATGCCTTTGTATCATGCTATTGCTTCCCGTATGCTTTCATT
TTCTCCTCCTTGTATAAATCCTGGTTGCTGTCTCTTTATGAGGAGTTGTGGCCCGTTGTCAGGCAACG
TGGCGTGGTGTGCACTGTGTTTGCTGACGCAACCCCCACTGGTTGGGGCATTGCCACCACCTGTCAG
CTCCTTTCCGGGACTTTCGCTTTCCCCCTCCCTATTGCCACGGCGGAACTCATCGCCGCCTGCCTTG
CCCGCTGCTGGACAGGGGCTCGGCTGTTGGGCACTGACAATTCCGTGGTGTTGTCGGGGAAGCTGA
CGTCCTTTCCATGGCTGCTCGCCTGTGTTGCCACCTGGATTCTGCGCGGGACGTCCTTCTGCTACGT
CCCTTCGGCCCTCAATCCAGCGGACCTTCCTTCCCGCGGCCTGCTGCCGGCTCTGCGGCCTCTTCC
GCGTCTTCGCCTTCGCCCTCAGACGAGTCGGATCTCCCTTTGGGCCGCCTCCCCGCCTGGAATTCGA
GCT

SEQUENCE LISTING

<160> NUMBER OF SEQ IDS NOS: 23

<210> SEQ ID NO 1
<211> LENGTH: 250
<212> TYPE: PRT
<213> ORGANISM: Homo sapiens
<220> FEATURE:
<221> NAME/KEY: MISC_FEATURE
<222> LOCATION: (1)..(250)
<223> OTHER INFORMATION: GTP cyclohydrolase 1

<400> SEQUENCE: 1

```
Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Pro Arg Pro Glu Ala Lys Ser Ala Gln
            35                  40                  45

Pro Ala Asp Gly Trp Lys Gly Glu Arg Pro Arg Ser Glu Glu Asp Asn
50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
            100                 105                 110

Ile Ser Asp Val Leu Asn Asp Ala Ile Phe Asp Glu Asp His Asp Glu
            115                 120                 125

Met Val Ile Val Lys Asp Ile Asp Met Phe Ser Met Cys Glu His His
130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
            180                 185                 190

Ile Thr Glu Ala Leu Arg Pro Ala Gly Val Gly Val Val Val Glu Ala
            195                 200                 205

Thr His Met Cys Met Val Met Arg Gly Val Gln Lys Met Asn Ser Lys
210                 215                 220

Thr Val Thr Ser Thr Met Leu Gly Val Phe Arg Glu Asp Pro Lys Thr
225                 230                 235                 240

Arg Glu Glu Phe Leu Thr Leu Ile Arg Ser
                245                 250

<210> SEQ ID NO 2
<211> LENGTH: 213
<212> TYPE: PRT
<213> ORGANISM: Homo sapiens
<220> FEATURE:
<221> NAME/KEY: MISC_FEATURE
<222> LOCATION: (1)..(213)
<223> OTHER INFORMATION: GTP cyclohydrolase 1 Isoform GCH-2

<400> SEQUENCE: 2

Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Pro Arg Pro Glu Ala Lys Ser Ala Gln
            35                  40                  45

Pro Ala Asp Gly Trp Lys Gly Glu Arg Pro Arg Ser Glu Glu Asp Asn
50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95
```

```
Arg Ala Ala Ser Ala Met Gln Phe Phe Thr Lys Gly Tyr Gln Glu Thr
                100                 105                 110

Ile Ser Asp Val Leu Asn Asp Ala Ile Phe Asp Glu Asp His Asp Glu
            115                 120                 125

Met Val Ile Val Lys Asp Ile Asp Met Phe Ser Met Cys Glu His His
130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
                180                 185                 190

Ile Thr Glu Ala Leu Arg Pro Ala Gly Val Gly Val Val Val Glu Ala
            195                 200                 205

Thr Ser Ala Glu Pro
            210

<210> SEQ ID NO 3
<211> LENGTH: 209
<212> TYPE: PRT
<213> ORGANISM: Homo sapiens
<220> FEATURE:
<221> NAME/KEY: MISC_FEATURE
<222> LOCATION: (1)..(209)
<223> OTHER INFORMATION: GTP cyclohydrolase 1 Isoform GCH-3

<400> SEQUENCE: 3

Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Pro Arg Pro Glu Ala Lys Ser Ala Gln
        35                  40                  45

Pro Ala Asp Gly Trp Lys Gly Glu Arg Pro Arg Ser Glu Glu Asp Asn
    50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
                100                 105                 110

Ile Ser Asp Val Leu Asn Asp Ala Ile Phe Asp Glu Asp His Asp Glu
            115                 120                 125

Met Val Ile Val Lys Asp Ile Asp Met Phe Ser Met Cys Glu His His
130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
                180                 185                 190

Ile Thr Glu Ala Leu Arg Pro Ala Gly Val Gly Val Val Val Glu Ala
            195                 200                 205

Thr

<210> SEQ ID NO 4
```

```
<211> LENGTH: 233
<212> TYPE: PRT
<213> ORGANISM: Homo sapiens
<220> FEATURE:
<221> NAME/KEY: MISC_FEATURE
<222> LOCATION: (1)..(233)
<223> OTHER INFORMATION: GTP cyclohydrolase 1 Isoform GCH-4

<400> SEQUENCE: 4

Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Pro Arg Pro Glu Ala Lys Ser Ala Gln
        35                  40                  45

Pro Ala Asp Gly Trp Lys Gly Glu Arg Pro Arg Ser Glu Glu Asp Asn
    50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
            100                 105                 110

Ile Ser Asp Val Leu Asn Asp Ala Ile Phe Asp Glu Asp His Asp Glu
        115                 120                 125

Met Val Ile Val Lys Asp Ile Asp Met Phe Ser Met Cys Glu His His
    130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
            180                 185                 190

Ile Thr Glu Ala Leu Arg Pro Ala Gly Val Gly Val Val Val Glu Ala
        195                 200                 205

Thr Lys Ser Asn Lys Tyr Asn Lys Gly Leu Ser Pro Leu Leu Ser Ser
    210                 215                 220

Cys His Leu Phe Val Ala Ile Leu Lys
225                 230

<210> SEQ ID NO 5
<211> LENGTH: 241
<212> TYPE: PRT
<213> ORGANISM: Rattus norvegicus
<220> FEATURE:
<221> NAME/KEY: MISC_FEATURE
<222> LOCATION: (1)..(241)
<223> OTHER INFORMATION: GTP cyclohydrolase 1

<400> SEQUENCE: 5

Met Glu Lys Pro Arg Gly Val Arg Cys Thr Asn Gly Phe Pro Glu Arg
1               5                   10                  15

Glu Leu Pro Arg Pro Gly Ala Ser Arg Pro Ala Glu Lys Ser Arg Pro
            20                  25                  30

Pro Glu Ala Lys Gly Ala Gln Pro Ala Asp Ala Trp Lys Ala Gly Arg
        35                  40                  45

Pro Arg Ser Glu Glu Asp Asn Glu Leu Asn Leu Pro Asn Leu Ala Ala
    50                  55                  60
```

```
Ala Tyr Ser Ser Ile Leu Arg Ser Leu Gly Glu Asp Pro Gln Arg Gln
 65                  70                  75                  80

Gly Leu Leu Lys Thr Pro Trp Arg Ala Ala Thr Ala Met Gln Phe Phe
                 85                  90                  95

Thr Lys Gly Tyr Gln Glu Thr Ile Ser Asp Val Leu Asn Asp Ala Ile
            100                 105                 110

Phe Asp Glu Asp His Asp Glu Met Val Ile Val Lys Asp Ile Asp Met
        115                 120                 125

Phe Ser Met Cys Glu His His Leu Val Pro Phe Val Gly Arg Val His
130                 135                 140

Ile Gly Tyr Leu Pro Asn Lys Gln Val Leu Gly Leu Ser Lys Leu Ala
145                 150                 155                 160

Arg Ile Val Glu Ile Tyr Ser Arg Arg Leu Gln Val Gln Glu Arg Leu
                165                 170                 175

Thr Lys Gln Ile Ala Val Ala Ile Thr Glu Ala Leu Gln Pro Ala Gly
            180                 185                 190

Val Gly Val Val Ile Glu Ala Thr His Met Cys Met Val Met Arg Gly
        195                 200                 205

Val Gln Lys Met Asn Ser Lys Thr Val Thr Ser Thr Met Leu Gly Val
210                 215                 220

Phe Arg Glu Asp Pro Lys Thr Arg Glu Glu Phe Leu Thr Leu Ile Arg
225                 230                 235                 240

Ser

<210> SEQ ID NO 6
<211> LENGTH: 241
<212> TYPE: PRT
<213> ORGANISM: Mus musculus
<220> FEATURE:
<221> NAME/KEY: MISC_FEATURE
<222> LOCATION: (1)..(241)
<223> OTHER INFORMATION: GTP cyclohydrolase 1

<400> SEQUENCE: 6

Met Glu Lys Pro Arg Gly Val Arg Cys Thr Asn Gly Phe Ser Glu Arg
1               5                   10                  15

Glu Leu Pro Arg Pro Gly Ala Ser Pro Ala Glu Lys Ser Arg Pro
                20                  25                  30

Pro Glu Ala Lys Gly Ala Gln Pro Ala Asp Ala Trp Lys Ala Gly Arg
            35                  40                  45

His Arg Ser Glu Glu Glu Asn Gln Val Asn Leu Pro Lys Leu Ala Ala
        50                  55                  60

Ala Tyr Ser Ser Ile Leu Leu Ser Leu Gly Glu Asp Pro Gln Arg Gln
 65                  70                  75                  80

Gly Leu Leu Lys Thr Pro Trp Arg Ala Ala Thr Ala Met Gln Tyr Phe
                 85                  90                  95

Thr Lys Gly Tyr Gln Glu Thr Ile Ser Asp Val Leu Asn Asp Ala Ile
            100                 105                 110

Phe Asp Glu Asp His Asp Glu Met Val Ile Val Lys Asp Ile Asp Met
        115                 120                 125

Phe Ser Met Cys Glu His His Leu Val Pro Phe Val Gly Arg Val His
130                 135                 140

Ile Gly Tyr Leu Pro Asn Lys Gln Val Leu Gly Leu Ser Lys Leu Ala
145                 150                 155                 160

Arg Ile Val Glu Ile Tyr Ser Arg Arg Leu Gln Val Gln Glu Arg Leu
                165                 170                 175
```

```
Thr Lys Gln Ile Ala Val Ala Ile Thr Glu Ala Leu Gln Pro Ala Gly
            180                 185                 190

Val Gly Val Val Ile Glu Ala Thr His Met Cys Met Val Met Arg Gly
            195                 200                 205

Val Gln Lys Met Asn Ser Lys Thr Val Thr Ser Thr Met Leu Gly Val
210                 215                 220

Phe Arg Glu Asp Pro Lys Thr Arg Glu Glu Phe Leu Thr Leu Ile Arg
225                 230                 235                 240

Ser

<210> SEQ ID NO 7
<211> LENGTH: 497
<212> TYPE: PRT
<213> ORGANISM: Homo sapiens
<220> FEATURE:
<221> NAME/KEY: MISC_FEATURE
<222> LOCATION: (1)..(497)
<223> OTHER INFORMATION: Tyrosine 3-hydroxylase

<400> SEQUENCE: 7

Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Ser Pro
            20                  25                  30

Arg Phe Ile Gly Arg Arg Gln Ser Leu Ile Glu Asp Ala Arg Lys Glu
        35                  40                  45

Arg Glu Ala Ala Val Ala Ala Ala Ala Ala Val Pro Ser Glu Pro
50                  55                  60

Gly Asp Pro Leu Glu Ala Val Ala Phe Glu Glu Lys Glu Gly Lys Ala
65                  70                  75                  80

Val Leu Asn Leu Leu Phe Ser Pro Arg Ala Thr Lys Pro Ser Ala Leu
                85                  90                  95

Ser Arg Ala Val Lys Val Phe Glu Thr Phe Glu Ala Lys Ile His His
            100                 105                 110

Leu Glu Thr Arg Pro Ala Gln Arg Pro Arg Ala Gly Gly Pro His Leu
        115                 120                 125

Glu Tyr Phe Val Arg Leu Glu Val Arg Arg Gly Asp Leu Ala Ala Leu
130                 135                 140

Leu Ser Gly Val Arg Gln Val Ser Glu Asp Val Arg Ser Pro Ala Gly
145                 150                 155                 160

Pro Lys Val Pro Trp Phe Pro Arg Lys Val Ser Glu Leu Asp Lys Cys
                165                 170                 175

His His Leu Val Thr Lys Phe Asp Pro Asp Leu Asp Leu Asp His Pro
            180                 185                 190

Gly Phe Ser Asp Gln Val Tyr Arg Gln Arg Arg Lys Leu Ile Ala Glu
        195                 200                 205

Ile Ala Phe Gln Tyr Arg His Gly Asp Pro Ile Pro Arg Val Glu Tyr
210                 215                 220

Thr Ala Glu Glu Ile Ala Thr Trp Lys Glu Val Tyr Thr Thr Leu Lys
225                 230                 235                 240

Gly Leu Tyr Ala Thr His Ala Cys Gly Glu His Leu Glu Ala Phe Ala
                245                 250                 255

Leu Leu Glu Arg Phe Ser Gly Tyr Arg Glu Asp Asn Ile Pro Gln Leu
            260                 265                 270

Glu Asp Val Ser Arg Phe Leu Lys Glu Arg Thr Gly Phe Gln Leu Arg
```

```
            275                 280                 285
Pro Val Ala Gly Leu Leu Ser Ala Arg Asp Phe Leu Ala Ser Leu Ala
290                 295                 300

Phe Arg Val Phe Gln Cys Thr Gln Tyr Ile Arg His Ala Ser Ser Pro
305                 310                 315                 320

Met His Ser Pro Glu Pro Asp Cys Cys His Glu Leu Leu Gly His Val
                325                 330                 335

Pro Met Leu Ala Asp Arg Thr Phe Ala Gln Phe Ser Gln Asp Ile Gly
            340                 345                 350

Leu Ala Ser Leu Gly Ala Ser Asp Glu Glu Ile Glu Lys Leu Ser Thr
        355                 360                 365

Leu Tyr Trp Phe Thr Val Glu Phe Gly Leu Cys Lys Gln Asn Gly Glu
370                 375                 380

Val Lys Ala Tyr Gly Ala Gly Leu Leu Ser Ser Tyr Gly Glu Leu Leu
385                 390                 395                 400

His Cys Leu Ser Glu Glu Pro Glu Ile Arg Ala Phe Asp Pro Glu Ala
                405                 410                 415

Ala Ala Val Gln Pro Tyr Gln Asp Gln Thr Tyr Gln Ser Val Tyr Phe
            420                 425                 430

Val Ser Glu Ser Phe Ser Asp Ala Lys Asp Lys Leu Arg Ser Tyr Ala
        435                 440                 445

Ser Arg Ile Gln Arg Pro Phe Ser Val Lys Phe Asp Pro Tyr Thr Leu
450                 455                 460

Ala Ile Asp Val Leu Asp Ser Pro Gln Ala Val Arg Arg Ser Leu Glu
465                 470                 475                 480

Gly Val Gln Asp Glu Leu Asp Thr Leu Ala His Ala Leu Ser Ala Ile
                485                 490                 495

Gly

<210> SEQ ID NO 8
<211> LENGTH: 528
<212> TYPE: PRT
<213> ORGANISM: Homo sapiens
<220> FEATURE:
<221> NAME/KEY: MISC_FEATURE
<222> LOCATION: (1)..(528)
<223> OTHER INFORMATION: Tyrosine 3-monooxygenase

<400> SEQUENCE: 8

Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Val Arg
            20                  25                  30

Gly Gln Gly Ala Pro Gly Pro Ser Leu Thr Gly Ser Pro Trp Pro Gly
        35                  40                  45

Thr Ala Ala Pro Ala Ala Ser Tyr Thr Pro Thr Pro Arg Ser Pro Arg
    50                  55                  60

Phe Ile Gly Arg Arg Gln Ser Leu Ile Glu Asp Ala Arg Lys Glu Arg
65                  70                  75                  80

Glu Ala Ala Val Ala Ala Ala Ala Ala Val Pro Ser Glu Pro Gly
                85                  90                  95

Asp Pro Leu Glu Ala Val Ala Phe Glu Glu Lys Glu Gly Lys Ala Val
            100                 105                 110

Leu Asn Leu Leu Phe Ser Pro Arg Ala Thr Lys Pro Ser Ala Leu Ser
        115                 120                 125
```

Arg Ala Val Lys Val Phe Glu Thr Phe Glu Ala Lys Ile His His Leu
            130                 135                 140

Glu Thr Arg Pro Ala Gln Arg Pro Arg Ala Gly Gly Pro His Leu Glu
145                 150                 155                 160

Tyr Phe Val Arg Leu Glu Val Arg Arg Gly Asp Leu Ala Ala Leu Leu
                165                 170                 175

Ser Gly Val Arg Gln Val Ser Glu Asp Val Arg Ser Pro Ala Gly Pro
            180                 185                 190

Lys Val Pro Trp Phe Pro Arg Lys Val Ser Glu Leu Asp Lys Cys His
        195                 200                 205

His Leu Val Thr Lys Phe Asp Pro Asp Leu Asp His Pro Gly
210                 215                 220

Phe Ser Asp Gln Val Tyr Arg Gln Arg Lys Leu Ile Ala Glu Ile
225                 230                 235                 240

Ala Phe Gln Tyr Arg His Gly Asp Pro Ile Pro Arg Val Glu Tyr Thr
                245                 250                 255

Ala Glu Glu Ile Ala Thr Trp Lys Glu Val Tyr Thr Thr Leu Lys Gly
            260                 265                 270

Leu Tyr Ala Thr His Ala Cys Gly Glu His Leu Glu Ala Phe Ala Leu
        275                 280                 285

Leu Glu Arg Phe Ser Gly Tyr Arg Glu Asp Asn Ile Pro Gln Leu Glu
290                 295                 300

Asp Val Ser Arg Phe Leu Lys Glu Arg Thr Gly Phe Gln Leu Arg Pro
305                 310                 315                 320

Val Ala Gly Leu Leu Ser Ala Arg Asp Phe Leu Ala Ser Leu Ala Phe
                325                 330                 335

Arg Val Phe Gln Cys Thr Gln Tyr Ile Arg His Ala Ser Ser Pro Met
            340                 345                 350

His Ser Pro Glu Pro Asp Cys Cys His Glu Leu Leu Gly His Val Pro
        355                 360                 365

Met Leu Ala Asp Arg Thr Phe Ala Gln Phe Ser Gln Asp Ile Gly Leu
370                 375                 380

Ala Ser Leu Gly Ala Ser Asp Glu Glu Ile Glu Lys Leu Ser Thr Leu
385                 390                 395                 400

Tyr Trp Phe Thr Val Glu Phe Gly Leu Cys Lys Gln Asn Gly Glu Val
                405                 410                 415

Lys Ala Tyr Gly Ala Gly Leu Leu Ser Ser Tyr Gly Glu Leu Leu His
            420                 425                 430

Cys Leu Ser Glu Glu Pro Glu Ile Arg Ala Phe Asp Pro Glu Ala Ala
        435                 440                 445

Ala Val Gln Pro Tyr Gln Asp Gln Thr Tyr Gln Ser Val Tyr Phe Val
450                 455                 460

Ser Glu Ser Phe Ser Asp Ala Lys Asp Lys Leu Arg Ser Tyr Ala Ser
465                 470                 475                 480

Arg Ile Gln Arg Pro Phe Ser Val Lys Phe Asp Pro Tyr Thr Leu Ala
                485                 490                 495

Ile Asp Val Leu Asp Ser Pro Gln Ala Val Arg Arg Ser Leu Glu Gly
            500                 505                 510

Val Gln Asp Glu Leu Asp Thr Leu Ala His Ala Leu Ser Ala Ile Gly
        515                 520                 525

<210> SEQ ID NO 9
<211> LENGTH: 497
<212> TYPE: PRT

<213> ORGANISM: Homo sapiens
<220> FEATURE:
<221> NAME/KEY: MISC_FEATURE
<222> LOCATION: (1)..(497)
<223> OTHER INFORMATION: Tyrosine hydroxylase

<400> SEQUENCE: 9

```
Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Ser Pro
            20                  25                  30

Arg Phe Ile Gly Arg Arg Gln Ser Leu Ile Glu Asp Ala Arg Lys Glu
        35                  40                  45

Arg Glu Ala Ala Val Ala Ala Ala Ala Ala Val Pro Ser Glu Pro
    50                  55                  60

Gly Asp Pro Leu Glu Ala Val Ala Phe Glu Glu Lys Glu Gly Lys Ala
65                  70                  75                  80

Met Leu Asn Leu Leu Phe Ser Pro Arg Ala Thr Lys Pro Ser Ala Leu
                85                  90                  95

Ser Arg Ala Val Lys Val Phe Glu Thr Phe Glu Ala Lys Ile His His
            100                 105                 110

Leu Glu Thr Arg Pro Ala Gln Arg Pro Arg Ala Gly Gly Pro His Leu
        115                 120                 125

Glu Tyr Phe Val Arg Leu Glu Val Arg Arg Gly Asp Leu Ala Ala Leu
    130                 135                 140

Leu Ser Gly Val Arg Gln Val Ser Glu Asp Val Arg Ser Pro Ala Gly
145                 150                 155                 160

Pro Lys Val Pro Trp Phe Pro Arg Lys Val Ser Glu Leu Asp Lys Cys
                165                 170                 175

His His Leu Val Thr Lys Phe Asp Pro Asp Leu Asp Leu Asp His Pro
            180                 185                 190

Gly Phe Ser Asp Gln Val Tyr Arg Gln Arg Arg Lys Leu Ile Ala Glu
        195                 200                 205

Ile Ala Phe Gln Tyr Arg His Gly Asp Pro Ile Pro Arg Val Glu Tyr
    210                 215                 220

Thr Ala Glu Glu Ile Ala Thr Trp Lys Glu Val Tyr Thr Thr Leu Lys
225                 230                 235                 240

Gly Leu Tyr Ala Thr His Ala Cys Gly Glu His Leu Glu Ala Phe Ala
                245                 250                 255

Leu Leu Glu Arg Phe Ser Gly Tyr Arg Glu Asp Asn Ile Pro Gln Leu
            260                 265                 270

Glu Asp Val Ser Arg Phe Leu Lys Glu Arg Thr Gly Phe Gln Leu Arg
        275                 280                 285

Pro Val Ala Gly Leu Leu Ser Ala Arg Asp Phe Leu Ala Ser Leu Ala
    290                 295                 300

Phe Arg Val Phe Gln Cys Thr Gln Tyr Ile Arg His Ala Ser Ser Pro
305                 310                 315                 320

Met His Ser Pro Glu Pro Asp Cys Cys His Glu Leu Leu Gly His Val
                325                 330                 335

Pro Met Leu Ala Asp Arg Thr Phe Ala Gln Phe Ser Gln Asp Ile Gly
            340                 345                 350

Leu Ala Ser Leu Gly Ala Ser Asp Glu Glu Ile Glu Lys Leu Ser Thr
        355                 360                 365

Leu Tyr Trp Phe Thr Val Glu Phe Gly Leu Cys Lys Gln Asn Gly Glu
    370                 375                 380
```

```
Val Lys Ala Tyr Gly Ala Gly Leu Leu Ser Ser Tyr Gly Glu Leu Leu
385                 390                 395                 400

His Cys Leu Ser Glu Glu Pro Glu Ile Arg Ala Phe Asp Pro Glu Ala
            405                 410                 415

Ala Ala Val Gln Pro Tyr Gln Asp Gln Thr Tyr Gln Ser Val Tyr Phe
        420                 425                 430

Val Ser Glu Ser Phe Ser Asp Ala Lys Asp Lys Leu Arg Ser Tyr Ala
    435                 440                 445

Ser Arg Ile Gln Arg Pro Phe Ser Val Lys Phe Asp Pro Tyr Thr Leu
450                 455                 460

Ala Ile Asp Val Leu Asp Ser Pro Gln Ala Val Arg Arg Ser Leu Glu
465                 470                 475                 480

Gly Val Gln Asp Glu Leu Asp Thr Leu Ala His Ala Leu Ser Ala Ile
                485                 490                 495

Gly
```

<210> SEQ ID NO 10
<211> LENGTH: 501
<212> TYPE: PRT
<213> ORGANISM: Homo sapiens
<220> FEATURE:
<221> NAME/KEY: MISC_FEATURE
<222> LOCATION: (1)..(501)
<223> OTHER INFORMATION: Tyrosine hydroxylase

<400> SEQUENCE: 10

```
Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Val Arg
            20                  25                  30

Gly Gln Ser Pro Arg Phe Ile Gly Arg Arg Gln Ser Leu Ile Glu Asp
        35                  40                  45

Ala Arg Lys Glu Arg Glu Ala Ala Val Ala Ala Ala Ala Ala Ala Val
    50                  55                  60

Pro Ser Glu Pro Gly Asp Pro Leu Glu Ala Val Ala Phe Glu Glu Lys
65                  70                  75                  80

Glu Gly Lys Ala Met Leu Asn Leu Leu Phe Ser Pro Arg Ala Thr Lys
                85                  90                  95

Pro Ser Ala Leu Ser Arg Ala Val Lys Val Phe Glu Thr Phe Glu Ala
            100                 105                 110

Lys Ile His His Leu Glu Thr Arg Pro Ala Gln Arg Pro Arg Ala Gly
        115                 120                 125

Gly Pro His Leu Glu Tyr Phe Val Arg Leu Glu Val Arg Arg Gly Asp
    130                 135                 140

Leu Ala Ala Leu Leu Ser Gly Val Arg Gln Val Ser Glu Asp Val Arg
145                 150                 155                 160

Ser Pro Ala Gly Pro Lys Val Pro Trp Phe Pro Arg Lys Val Ser Glu
                165                 170                 175

Leu Asp Lys Cys His His Leu Val Thr Lys Phe Asp Pro Asp Leu Asp
            180                 185                 190

Leu Asp His Pro Gly Phe Ser Asp Gln Val Tyr Arg Gln Arg Arg Lys
        195                 200                 205

Leu Ile Ala Glu Ile Ala Phe Gln Tyr Arg His Gly Asp Pro Ile Pro
    210                 215                 220

Arg Val Glu Tyr Thr Ala Glu Glu Ile Ala Thr Trp Lys Glu Val Tyr
```

```
            225                 230                 235                 240

Thr Thr Leu Lys Gly Leu Tyr Ala Thr His Ala Cys Gly Glu His Leu
                        245                 250                 255

Glu Ala Phe Ala Leu Leu Glu Arg Phe Ser Gly Tyr Arg Glu Asp Asn
                        260                 265                 270

Ile Pro Gln Leu Glu Asp Val Ser Arg Phe Leu Lys Glu Arg Thr Gly
                        275                 280                 285

Phe Gln Leu Arg Pro Val Ala Gly Leu Leu Ser Ala Arg Asp Phe Leu
                        290                 295                 300

Ala Ser Leu Ala Phe Arg Val Phe Gln Cys Thr Gln Tyr Ile Arg His
        305                 310                 315                 320

Ala Ser Ser Pro Met His Ser Pro Glu Pro Asp Cys Cys His Glu Leu
                        325                 330                 335

Leu Gly His Val Pro Met Leu Ala Asp His Thr Phe Ala Gln Phe Ser
                        340                 345                 350

Gln Asp Ile Gly Leu Ala Ser Leu Gly Ala Ser Asp Glu Glu Ile Glu
                        355                 360                 365

Lys Leu Ser Thr Leu Tyr Trp Phe Thr Val Glu Phe Gly Leu Cys Lys
                        370                 375                 380

Gln Asn Gly Glu Val Lys Ala Tyr Gly Ala Gly Leu Leu Ser Ser Tyr
        385                 390                 395                 400

Gly Glu Leu Leu His Cys Leu Ser Glu Glu Pro Glu Ile Arg Ala Phe
                        405                 410                 415

Asp Pro Glu Ala Ala Ala Val Gln Pro Tyr Gln Asp Gln Thr Tyr Gln
                        420                 425                 430

Ser Val Tyr Phe Val Ser Glu Ser Phe Ser Asp Ala Lys Asp Lys Leu
                        435                 440                 445

Arg Ser Tyr Ala Ser Arg Ile Gln Arg Pro Phe Ser Val Lys Phe Asp
                        450                 455                 460

Pro Tyr Thr Leu Ala Ile Asp Val Leu Asp Ser Pro Gln Ala Val Arg
        465                 470                 475                 480

Arg Ser Leu Glu Gly Val Gln Asp Glu Leu Asp Thr Leu Ala His Ala
                        485                 490                 495

Leu Ser Ala Ile Gly
                        500

<210> SEQ ID NO 11
<211> LENGTH: 528
<212> TYPE: PRT
<213> ORGANISM: Homo sapiens
<220> FEATURE:
<221> NAME/KEY: MISC_FEATURE
<222> LOCATION: (1)..(528)
<223> OTHER INFORMATION: Tyrosine 3-monooxygenase

<400> SEQUENCE: 11

Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Val Arg
                20                  25                  30

Gly Gln Gly Ala Pro Gly Pro Ser Leu Thr Gly Ser Pro Trp Pro Gly
                35                  40                  45

Thr Ala Ala Pro Ala Ala Ser Tyr Thr Pro Thr Pro Arg Ser Pro Arg
            50                  55                  60

Phe Ile Gly Arg Arg Gln Ser Leu Ile Glu Asp Ala Arg Lys Glu Arg
65                  70                  75                  80
```

-continued

```
Glu Ala Ala Val Ala Ala Ala Ala Val Pro Ser Glu Pro Gly
                85                  90              95

Asp Pro Leu Glu Ala Val Ala Phe Glu Lys Glu Gly Lys Ala Val
            100             105             110

Leu Asn Leu Leu Phe Ser Pro Arg Ala Thr Lys Pro Ser Ala Leu Ser
        115             120             125

Arg Ala Val Lys Val Phe Glu Thr Phe Glu Ala Lys Ile His His Leu
    130             135             140

Glu Thr Arg Pro Ala Gln Arg Pro Arg Ala Gly Gly Pro His Leu Glu
145             150             155             160

Tyr Phe Val Arg Leu Glu Val Arg Arg Gly Asp Leu Ala Ala Leu Leu
                165             170             175

Ser Gly Val Arg Gln Val Ser Glu Asp Val Arg Ser Pro Ala Gly Pro
            180             185             190

Lys Val Pro Trp Phe Pro Arg Lys Val Ser Glu Leu Asp Lys Cys His
        195             200             205

His Leu Val Thr Lys Phe Asp Pro Asp Leu Asp His Pro Gly
    210             215             220

Phe Ser Asp Gln Val Tyr Arg Gln Arg Lys Leu Ile Ala Glu Ile
225             230             235             240

Ala Phe Gln Tyr Arg His Gly Asp Pro Ile Pro Arg Val Glu Tyr Thr
                245             250             255

Ala Glu Glu Ile Ala Thr Trp Lys Glu Val Tyr Thr Thr Leu Lys Gly
            260             265             270

Leu Tyr Ala Thr His Ala Cys Gly Glu His Leu Glu Ala Phe Ala Leu
        275             280             285

Leu Glu Arg Phe Ser Gly Tyr Arg Glu Asp Asn Ile Pro Gln Leu Glu
    290             295             300

Asp Val Ser Arg Phe Leu Lys Glu Arg Thr Gly Phe Gln Leu Arg Pro
305             310             315             320

Val Ala Gly Leu Leu Ser Ala Arg Asp Phe Leu Ala Ser Leu Ala Phe
                325             330             335

Arg Val Phe Gln Cys Thr Gln Tyr Ile Arg His Ala Ser Ser Pro Met
            340             345             350

His Ser Pro Glu Pro Asp Cys Cys His Glu Leu Leu Gly His Val Pro
        355             360             365

Met Leu Ala Asp Arg Thr Phe Ala Gln Phe Ser Gln Asp Ile Gly Leu
    370             375             380

Ala Ser Leu Gly Ala Ser Asp Glu Glu Ile Glu Lys Leu Ser Thr Leu
385             390             395             400

Tyr Trp Phe Thr Val Glu Phe Gly Leu Cys Lys Gln Asn Gly Glu Val
                405             410             415

Lys Ala Tyr Gly Ala Gly Leu Leu Ser Ser Tyr Gly Glu Leu Leu His
            420             425             430

Cys Leu Ser Glu Glu Pro Glu Ile Arg Ala Phe Asp Pro Glu Ala Ala
        435             440             445

Ala Val Gln Pro Tyr Gln Asp Gln Thr Tyr Gln Ser Val Tyr Phe Val
    450             455             460

Ser Glu Ser Phe Ser Asp Ala Lys Asp Lys Leu Arg Ser Tyr Ala Ser
465             470             475             480

Arg Ile Gln Arg Pro Phe Ser Val Lys Phe Asp Pro Tyr Thr Leu Ala
                485             490             495
```

```
Ile Asp Val Leu Asp Ser Pro Gln Ala Val Arg Arg Ser Leu Glu Gly
            500                 505                 510

Val Gln Asp Glu Leu Asp Thr Leu Ala His Ala Leu Ser Ala Ile Gly
515                 520                 525
```

<210> SEQ ID NO 12
<211> LENGTH: 528
<212> TYPE: PRT
<213> ORGANISM: Homo sapiens
<220> FEATURE:
<221> NAME/KEY: MISC_FEATURE
<222> LOCATION: (1)..(528)
<223> OTHER INFORMATION: Tyrosine 3-monooxygenase

<400> SEQUENCE: 12

```
Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Val Arg
            20                  25                  30

Gly Gln Gly Ala Pro Gly Pro Ser Leu Thr Gly Ser Pro Trp Pro Gly
        35                  40                  45

Thr Ala Ala Pro Ala Ala Ser Tyr Thr Pro Thr Pro Arg Ser Pro Arg
    50                  55                  60

Phe Ile Gly Arg Arg Gln Ser Leu Ile Glu Asp Ala Arg Lys Glu Arg
65                  70                  75                  80

Glu Ala Ala Val Ala Ala Ala Ala Ala Val Pro Ser Glu Pro Gly
                85                  90                  95

Asp Pro Leu Glu Ala Val Ala Phe Glu Glu Lys Glu Gly Lys Ala Val
            100                 105                 110

Leu Asn Leu Leu Phe Ser Pro Arg Ala Thr Lys Pro Ser Ala Leu Ser
        115                 120                 125

Arg Ala Val Lys Val Phe Glu Thr Phe Glu Ala Lys Ile His His Leu
130                 135                 140

Glu Thr Arg Pro Ala Gln Arg Pro Arg Ala Gly Gly Pro His Leu Glu
145                 150                 155                 160

Tyr Phe Val Arg Leu Glu Val Arg Arg Gly Asp Leu Ala Ala Leu Leu
                165                 170                 175

Ser Gly Val Arg Gln Val Ser Glu Asp Val Arg Ser Pro Ala Gly Pro
            180                 185                 190

Lys Val Pro Trp Phe Pro Arg Lys Val Ser Glu Leu Asp Lys Cys His
        195                 200                 205

His Leu Val Thr Lys Phe Asp Pro Asp Leu Asp His Pro Gly
    210                 215                 220

Phe Ser Asp Gln Val Tyr Arg Gln Arg Arg Lys Leu Ile Ala Glu Ile
225                 230                 235                 240

Ala Phe Gln Tyr Arg His Gly Asp Pro Ile Pro Arg Val Glu Tyr Thr
                245                 250                 255

Ala Glu Glu Ile Ala Thr Trp Lys Glu Val Tyr Thr Thr Leu Lys Gly
            260                 265                 270

Leu Tyr Ala Thr His Ala Cys Gly Glu His Leu Glu Ala Phe Ala Leu
        275                 280                 285

Leu Glu Arg Phe Ser Gly Tyr Arg Glu Asp Asn Ile Pro Gln Leu Glu
    290                 295                 300

Asp Val Ser Arg Phe Leu Lys Glu Arg Thr Gly Phe Gln Leu Arg Pro
305                 310                 315                 320

Val Ala Gly Leu Leu Ser Ala Arg Asp Phe Leu Ala Ser Leu Ala Phe
```

```
                    325                 330                 335
Arg Val Phe Gln Cys Thr Gln Tyr Ile Arg His Ala Ser Ser Pro Met
                340                 345                 350

His Ser Pro Glu Pro Asp Cys Cys His Glu Leu Leu Gly His Val Pro
                355                 360                 365

Met Leu Ala Asp Arg Thr Phe Ala Gln Phe Ser Gln Asp Ile Gly Leu
                370                 375                 380

Ala Ser Leu Gly Ala Ser Asp Glu Glu Ile Glu Lys Leu Ser Thr Leu
385                 390                 395                 400

Tyr Trp Phe Thr Val Glu Phe Gly Leu Cys Lys Gln Asn Gly Glu Val
                405                 410                 415

Lys Ala Tyr Gly Ala Gly Leu Leu Ser Ser Tyr Gly Glu Leu Leu His
                420                 425                 430

Cys Leu Ser Glu Glu Pro Glu Ile Arg Ala Phe Asp Pro Glu Ala Ala
                435                 440                 445

Ala Val Gln Pro Tyr Gln Asp Gln Thr Tyr Gln Ser Val Tyr Phe Val
                450                 455                 460

Ser Glu Ser Phe Ser Asp Ala Lys Asp Lys Leu Arg Ser Tyr Ala Ser
465                 470                 475                 480

Arg Ile Gln Arg Pro Phe Ser Val Lys Phe Asp Pro Tyr Thr Leu Ala
                485                 490                 495

Ile Asp Val Leu Asp Ser Pro Gln Ala Val Arg Arg Ser Leu Glu Gly
                500                 505                 510

Val Gln Asp Glu Leu Asp Thr Leu Ala His Ala Leu Ser Ala Ile Gly
                515                 520                 525

<210> SEQ ID NO 13
<211> LENGTH: 498
<212> TYPE: PRT
<213> ORGANISM: Rattus norvegicus
<220> FEATURE:
<221> NAME/KEY: MISC_FEATURE
<222> LOCATION: (1)..(498)
<223> OTHER INFORMATION: Tyrosine 3-hydroxylase

<400> SEQUENCE: 13

Met Pro Thr Pro Ser Ala Pro Ser Pro Gln Pro Lys Gly Phe Arg Arg
1               5                   10                  15

Ala Val Ser Glu Gln Asp Ala Lys Gln Ala Glu Ala Val Thr Ser Pro
                20                  25                  30

Arg Phe Ile Gly Arg Arg Gln Ser Leu Ile Glu Asp Ala Arg Lys Glu
                35                  40                  45

Arg Glu Ala Ala Ala Ala Ala Ala Ala Ala Val Ala Ser Ser Glu
        50                  55                  60

Pro Gly Asn Pro Leu Glu Ala Val Val Phe Glu Glu Arg Asp Gly Asn
65                  70                  75                  80

Ala Val Leu Asn Leu Leu Phe Ser Leu Arg Gly Thr Lys Pro Ser Ser
                85                  90                  95

Leu Ser Arg Ala Val Lys Val Phe Glu Thr Phe Glu Ala Lys Ile His
                100                 105                 110

His Leu Glu Thr Arg Pro Ala Gln Arg Pro Leu Ala Gly Ser Pro His
                115                 120                 125

Leu Glu Tyr Phe Val Arg Phe Glu Val Pro Ser Gly Asp Leu Ala Ala
                130                 135                 140

Leu Leu Ser Ser Val Arg Arg Val Ser Asp Asp Val Arg Ser Ala Arg
145                 150                 155                 160
```

Glu Asp Lys Val Pro Trp Phe Pro Arg Lys Val Ser Glu Leu Asp Lys
                165                 170                 175

Cys His His Leu Val Thr Lys Phe Asp Pro Asp Leu Asp Leu Asp His
            180                 185                 190

Pro Gly Phe Ser Asp Gln Val Tyr Arg Gln Arg Arg Lys Leu Ile Ala
        195                 200                 205

Glu Ile Ala Phe Gln Tyr Lys His Gly Glu Pro Ile Pro His Val Glu
    210                 215                 220

Tyr Thr Ala Glu Glu Ile Ala Thr Trp Lys Glu Val Tyr Val Thr Leu
225                 230                 235                 240

Lys Gly Leu Tyr Ala Thr His Ala Cys Arg Glu His Leu Glu Gly Phe
                245                 250                 255

Gln Leu Leu Glu Arg Tyr Cys Gly Tyr Arg Glu Asp Ser Ile Pro Gln
            260                 265                 270

Leu Glu Asp Val Ser Arg Phe Leu Lys Glu Arg Thr Gly Phe Gln Leu
        275                 280                 285

Arg Pro Val Ala Gly Leu Leu Ser Ala Arg Asp Phe Leu Ala Ser Leu
    290                 295                 300

Ala Phe Arg Val Phe Gln Cys Thr Gln Tyr Ile Arg His Ala Ser Ser
305                 310                 315                 320

Pro Met His Ser Pro Glu Pro Asp Cys Cys His Glu Leu Leu Gly His
                325                 330                 335

Val Pro Met Leu Ala Asp Arg Thr Phe Ala Gln Phe Ser Gln Asp Ile
            340                 345                 350

Gly Leu Ala Ser Leu Gly Ala Ser Asp Glu Glu Ile Glu Lys Leu Ser
        355                 360                 365

Thr Val Tyr Trp Phe Thr Val Glu Phe Gly Leu Cys Lys Gln Asn Gly
    370                 375                 380

Glu Leu Lys Ala Tyr Gly Ala Gly Leu Leu Ser Ser Tyr Gly Glu Leu
385                 390                 395                 400

Leu His Ser Leu Ser Glu Glu Pro Glu Val Arg Ala Phe Asp Pro Asp
                405                 410                 415

Thr Ala Ala Val Gln Pro Tyr Gln Asp Gln Thr Tyr Gln Pro Val Tyr
            420                 425                 430

Phe Val Ser Glu Ser Phe Asn Asp Ala Lys Asp Lys Leu Arg Asn Tyr
        435                 440                 445

Ala Ser Arg Ile Gln Arg Pro Phe Ser Val Lys Phe Asp Pro Tyr Thr
    450                 455                 460

Leu Ala Ile Asp Val Leu Asp Ser Pro His Thr Ile Gln Arg Ser Leu
465                 470                 475                 480

Glu Gly Val Gln Asp Glu Leu His Thr Leu Ala His Ala Leu Ser Ala
                485                 490                 495

Ile Ser

<210> SEQ ID NO 14
<211> LENGTH: 498
<212> TYPE: PRT
<213> ORGANISM: Mus musculus
<220> FEATURE:
<221> NAME/KEY: MISC_FEATURE
<222> LOCATION: (1)..(498)
<223> OTHER INFORMATION: Tyrosine 3-hydroxylase

<400> SEQUENCE: 14

Met Pro Thr Pro Ser Ala Ser Ser Pro Gln Pro Lys Gly Phe Arg Arg

```
  1               5                   10                  15
Ala Val Ser Glu Gln Asp Thr Lys Gln Ala Glu Ala Val Thr Ser Pro
                20                  25                  30

Arg Phe Ile Gly Arg Arg Gln Ser Leu Ile Glu Asp Ala Arg Lys Glu
                35                  40                  45

Arg Glu Ala Ala Ala Ala Ala Ala Ala Ala Val Ala Ser Ala Glu
    50                  55                  60

Pro Gly Asn Pro Leu Glu Ala Val Val Phe Glu Glu Arg Asp Gly Asn
65                  70                  75                  80

Ala Val Leu Asn Leu Leu Phe Ser Leu Arg Gly Thr Lys Pro Ser Ser
                85                  90                  95

Leu Ser Arg Ala Leu Lys Val Phe Glu Thr Phe Glu Ala Lys Ile His
                100                 105                 110

His Leu Glu Thr Arg Pro Ala Gln Arg Pro Leu Ala Gly Ser Pro His
                115                 120                 125

Leu Glu Tyr Phe Val Arg Phe Glu Val Pro Ser Gly Asp Leu Ala Ala
                130                 135                 140

Leu Leu Ser Ser Val Arg Arg Val Ser Asp Asp Val Arg Ser Ala Arg
145                 150                 155                 160

Glu Asp Lys Val Pro Trp Phe Pro Arg Lys Val Ser Glu Leu Asp Lys
                165                 170                 175

Cys His His Leu Val Thr Lys Phe Asp Pro Asp Leu Asp Leu Asp His
                180                 185                 190

Pro Gly Phe Ser Asp Gln Ala Tyr Arg Gln Arg Arg Lys Leu Ile Ala
                195                 200                 205

Glu Ile Ala Phe Gln Tyr Lys Gln Gly Glu Pro Ile Pro His Val Glu
                210                 215                 220

Tyr Thr Lys Glu Glu Ile Ala Thr Trp Lys Glu Val Tyr Ala Thr Leu
225                 230                 235                 240

Lys Gly Leu Tyr Ala Thr His Ala Cys Arg Glu His Leu Glu Ala Phe
                245                 250                 255

Gln Leu Leu Glu Arg Tyr Cys Gly Tyr Arg Glu Asp Ser Ile Pro Gln
                260                 265                 270

Leu Glu Asp Val Ser His Phe Leu Lys Glu Arg Thr Gly Phe Gln Leu
                275                 280                 285

Arg Pro Val Ala Gly Leu Leu Ser Ala Arg Asp Phe Leu Ala Ser Leu
                290                 295                 300

Ala Phe Arg Val Phe Gln Cys Thr Gln Tyr Ile Arg His Ala Ser Ser
305                 310                 315                 320

Pro Met His Ser Pro Glu Pro Asp Cys Cys His Glu Leu Leu Gly His
                325                 330                 335

Val Pro Met Leu Ala Asp Arg Thr Phe Ala Gln Phe Ser Gln Asp Ile
                340                 345                 350

Gly Leu Ala Ser Leu Gly Ala Ser Asp Glu Glu Ile Glu Lys Leu Ser
                355                 360                 365

Thr Val Tyr Trp Phe Thr Val Glu Phe Gly Leu Cys Lys Gln Asn Gly
                370                 375                 380

Glu Leu Lys Ala Tyr Gly Ala Gly Leu Leu Ser Ser Tyr Gly Glu Leu
385                 390                 395                 400

Leu His Ser Leu Ser Glu Glu Pro Glu Val Arg Ala Phe Asp Pro Asp
                405                 410                 415

Thr Ala Ala Val Gln Pro Tyr Gln Asp Gln Thr Tyr Gln Pro Val Tyr
                420                 425                 430
```

```
Phe Val Ser Glu Ser Phe Ser Asp Ala Lys Asp Lys Leu Arg Asn Tyr
            435                 440                 445

Ala Ser Arg Ile Gln Arg Pro Phe Ser Val Lys Phe Asp Pro Tyr Thr
    450                 455                 460

Leu Ala Ile Asp Val Leu Asp Ser Pro His Thr Ile Arg Arg Ser Leu
465                 470                 475                 480

Glu Gly Val Gln Asp Glu Leu His Thr Leu Thr Gln Ala Leu Ser Ala
                485                 490                 495

Ile Ser

<210> SEQ ID NO 15
<211> LENGTH: 145
<212> TYPE: DNA
<213> ORGANISM: adeno-associated virus 2
<220> FEATURE:
<221> NAME/KEY: misc_feature
<222> LOCATION: (1)..(145)
<223> OTHER INFORMATION: left terminal sequence

<400> SEQUENCE: 15
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg   120
gccaactcca tcactagggg ttcct                                         145

<210> SEQ ID NO 16
<211> LENGTH: 145
<212> TYPE: DNA
<213> ORGANISM: adeno-associated virus 2
<220> FEATURE:
<221> NAME/KEY: misc_feature
<222> LOCATION: (1)..(145)
<223> OTHER INFORMATION: right terminal sequence

<400> SEQUENCE: 16
aggaacccct agtgatggag ttggccactc cctctctgcg cgctcgctcg ctcactgagg    60
ccgcccgggc aaagcccggg cgtcgggcga cctttggtcg cccggcctca gtgagcgagc   120
gagcgcgcag agagggagtg gccaa                                         145

<210> SEQ ID NO 17
<211> LENGTH: 484
<212> TYPE: DNA
<213> ORGANISM: Homo sapiens
<220> FEATURE:
<221> NAME/KEY: misc_feature
<222> LOCATION: (1)..(484)
<223> OTHER INFORMATION: Synapsin 1 (SYN1) promoter sequence

<400> SEQUENCE: 17
ctagactcta gctgcagagg gacctgcgta tgagtgcaag tgggttttag gaccaggatg    60
aggcggggtg ggggtgccta cctgacgacc gaccccgacc cactgacaa gcacccaacc   120 cccattcccc aaattgcgca tccctatca gagaggggga ggggaaacag gatgcggcga   180
ggcgcgtgcg cactgccagc ttcagcaccg cggacagtgc cttcgccccc gcctggcggc   240
gcgcgccacc gccgcctcag cactgaaggc gcgctgacgt cactcgccgg tcccccgcaa   300
actccccttc ccggccacct tggtcgcgtc cgcgccgccg ccgcccagc cggaccgcac   360 cacgcgaggc gcgagatagg ggggcacggg cgcgaccatc tgcgctgcgg cgccggcgac   420
tcagcgctgc ctcagtctgc ggtgggcagc ggaggagtcg tgtcgtgcct gagagcgcag   480
``` tcga                                                                484

<210> SEQ ID NO 18
<211> LENGTH: 753
<212> TYPE: DNA
<213> ORGANISM: Homo sapiens
<220> FEATURE:
<221> NAME/KEY: misc_feature
<222> LOCATION: (1)..(753)
<223> OTHER INFORMATION: GTP cyclohydrolase 1 (GCH1), transcript
      variant 1

<400> SEQUENCE: 18
atggagaagg ccctgtgcg ggcaccggcg gagaagccgc ggggcgccag gtgcagcaat      60
gggttccccg agcgggatcc gccgcggccc gggcccagca ggccggcgga aagcccccg    120 cggcccgagg ccaagagcgc gcagcccgcg gacggctgga agggcgagcg gccccgcagc   180
gaggaggata acgagctgaa cctccctaac ctggcagccg cctactcgtc catcctgagc   240
tcgctgggcg agaaccccca gcggcaaggg ctgctcaaga cgccctggag gcggcctcg    300 gccatgcagt tcttcaccaa gggctaccag agaccatct cagatgtcct aaacgatgct    360
atatttgatg aagatcatga tgagatggtg attgtgaagg acatagacat gttttccatg    420
tgtgagcatc acttggttcc atttgttgga aaggtccata ttggttatct tcctaacaag    480
caagtccttg gcctcagcaa acttgcgagg attgtagaaa tctatagtag aagactacaa    540
gttcaggagc gccttacaaa acaaattgct gtagcaatca cggaagcctt gcggcctgct    600
ggagtcgggg tagtggttga agcaacacac atgtgtatgg taatgcgagg tgtacagaaa    660
atgaacagca aaactgtgac cagcacaatg ttgggtgtgt ccgggagga tccaaagact    720 cgggaagagt tcctgactct cattaggagc taa                                  753

<210> SEQ ID NO 19
<211> LENGTH: 155
<212> TYPE: DNA
<213> ORGANISM: Simian virus 40
<220> FEATURE:
<221> NAME/KEY: misc_feature
<222> LOCATION: (1)..(155)
<223> OTHER INFORMATION: early poly-adenylation sequence

<400> SEQUENCE: 19
ttcgagcaac ttgtttattg cagcttataa tggttacaaa taaagcaata gcatcacaaa    60
tttcacaaat aaagcatttt tttcactgca ttctagttgt ggtttgtcca aactcatcaa   120
tgtatcttat catgtctgga tcgtctagca tcgaa                               155

<210> SEQ ID NO 20
<211> LENGTH: 192
<212> TYPE: DNA
<213> ORGANISM: Simian virus 40
<220> FEATURE:
<221> NAME/KEY: misc_feature
<222> LOCATION: (1)..(192)
<223> OTHER INFORMATION: late poly-adenylation sequence

<400> SEQUENCE: 20
cagacatgat aagatacatt gatgagtttg gacaaaccac aactagaatg cagtgaaaaa    60
aatgctttat ttgtgaaatt tgtgatgcta ttgctttatt tgtaaccatt ataagctgca   120
ataaacaagt taacaacaac aattgcattc attttatgtt tcaggttcag ggggaggtgt   180
gggaggtttt tt                                                        192

<210> SEQ ID NO 21
<211> LENGTH: 1494
<212> TYPE: DNA
<213> ORGANISM: Homo sapiens
<220> FEATURE:
<221> NAME/KEY: misc_feature
<222> LOCATION: (1)..(1494)
<223> OTHER INFORMATION: Tyrosine hydroxylase (TH), transcript variant 2

<400> SEQUENCE: 21

| | | | | |
|---|---|---|---|---|
| atgcccaccc cgacgccac cacgccacag gccaagggct ccgcagggc cgtgtctgag | | | | 60 |
| ctggacgcca agcaggcaga ggccatcatg tccccgcggt tcattgggcg caggcagagc | | | | 120 |
| ctcatcgagg acgcccgcaa ggagcgggag gcggcggtgg cagcagcggc cgctgcagtc | | | | 180 |
| ccctcggagc ccggggaccc cctggaggct gtggcctttg aggagaagga ggggaaggcc | | | | 240 |
| gtgctaaacc tgctcttctc cccgagggcc accaagccct cggcgctgtc ccgagctgtg | | | | 300 |
| aaggtgtttg agacgtttga agccaaaatc caccatctag agacccggcc cgcccagagg | | | | 360 |
| ccgcgagctg ggggcccca cctggagtac ttcgtgcgcc tcgaggtgcg ccgaggggac | | | | 420 |
| ctggccgccc tgctcagtgg tgtgcgccag gtgtcagagg acgtgcgcag ccccgcgggg | | | | 480 |
| cccaaggtcc cctggttccc aagaaaagtg tcagagctgg acaagtgtca tcacctggtc | | | | 540 |
| accaagttcg accctgacct ggacttggac cacccgggct tctcggacca ggtgtaccgc | | | | 600 |
| cagcgcagga agctgattgc tgagatcgcc ttccagtaca ggcacggcga cccgattccc | | | | 660 |
| cgtgtggagt acaccgccga ggagattgcc acctggaagg aggtctacac cacgctgaag | | | | 720 |
| ggcctctacg ccacgcacgc ctgcggggag cacctggagg cctttgcttt gctggagcgc | | | | 780 |
| ttcagcggct accgggaaga caatatcccc cagctggagg acgtctcccg cttcctgaag | | | | 840 |
| gagcgcacgg gcttccagct gcggcctgtg gccggcctgc tgtccgcccg ggacttcctg | | | | 900 |
| gccagcctgg ccttccgcgt gttccagtgc acccagtata tccgccacgc gtcctcgccc | | | | 960 |
| atgcactccc ctgagccgga ctgctgccac gagctgctgg ggcacgtgcc catgctggcc | | | | 1020 |
| gaccgcacct cgcgcagtt ctcgcaggac attggcctgg cgtccctggg ggcctcggat | | | | 1080 |
| gaggaaattg agaagctgtc cacgctgtac tggttcacgg tggagttcgg gctgtgtaag | | | | 1140 |
| cagaacgggg aggtgaaggc ctatggtgcc gggctgctgt cctcctacgg ggagctcctg | | | | 1200 |
| cactgcctgt ctgaggagcc tgagattcgg gccttcgacc ctgaggctgc ggccgtgcag | | | | 1260 |
| ccctaccaag accagacgta ccagtcagtc tacttcgtgt ctgagagctt cagtgacgcc | | | | 1320 |
| aaggacaagc tcaggagcta tgcctcacgc atccagcgcc ccttctccgt gaagttcgac | | | | 1380 |
| ccgtacacgc tggccatcga cgtgctggac agccccagg ccgtgcggcg ctccctggag | | | | 1440 |
| ggtgtccagg atgagctgga cacccttgcc catgcgctga gtgccattgg ctaa | | | | 1494 |

<210> SEQ ID NO 22
<211> LENGTH: 610
<212> TYPE: DNA
<213> ORGANISM: Woodchuck hepatitis B virus
<220> FEATURE:
<221> NAME/KEY: misc_feature
<222> LOCATION: (1)..(610)
<223> OTHER INFORMATION: Woodchuck hepatitis B virus (WHV8)
    post-transcriptional regulatory element sequence

<400> SEQUENCE: 22

| | | | | |
|---|---|---|---|---|
| cgtcgacaat caacctctgg attacaaaat ttgtgaaaga ttgactggta ttcttaacta | | | | 60 |
| tgttgctcct tttacgctat gtggatacgc tgctttaatg cctttgtatc atgctattgc | | | | 120 |

| | |
|---|---|
| ttcccgtatg gctttcattt tctcctcctt gtataaatcc tggttgctgt ctctttatga | 180 |
| ggagttgtgg cccgttgtca ggcaacgtgg cgtggtgtgc actgtgtttg ctgacgcaac | 240 |
| ccccactggt tggggcattg ccaccacctg tcagctcctt tccgggactt tcgctttccc | 300 |
| cctccctatt gccacggcgg aactcatcgc cgcctgcctt gcccgctgct ggacaggggc | 360 |
| tcggctgttg ggcactgaca attccgtggt gttgtcgggg aagctgacgt cctttccatg | 420 |
| gctgctcgcc tgtgttgcca cctggattct gcgcgggacg tccttctgct acgtcccttc | 480 |
| ggccctcaat ccagcggacc ttccttcccg cggcctgctg ccggctctgc ggcctcttcc | 540 |
| gcgtcttcgc cttcgccctc agacgagtcg atctcccttt gggccgcct ccccgcctgg | 600 |
| aattcgagct | 610 |

<210> SEQ ID NO 23
<211> LENGTH: 4643
<212> TYPE: DNA
<213> ORGANISM: Artificial Sequence
<220> FEATURE:
<223> OTHER INFORMATION: Nucleic acid squence from a portion of a one-vector expression system

<400> SEQUENCE: 23

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctcagat cgggctgcag gaattggccg ctctagactc | 180 |
| tagctgcaga gggacctgcg tatgagtgca agtgggtttt aggaccagga tgaggcgggg | 240 |
| tgggggtgcc tacctgacga ccgaccccga cccactggac aagcacccaa cccccattcc | 300 |
| ccaaattgcg catcccctat cagagagggg aggggaaac aggatgcggc gaggcgcgtg | 360 |
| cgcactgcca gcttcagcac cgcggacagt gccttcgccc ccgcctggcg gcgcgcgcca | 420 |
| ccgccgcctc agcactgaag gcgcgctgac gtcactcgcc ggtcccccgc aaactcccct | 480 |
| tcccggccac cttggtcgcg tccgcgccgc cgccggccca gccggaccgc accacgcgag | 540 |
| gcgcgagata gggggcacg ggcgcgacca tctgcgctgc ggcgccggcg actcagcgct | 600 |
| gcctcagtct gcggtgggca gcggaggagt cgtgtcgtgc ctgagagcgc agtcgaattc | 660 |
| aagctgctag caaggatcca ccggtaacat ggagaagggc cctgtgcggg caccggcgga | 720 |
| gaagccgcgg ggcgccaggt gcagcaatgg gttccccgag cgggatccgc cgcggcccgg | 780 |
| gcccagcagg ccggcggaga agccccgcg gcccgaggcc aagagcgcgc agcccgcgga | 840 |
| cggctggaag ggcgagcggc cccgcagcga ggaggataac gagctgaacc tccctaacct | 900 |
| ggcagccgcc tactcgtcca tcctgagctc gctgggcgag aaccccagc ggcaagggct | 960 |
| gctcaagacg ccctggaggg cggcctcggc catgcagttc ttcaccaagg ctaccaggga | 1020 |
| gaccatctca gatgtcctaa acgatgctat atttgatgaa gatcatgatg agatggtgat | 1080 |
| tgtgaaggac atagacatgt tttccatgtg tgagcatcac ttggttccat tgttggaaa | 1140 |
| ggtccatatt ggttatcttc ctaacaagca agtccttggc ctcagcaaac ttgcgaggat | 1200 |
| tgtagaaatc tatagtagaa gactacaagt tcaggagcgc cttacaaaac aaattgctgt | 1260 |
| agcaatcacg gaagccttgc ggcctgctgg agtcggggta gtggttgaag caacacacat | 1320 |
| gtgtatggta atgcgaggtg tacagaaaat gaacagcaaa actgtgacca gcacaatgtt | 1380 |
| gggtgtgttc cggaggatc caaagactcg ggaagagttc ctgactctca ttaggagcta | 1440 |
| atgcatcccc atcgatgatc cagacatgat aagatacatt gatgagtttg gacaaaccac | 1500 |

```
aactagaatg cagtgaaaaa aatgctttat ttgtgaaatt tgtgatgcta ttgctttatt     1560
tgtaaccatt ataagctgca ataaacaagt taacaacaac aattgcattc attttatgtt     1620
tcaggttcag ggggaggtgt gggaggtttt ttagtcgacc gaattggccg ctctagactc     1680
tagctgcaga gggacctgcg tatgagtgca agtgggtttt aggaccagga tgaggcgggg     1740
tgggggtgcc tacctgacga ccgaccccga cccactggac aagcacccaa cccccattcc     1800
ccaaattgcg catccctat cagagagggg gaggggaaac aggatgcggc gaggcgcgtg      1860
cgcactgcca gcttcagcac cgcggacagt gccttcgccc ccgcctggcg gcgcgcgcca     1920
ccgccgcctc agcactgaag gcgcgctgac gtcactcgcc ggtccccgc aaactcccct      1980 tcccggccac cttggtcgcg tccgcgccgc cgccggccca gccggaccgc accacgcgag     2040
gcgcgagata gggggcacg ggcgcgacca tctgcgctgc ggcgccggcg actcagcgct      2100
gcctcagtct gcggtgggca gcggaggagt cgtgtcgtgc ctgagagcgc agtcgaattc     2160
aagctgctag caaggatcca ccggtcacca tgcccacccc cgacgccacc acgccacagg     2220
ccaagggctt ccgcagggcc gtgtctgagc tggacgccaa gcaggcagag gccatcatgt     2280
ccccgcggtt cattgggcgc aggcagagcc tcatcgagga cgcccgcaag gagcgggagg     2340
cggcggtggc agcagcggcc gctgcagtcc cctcggagcc cggggacccc ctggaggctg     2400
tggcctttga ggagaaggag gggaaggccg tgctaaacct gctcttctcc ccgagggcca     2460
ccaagccctc ggcgctgtcc cgagctgtga aggtgtttga gacgtttgaa gccaaaatcc     2520
accatctaga gacccggccc gccagaggc cgcgagctgg ggcccccac ctggagtact       2580 tcgtgcgcct cgaggtgcgc cgaggggacc tggccgccct gctcagtggt gtgcgccagg    2640
tgtcagagga cgtgcgcagc cccgcggggc ccaaggtccc ctggttccca agaaaagtgt    2700
cagagctgga caagtgtcat cacctggtca ccaagttcga ccctgacctg gacttggacc    2760
accgggcttt ctcggaccag gtgtaccgcc agcgcaggaa gctgattgct gagatcgcct    2820
tccagtacag gcacgcgac ccgattcccc gtgtggagta caccgccgag gagattgcca     2880
cctggaagga ggtctacacc acgctgaagg gcctctacgc cacgcacgcc tgcggggagc    2940
acctggaggc ctttgctttg ctggagcgct cagcggcta ccgggaagac aatatcccc      3000 agctggagga cgtctcccgc ttcctgaagg agcgcacggg cttccagctg cggcctgtgg    3060
ccggcctgct gtccgcccgg gacttcctgg ccagcctggc cttccgcgtg ttccagtgca    3120
cccagtatat ccgccacgcg tcctcgccca tgcactcccc tgagccggac tgctgccacg    3180
agctgctggg gcacgtgccc atgctggccg accgcacctt cgcgcagttc tcgcaggaca    3240
ttggcctggc gtccctgggg gcctcggatg aggaaattga gaagctgtcc acgctgtact    3300
ggttcacggt ggagttcggg ctgtgtaagc agaacgggga ggtgaaggcc tatggtgccg    3360
ggctgctgtc ctcctacggg gagctcctgc actgcctgtc tgaggagcct gagattcggg    3420
ccttcgaccc tgaggctgcg gccgtgcagc cctaccaaga ccagacgtac cagtcagtct    3480
acttcgtgtc tgagagcttc agtgacgcca aggacaagct caggagctat gcctcacgca    3540
tccagcgccc cttctccgtg aagttcgacc cgtacacgct ggccatcgac gtgctggaca    3600
gcccccaggc cgtgcggcgc tccctggagg gtgtccagga tgagctggac acccttgccc    3660
atgcgctgag tgccattggc taactagtgg atccgtcgac aatcaacctc tggattacaa    3720
aatttgtgaa agattgactg gtattcttaa ctatgttgct ccttttacgc tatgtggata    3780
cgctgcttta atgcctttgt atcatgctat tgcttcccgt atggctttca ttttctcctc    3840
cttgtataaa tcctggttgc tgtctcttta tgaggagttg tggcccgttg tcaggcaacg    3900
```

-continued

```
tggcgtggtg tgcactgtgt ttgctgacgc aaccccact ggttggggca ttgccaccac  3960
ctgtcagctc ctttccggga ctttcgcttt cccctccct attgccacgg cggaactcat  4020
cgccgcctgc cttgcccgct gctggacagg ggctcggctg ttgggcactg acaattccgt  4080
ggtgttgtcg gggaagctga cgtcctttcc atggctgctc gcctgtgttg ccacctggat  4140
tctgcgcggg acgtccttct gctacgtccc ttcggccctc aatccagcgg accttccttc  4200
ccgcggcctg ctgccggctc tgcggcctct tccgcgtctt cgccttcgcc ctcagacgag  4260
tcggatctcc ctttgggccg cctccccgcc tggaattcga gctcggtaca gcttatcgat  4320
accgtcgact tcgagcaact tgtttattgc agcttataat ggttacaaat aaagcaatag  4380
catcacaaat ttcacaaata aagcattttt ttcactgcat tctagttgtg gtttgtccaa  4440
actcatcaat gtatcttatc atgtctggat cgtctagcat cgaagatccc ccgatctgag  4500 gaaccctag tgatggagtt ggccactccc tctctgcgcg ctcgctcgct cactgaggcc  4560
gcccgggcaa agcccgggcg tcgggcgacc tttggtcgcc cggcctcagt gagcgagcga  4620
gcgcgcagag agggagtggc caa  4643
```

The invention claimed is:

1. A method of treating a condition associated with catecholamine dysfunction, said method comprising administering to an individual in need of treatment a one-vector expression system wherein said vector is an adeno associated vector (AAV), said one-vector expression system comprising:
   i) a first expression cassette comprising a human Synapsin 1 promoter operably linked to a first nucleotide sequence encoding a GTP-cyclohydrolase 1 (GCH1) polypeptide, and
   ii) a second expression cassette comprising a second promoter operably linked to a second nucleotide sequence encoding a tyrosine hydroxylase (TH) polypeptide, wherein said second promotor is selected from the group consisting of a human Synapsin 1 promoter and a CMV promoter, and wherein the second expression cassette comprises an enhancer or regulator selected from the group consisting of an intron and a Woodchuck hepatitis virus post-transcriptional regulatory element (WPRE), such that, after said administering, the TH polypeptide is expressed at a higher level than said GCH1 polypeptide in one or more cells or tissues.

2. The method of claim 1, wherein said second promoter is a CMV promoter.

3. The method of claim 1, wherein said enhancer or regulator is an intron.

4. The method of claim 3, wherein said intron is preceded by said second promoter.

5. The method of claim 1, wherein after said administering, the TH polypeptide is expressed in one or more cells or tissues at a level at least three-fold greater than that of the GCH1 polypeptide, wherein said level is an enzyme activity level, protein level, mRNA level, or a level determined by the concentration of Tetrahydrobiopterin ($BH_4$).

6. The method of claim 1, wherein one or both of said first expression cassette and said second expression cassette further comprises a polyadenylation sequence operably linked to said first nucleotide sequence or said second nucleotide sequence, respectively.

7. The method of claim 1, wherein the more 3' of said first and second expression cassettes comprises a 3' terminal repeat and the more 5' of said first and second expression cassettes comprises a 5' terminal repeat.

8. The method of claim 7, wherein said 5' and 3' terminal repeats are selected from Inverted Terminal Repeats and Long Terminal Repeats.

9. The method of claim 8, wherein said 5' and 3' terminal repeats are Inverted Terminal Repeats.

10. The method of claim 1, wherein the GCH1 polypeptide has an amino acid sequence at least 90% identical to SEQ ID NO:1, SEQ ID NO:2, SEQ ID NO:3, SEQ ID NO:4, SEQ ID NO:5, or SEQ ID NO:6.

11. The method of claim 1, wherein the GCH1 polypeptide has an amino acid sequence selected from SEQ ID NO:1, SEQ ID NO:2, SEQ ID NO:3, SEQ ID NO:4, SEQ ID NO:5, or SEQ ID NO:6.

12. The method of claim 1, wherein the nucleotide sequence encoding the GCH1 polypeptide comprises SEQ ID NO:18.

13. The method of claim 1, wherein the TH polypeptide has an amino acid sequence at least 90% identical to SEQ ID NO:7, SEQ ID NO:8, SEQ ID NO:9, SEQ ID NO: 10, SEQ ID NO:11, SEQ ID NO:12, SEQ ID NO:13 or SEQ ID NO:14.

14. The method of claim 1, wherein the TH polypeptide has an amino acid sequence selected from SEQ ID NO:7, SEQ ID NO:8, SEQ ID NO:9, SEQ ID NO: 10, SEQ ID NO: 11, SEQ ID NO:12, SEQ ID NO:13 or SEQ ID NO:14.

15. The method of claim 1, wherein the nucleotide sequence encoding the TH polypeptide comprises SEQ ID NO:21.

16. The method of claim 1, wherein the AAV vector is a serotype 2 AAV vector.

17. The method of claim 16, wherein the serotype 2 AAV vector is packaged in a serotype 5 AAV capsid.

18. The method of claim 1, wherein the catecholamine dysfunction is catecholamine deficiency.

19. The method of claim 18, wherein the catecholamine deficiency is dopamine deficiency.

20. The method of claim 1, wherein said condition associated with catecholamine dysfunction is a disease or disorder of, or damage to, the central and/or peripheral nervous system.

21. The method of claim 1, wherein said condition associated with catecholamine dysfunction is a neurodegenerative disorder.

22. The method of claim 1, wherein said condition associated with catecholamine dysfunction is a disease of the basal ganglia.

23. The method of claim 1, wherein said condition associated with catecholamine dysfunction is a disease selected from the group consisting of Parkinson's Disease (PD), DOPA responsive dystonia, L-DOPA induced dyskinesia (LID), ADHD, schizophrenia, depression, vascular parkinsonism, essential tremor, chronic stress, genetic dopamine receptor abnormalities, chronic opioid, cocaine, alcohol or marijuana use, adrenal insufficiency, hypertension, noradrenaline deficiency, post-traumatic stress disorder, pathological gambling disorder, dementia, and Lewy body dementia.

24. The method of claim 23, wherein said condition associated with catecholamine dysfunction is Parkinson's Disease (PD).

* * * * *